(12) United States Patent
Ishikawa

(10) Patent No.: US 10,359,424 B2
(45) Date of Patent: Jul. 23, 2019

(54) **PRIMER AND PROBE FOR DETECTION OF *MYCOBACTERIUM INTRACELLULARE*, AND METHOD FOR DETECTION OF *MYCOBACTERIUM INTRACELLULARE* USING THE PRIMER OR THE PROBE**

(75) Inventor: Tomokazu Ishikawa, Hyogo (JP)

(73) Assignee: FUJIFILM WAKO PURE CHEMICAL CORPORATION, Osaka (JP)

(*) Notice: Subject to any disclaimer, the term of this patent is extended or adjusted under 35 U.S.C. 154(b) by 15 days.

(21) Appl. No.: 12/994,751

(22) PCT Filed: May 26, 2009

(86) PCT No.: PCT/JP2009/059593
§ 371 (c)(1),
(2), (4) Date: Nov. 24, 2010

(87) PCT Pub. No.: WO2009/145181
PCT Pub. Date: Dec. 3, 2009

(65) Prior Publication Data
US 2011/0079512 A1   Apr. 7, 2011

(30) Foreign Application Priority Data
May 28, 2008 (JP) ................. 2008-139105

(51) Int. Cl.
*C12Q 1/68* (2018.01)
*C07H 21/02* (2006.01)
*C07H 21/04* (2006.01)
*G01N 33/569* (2006.01)
*C12Q 1/689* (2018.01)

(52) U.S. Cl.
CPC ......... *G01N 33/5695* (2013.01); *C12Q 1/689* (2013.01); *G01N 2333/35* (2013.01)

(58) Field of Classification Search
None
See application file for complete search history.

(56) References Cited

U.S. PATENT DOCUMENTS

| | | | |
|---|---|---|---|
| 5,474,796 A * | 12/1995 | Brennan | 427/2.13 |
| 5,487,972 A * | 1/1996 | Gelfand et al. | 435/6.1 |
| 5,541,308 A * | 7/1996 | Hogan | C12Q 1/6811 536/23.1 |
| 5,681,705 A | 10/1997 | Schram et al. | |
| 5,691,143 A | 11/1997 | Bustos et al. | |
| 5,840,488 A | 11/1998 | Hogan | |
| 6,248,526 B1 * | 6/2001 | Weimer | 435/6.11 |
| 6,294,328 B1 * | 9/2001 | Fleischmann | C12Q 1/689 435/6.15 |
| 6,465,638 B2 | 10/2002 | Gorman et al. | |
| 6,582,908 B2 * | 6/2003 | Fodor et al. | 506/9 |
| 6,773,882 B2 * | 8/2004 | Hogan et al. | 435/6.15 |
| 2001/0019822 A1 | 9/2001 | Gorman et al. | |
| 2007/0072188 A1 * | 3/2007 | Singh et al. | 435/6 |
| 2008/0241826 A1 | 10/2008 | Ishikawa | |
| 2009/0275026 A1 | 11/2009 | Ishikawa | |
| 2009/0285847 A1 * | 11/2009 | Felgner et al. | 424/190.1 |

FOREIGN PATENT DOCUMENTS

| | | |
|---|---|---|
| JP | A-10-4984 | 1/1998 |
| JP | A-10-323189 | 12/1998 |
| JP | A-11-69999 | 3/1999 |
| JP | B-3111213 | 9/2000 |
| JP | A-2001-103986 | 4/2001 |
| JP | A-2001-299354 | 10/2001 |
| JP | A-2003-135099 | 5/2003 |
| JP | A-2003-284565 | 10/2003 |
| JP | A-2005-204582 | 8/2005 |
| JP | A-2006-061155 | 3/2006 |
| WO | WO 02/077183 A2 | 10/2002 |
| WO | WO 2004/067702 A2 | 8/2004 |
| WO | WO2005/103249 A1 | 11/2005 |
| WO | WO2006/029014 A2 | 3/2006 |
| WO | WO2007/129628 A1 | 11/2007 |

OTHER PUBLICATIONS

NEB catalog (1998/1999 pp. 121, 284).*
Ahmed et al. (PLOS Oct. 1, 2007 issue 10 e968).*
Diffenbach (PCR methods and Applications (1993) vol. 3, pp. S30-S37).*
Roux et al (PCR Methods and Applications (1995) vol. 4, pp. s185-s194).*
Extended European Search Report dated Jan. 12, 2012, for European Patent Application No. 09754689.9, PCT/JP2009/059593 (10 pgs.) (including the Supplementary European Search Report and the European Search Opinion).
International Preliminary Report on Patentability for PCT/JP2009/059593, English translation, dated Nov. 27, 2008, PCT/IB/338, PCT/IB/373, PCT/IB/237 (8 pgs.).
Database EMBL [Online], "WLB1414G08.ab1 WLtestis Gallus gallus cDNA 5', mRNA sequence," created Apr. 4, 2004; last updated Feb. 8, 2011; Accession No. CN237871.
Office Action (Notice of Allowance) relating to U.S. Appl. No. 12/298,525, dated Jan. 26, 2012.

(Continued)

*Primary Examiner* — Katherine D Salmon
(74) *Attorney, Agent, or Firm* — Finnegan, Henderson, Farabow, Garrett & Dunner LLP

(57) ABSTRACT

The present invention relates to an oligonucleotide, comprising a part or the entire of the nucleotide sequence shown in any of SEQ ID NO: 1 to SEQ ID NO: 15, or a part or the entire of the sequence complementary to the nucleotide sequence shown in any of SEQ ID NO: 1 to SEQ ID NO: 15, wherein the oligonucleotide is capable of hybridizing with the nucleotide sequence of *Mycobacterium intracellulare* (*M. intracellulare*) gene; a primer or a probe for the detection of *M. intracellulare* which comprises said oligonucleoride; and a method for detection of *M. intracellulare* using said primer and/or the probe.

5 Claims, 2 Drawing Sheets

Specification includes a Sequence Listing.

(56) References Cited

OTHER PUBLICATIONS

Poly, Frédéric, et al., Identification of *Campylobacter jejuni* ATCC 43431-Specific Genes by Whole Microbial Genome Comparisons, Journal of Bacteriology, vol. 186 (14), p. 4781-4795, 2004, American Society for Microbiology.
De Beenhouwer, Hans, et al, Detection and identification of Mycobacteria by DNA Amplification and Oligonucleotide-Specific Capture Plate Hybridization, Journal of Clinical Microbiology, vol. 33(11), p. 2994-2998,1995, American Society for Microbiology.
PCT/ISA/237, Written Opinion from the International Search Authority, for PCT/JP2009/059593—in Japanese Language dated Jul. 30, 2008.
Extended European Search Report dated Dec. 29, 2009, for European Patent Application No. 07742686.4-2405 (12 pages) (including the Supplementary European Search Report and the European Search Opinion).
Saito et al., "Identification of Various Serovar Strains of *Mycobacterium avium* Complex by Using DNA Probes Specific for *Mycobacterium avium* and *Mycobacterium intracellulare*," *J. Clin. Microbiol.*, 28(8): 1694-1697 (Aug. 1990).
Yamamoto et al., "Polymerase chain reaction for the differentiation of *Mycobacterium intracellulare* and *Mycobacterium avium*", *Tubercle and Lung Disease*, 74: 342-345 (1993).
Yamazaki et al., "Identification of *Mycobacterium intracellulare* by a polymerase chain reaction using species-specific primers," *Tubercle and Lung Disease*, 76: 330-335 (1995).
Database EMBL [Online], "*Mycobacterium intracellulare* gtfB, drrC, genes for glycosyl transferase, putative glycosyltransferase, putative acyltransferase, putative methyltransferase, hypthetical [sic] proteins, DegT/DnrJ/EryCl/StrS aminotransferase, putative glycosyltransferase, daunorubicin resistance protein C, complete cds.," created May 8, 2008; last updated May 8, 2008; XP-002556511; Accession No. AB355138.
Written Opinion of the International Searching Authority related to Application No. PCT/JP2007/059251; filed Apr. 24, 2007; dated Nov. 13, 2008 (at WIPO web site).
Written Opinion from the International Searching Authority related to Application No. PCT/JP2009/059593; filed May 26, 2009; dated Aug. 11, 2009.
International Preliminary Report on Patentability, from the Patent Cooperation Treaty, related to Application No. PCT/JP2009/059593; filed May 26, 2009; dated Jan. 11, 2011.
Requirement for Restriction/Election relating to U.S. Appl. No. 12/298,525, dated Sep. 29, 2010.
Office Action relating to U.S. Appl. No. 12/298,525, dated Jan. 27, 2011.
Office Action (Examiner Interview Summary of Jun. 14, 2011), relating to U.S. Appl. No. 12/298,525, dated Jun. 16, 2011.
Office Action (Final Rejection) relating to U.S. Appl. No. 12/298,525, dated Sep. 28, 2011.
Office Action (Advisory Action) relating to U.S. Appl. No. 12/298,525, dated Dec. 7, 2011.
Yamakzaki et al., "Detection of *Mycobacterium Intracellulare* by PCR," *Kekkaku*, 68(11): 687-693 (1993).
Toshio Yamazaki et al.; Detection of *Mycobacterium Intracellulare* by PCR; partial translation of Kekkaku vol. 68, No. 11, pp. 687-693 (partial English trans. is 5 pages).

\* cited by examiner

[Fig. 1]
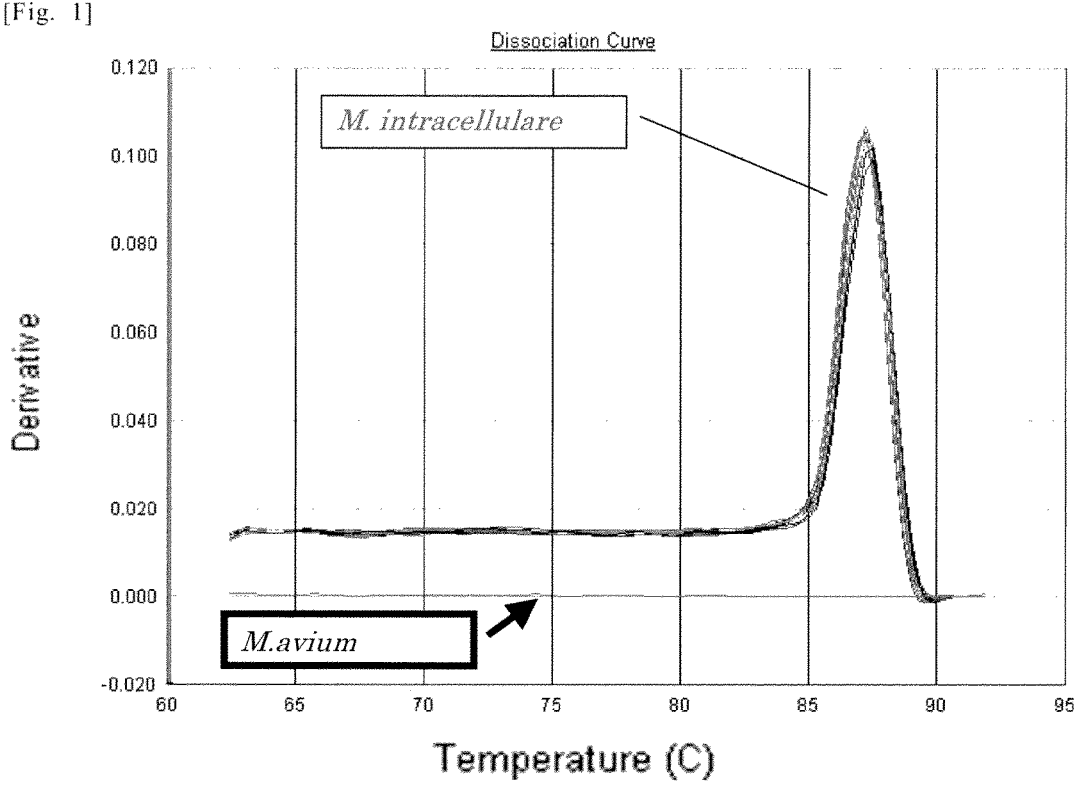
[Fig. 2]
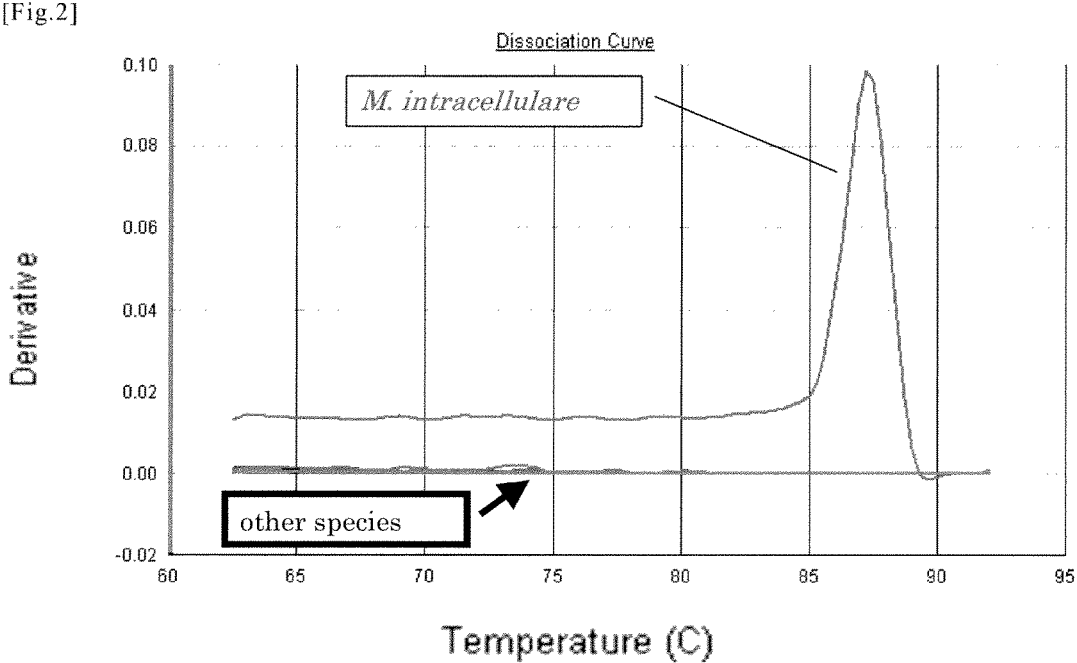

[Fig. 3]
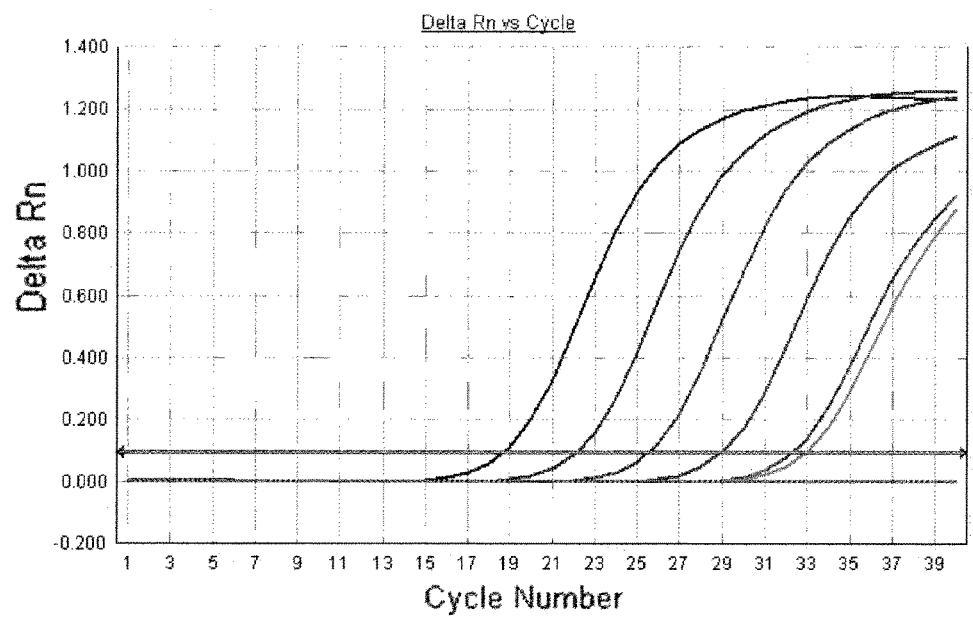
[Fig. 4]
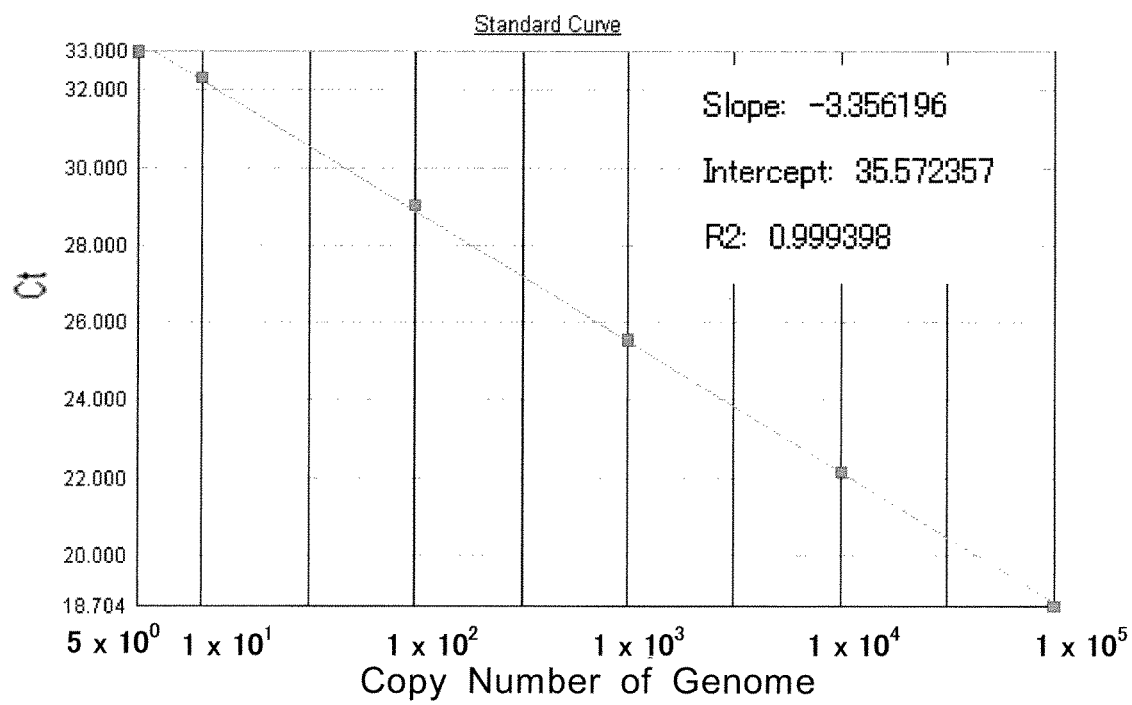

SEQUENCE LISTING

<160> NUMBER OF SEQ ID NOS: 129

<210> SEQ ID NO 1
<211> LENGTH: 597
<212> TYPE: DNA
<213> ORGANISM: Mycobacterium intracellulare

<400> SEQUENCE: 1
cgtagtactt gatcaccgtc tcgggatccg ggatggtgcc ggattgcaga aatttgtgcc    60

```
cagcgaacga catccagatt cgcgataggt caccgtcctt ccacactcgc gctcccatcg    120
ccaccaactc atcgaggagc ccggggaaca gctcctccat ggtctgcgtg gcgcgaactt    180
ggggaatgtg cggactgggg ccatgggggca ctccgcggcg ggccactggg cgttcgggca   240
gaacgtctcg ttccaccacg gtcaccgtgg tgtagtagtc agccagaaca cgggcggcca    300
tcaggccggc gatgcttccc cccagaacga ctgcggtttc gccgaattca ggcacactga    360
gtctccttct gatccgtttt tgtcggcgga cgacgcgcga ggactaacag ctgattgcga    420
aggcggccat catcagcaag accgtggcga ggccgtgcag acaagttgt cgcaaaacga     480 catcccggcc aagcgagtcg tccaattcgg tcgaccgcga ataatccggg atcacaaagc    540
gatagcgctc tgagccgaat ctcgttctcg tgcttcggtg tgtgttcatg cccatcc       597

<210> SEQ ID NO 2
<211> LENGTH: 573
<212> TYPE: DNA
<213> ORGANISM: Mycobacterium intracellulare

<400> SEQUENCE: 2
tgggcactct gaacggtagt ggtcatgaac ggagatgttg cctcagatcc tcctcagtga     60
gcacggcctc cagcgggcct gattcatcag atgaacccgg cgtagttctg ccgtctggtg    120
cataagccca caccagccct gggtcagatt gcaccgcaac atctttgatg tcggcgctta    180
accgacttat tccatgaacg ctcgcgctgc gtgctctgcg acgagcatga gcggcgcgtt    240
ggtattgccg gcagtggcgg caacaccta tcgcacgtcg ccgcttggac gacccgcatg     300
gaggttccac tggccgcagt cggggggccag gacgtcgttg acgtcaactt cgaatccgcc    360
gaccttcggc ccgggattgg acgcggtgct cacgacgcgc tggtaaagaa cagcggcggg    420
gtggacctga tcaccggacc aggctcgagt ttgccaggcc caccggcggc caggtgtgct    480
cgaagacccg ataacgccat cggccgcggc ccactggcag accctgacac ctccgtagac    540
cccagtgcgc tgaaccccaa gaactgagtt gat                                 573

<210> SEQ ID NO 3
<211> LENGTH: 677
<212> TYPE: DNA
<213> ORGANISM: Mycobacterium intracellulare

<400> SEQUENCE: 3
cgatacatcc cgtggtacga ggggaatgtg tacgtcttga acgtgctgtt cccattgctc     60
gctgtcgcag gtatcggcgc gggcagtgca cccggcaatc ccgcgtggct tcggttcatc    120
ggaggtatct gcctgtcggc gccgctgcgg tcggcgtcgg catcatttat gggagcggcc    180 gccgaattt cggcgccggg gtcaggcgga ccggcagga gattgtctgc cgctatcttc      240
cgtggtacga gagcaacccca tacatggcga ccttgctgtt ccccctaatc gcgatcgcca   300
tgattggcgc aggatgtgca cccggtaatc cggcgtggct gtggtacggc ggggccattc    360
tgctggccat ctctgcctta ttggtgggag tctccctctg gatctggcgc cgatcccttc    420
tccgtatcac ccccgcggcg ttgaccgtgc ggatcgcaga gcgcggcagt gagttgaccg    480
acatccggcg tgagcatgtc cgttcgatcg agccaaagct cgtcccgagc gtggcggccg    540
gtaccgagcg gttgcaagtc gaagtcgcct accagcccgc cgatgtcagc agcgaggcga    600
ccgcgacggt gatgctcgga atgtatctga gcgttcaacc gatcaacctg ctcaacgccc    660
tcgtggcctg aaagacg                                                   677
```

<210> SEQ ID NO 4
<211> LENGTH: 926
<212> TYPE: DNA
<213> ORGANISM: Mycobacterium intracellulare

<400> SEQUENCE: 4

| | | | | | |
|---|---|---|---|---|---|
| tcgaacggac | atgctcacgc | cggatgtcgg | tcaactcact | gccgcgctct | gcgatccgca | 60 |
| cggtcaacgc | cgcggggggtg | atacggagaa | gggatcggcg | ccagatccag | agggagactc | 120 |
| ccaccaataa | ggcagagatg | ccagcagaa | tggccccgcc | gtaccacagc | cacgccggat | 180 |
| taccgggtgc | acatcctgcg | ccaatcatgg | cgatcgcgat | taggggggaac | agcaaggtcg | 240 |
| ccatgtatgg | gttgctctcg | taccacggaa | gatagcggca | gacaatctcc | tgcccggtcc | 300 |
| gcctgacccc | ggcgccgaaa | attcggcggc | cgctcccata | aatgatgccg | acgccgaccg | 360 |
| cagcggcgcc | gacaggcaga | taccaagccg | acccaaccag | cacatttatg | cccgccaaca | 420 |
| ggcatagtgc | accaccgacg | gcgtaacgca | gtttcggtac | acgacgtttc | gctgtattac | 480 |
| ttgccatcag | caacggtccc | gtgttcggtt | ctcgggatag | cgccgtggta | ccccgcggac | 540 |
| gttggatttg | tcaccggacc | cgatcgagtg | gtcagccaga | cacccgatcc | atccatcggt | 600 |
| gaatcgtgta | acgcggtcac | tgttagttgc | gcgatcagcg | tctcccgttc | ggccgtgatg | 660 |
| atcctcgatt | gtgacgtgct | gtcgatggtg | ccgagttcat | gcgcgatctg | gatcgcgagc | 720 |
| gtccccgcgc | taccgggacc | ctcgcgtgct | gcggtgaatt | ctcgatgcag | ttcacggcat | 780 |
| tcggcgccg | actgcaactg | ctggtcagac | agcatggcaa | atacttcggg | tggatccagc | 840 |
| gaggcctcga | cccgatgcat | cgtcaacacc | gcgtttgcgc | aaaacacgtc | gatacatggg | 900 |
| tcggcacgac | aaacccacac | acgaac | | | | 926 |

<210> SEQ ID NO 5
<211> LENGTH: 593
<212> TYPE: DNA
<213> ORGANISM: Mycobacterium intracellulare

<400> SEQUENCE: 5

| | | | | | |
|---|---|---|---|---|---|
| tttggcccac | ttcgcggcca | agacgggagc | gtcaatatgg | cgccgcatga | cgaccacaca | 60 |
| cactgccggg | ggccggcatg | ccccgccgct | acacacaccg | cgcctgcgcc | tgaaaccgaa | 120 |
| gtcgccccgc | agcgggtatg | tcgatggagc | gtggtggccg | catagtgacg | acctgacggc | 180 |
| ggagctgcca | gatctgctgg | cagtgctatc | ggttcggctt | ggtcccgtgg | gtcgtgtcat | 240 |
| ctacaacctc | accgaatggg | caacggcgcc | agcaaaattg | gcgttcggcc | cgcagacggt | 300 |
| acggctcgac | ggataccgcc | gccagccggt | tcacaccgtc | gaggtgctcg | ggctcaatcg | 360 |
| ccagagaatc | accctcctgg | tggtttcacc | gcacaccgac | gaaaacgatg | cgcacaccgt | 420 |
| catgatgacc | gcggccggcc | cgaacaacgc | cttgacggtc | gcgaacctca | tgatcagcgg | 480 |
| gcaaaaagtg | gacgcccgcg | agtagaccat | gtcggccaca | tcacgcatca | gcgccggatt | 540 |
| cgactgaccc | tgtttaacct | gacttcacgg | tgcatttcg | ccgaccatgc | gcg | 593 |

<210> SEQ ID NO 6
<211> LENGTH: 941
<212> TYPE: DNA
<213> ORGANISM: Mycobacterium intracellulare

<400> SEQUENCE: 6

| | | | | | |
|---|---|---|---|---|---|
| cttgccgatg | cccgggagca | gcgactgcac | cgtgcgcggc | ttcagcaggt | ccgcggagac | 60 |
| ccgcgcatag | taattcgcgt | tggcgaccag | gtcgacgatc | tcctcctgtg | cggcccatcg | 120 |

```
ggccttgccc gcctcggcct gcaggagatc catcaggaac tcgcggttct cgacgaccag    180
gtcgcgatac cggctgatga catcgacgcg ctcgctgacc ggacggttcg cccagtcggc    240
ctgcgccgcg cgcgcctcgg cgaaggcggc ttcgacgtct tcggccgtgc cgacggggat    300
ggtggtcagc ggcttgccgg tgaagacctc gtcgatcgtc ttggtctggc gtgcggtggc    360
gttcttgatc gcggccaact ggcgcaggcg gtcgaagacc tcggctgacg gtgcgggcat    420
gtcgtcacct ctcaaaaagc gcaggcgtcc aaaacaccag actattggct ctgcgatgcc    480
gggggtctcc ggtgcccgtg ggcttgtttt gagcggctat caccgagtgg aagacgctga    540
tgagtccgaa ggctttgaga actcatgtag cctcgggtat cgaccaaccc acgagccgat    600
caggcaggtg ctctcacaca gatgatacgg ccgtccaccg gaccggtagg tcccggacgc    660
gtcgccgtgc cgccccaacc cgcgggccgc tttctagat cgagaagttc gccgcttatc    720
tgacctcgcg tcgatcctcg ccactcgcgc gtaaccaccc acaagatcgg acgtgacccc    780
ttttgccgcg gttcgtaaac ccgccctgtc cgcatgcctc cgctcagccc gaatctcact    840
gattccatgg cgattaccga agtacctgaa tacgcccacc tcagcgatga cgacgtcgag    900
aacctcgcgg ccgcactgga cacgatccgt tgcgacgtcg a                      941

<210> SEQ ID NO 7
<211> LENGTH: 602
<212> TYPE: DNA
<213> ORGANISM: Mycobacterium intracellulare

<400> SEQUENCE: 7
ctgaccgcct cagtcgatga agatgggcat gaacacacac cgaagcacga gaacgagatc     60
ttggctgttc gccggcgacc acaacgttca tgtggaaagc cggatgttcg cggccccatt    120
tgcggcgccc gtcaccaaag tacgtgtggt ggtgatgtcc gctcaggggc atggcgataa    180
ggtccgtggt gtcgacggcc ggacccacca attcgtatgc cgatttgttt tcgaaccgcc    240
agatcgctgc agtaagaaca ccgccggagc cggtgatgcg ttgtccgggc ttgaagccca    300
ggcactcaga aacaacttcg ggcgtgacga atccgggccc agtcatgctt ggacgccctg    360
cccaggcgcc gtgtggacgc cgcgcgccga ccggtcgcgg tcatccgaga tcacacaaac    420
aagtctcgac tcggtgtcgg gccttcagcc accgatgatg ggacacgttt cccacagata    480
gcgacatcgt ccggctacgc acgacattcc cgaaatcggt gcgtctctcg tgcacaaggt    540
acgcgccgca gacacgccag tgacccacct gtcgcggtag acacgtccgg acgtttcgtt    600
tt                                                                   602

<210> SEQ ID NO 8
<211> LENGTH: 1346
<212> TYPE: DNA
<213> ORGANISM: Mycobacterium intracellulare

<400> SEQUENCE: 8
caacttcgaa tccgccgacc ttcggcccgg gattggacgc ggtgctcacg acgcgctggt     60
aaagaacagc ggcggggtgg acctgatcac cggaccaggc tcgagtttgc caggcccacc    120
ggcggccagg tgtgctcgaa gacccgataa cgccatcggc cgcggcccac tggcagaccc    180
tgacacctcc gtagacccca gtgcgctgaa ccccaagaac tgagttgatt ccgcgaaacc    240
acggcagcgc ggtgtgaatc caggtattgc ggttgatgtc ctcgtcgatg gtgaagaaaa    300
tcggcgcact ctggccgccg cctgccgcgg tgtgcaaacg ccaggcggtg cgcgcatccg    360
```

-continued

```
cgacgccgcc cgcgtagccc cgcgtgaagt ctgacggtgt cgacccaccc ggcttgccgt      420
attggtagtt actgacaatc accaaacccg cagctgtcag tgagtcggcg taggaccgag      480
tgatgggctt ggcgccgaac gaggagccgg ggcgtgacaa cgagacgtag ttgaccaccc      540
cgctatagcc ggcggcccgg atctgctgcg ccggaatctg gtgtgcggca aagtcgatca      600
gctgaggggg agcggcggca gtcgctgtcg gcatgccgca ggctaccgat gcggcaccca      660
gaccggccaa cgtggcggcg tagcgcagcg cgtcgcgccg ggagacagtg cgcaatggca      720
catcggtggc ggcagagggc aaattgcgca cggcgcaagg ttaaacatgt gactgttgtt      780
accgatagtg ctgcgccagt cgaaacgcgg ttgcatgccc aaatagatac caagtggtga      840
tcgttcggct ataaccacga aaggacatgc gggagaacga cctaccgacg atcgcccgcg      900
ctgcgcgctc ggcgatgcgc atggtcggcg cgttggtgtt gccggaagtg atggtgggca      960
tagccgaagc atcggccggt caacatccat gttggattgg tgcatatccc tcccgcgccg     1020
cagcagggag ggtctttagt cacgatggca acttcaccgc ggctcaccct gctcgccgcg     1080
cagtgcagga gcacgactgt gctgtggccg ctaaggatcg ttaccgcaat cgtgatctcg     1140
cgctcggtga ttggcgtcgc gcggccgca atcttgacaa tggggttagc ccgacgcagc     1200
ttcgcgcctc tacggcgaac ggaaccttga gcagcggttg accatcagcg cgcggactgc     1260
cgccaaccct gtgagatcaa cgtccgcctc gctgataccg caaatgccgc atcgatagcc     1320
ttgctcggct cgaagggcgt cgtact                                          1346
```

<210> SEQ ID NO 9
<211> LENGTH: 1219
<212> TYPE: DNA
<213> ORGANISM: Mycobacterium intracellulare

<400> SEQUENCE: 9

```
tgaatacatc tccgtcgcgg acaaagatcg catccggttc gacgctcacc tcggggaaga       60
tgcgggccaa ccgcccggta tgccgccagt gcgtggtcgc ccgcttgcca ttgagcaggc      120
ccgcctgcgc caggatgaag gaacccgtgc aaacggatgc caagcgccgg gtccggcccg      180
ggacggtctt gagtgcttcg atgagagcgg gatcgatcgg ccgcccgatc agtgtgtcac      240
cgcccgcgac catgacggtg tcgacggatt cgagggccga gaggggacac gtcacagcga      300
atcgggtgcc gatcgacgtg gtcacatcgc gtccgtctac cgatgcgatt tcgagcgaat      360
agcgtgcgcc gaaccgattg gcttcggcga acacctcggc gggacccgca acgtccaaca      420
gtttcacgcc gtcgaagacg acgatcacca ccacacgagt tgttgcgttg gcctccgcca      480
tacgcccatc gtgtcgcgcc ggcgacgacg agtacaagcc ggagggtgtc acaacgtgtg      540
gatcggcgac atgaacggcg atcacctgag aaacgctgcc ggataagtgg cggcgtgcgc      600
gacgctggac tcacactgcg acaaagaaat tcaccggggg cggaacctgg gggctcaagc      660
tcttgtcagc gcgtgacatc atcgtgaacg acgcctggcg cccgaacagc atcctttggc      720
cagcgggtgg ctgaccacgc gactattctc gacaccgtgg acccggtgtc gccgccacgg      780
aatggtggtg gcctgatagg ccggcacgcg gaatgtgttg cgctggaaca gcttctcacc      840
cgcgtgcgcg ccggtgagag tcgtgttctg gtacttcatg gagagccggg tgtcggtaag      900
acggccttgc tggactacgt cggtgaacgg gccgccggct gtcgcgtcat ccgtgccagc      960
ggggtcgagt cggagatgga gctggcctac gccgcggtgc accagttgtg cgcggcgatg     1020
ctcgatcgtc tcgattatgt gccggtgccg caacgcgacg ctttgagcac ggcattgggt     1080
caaacgatag gtcccgcacc ggaccgcctt ctcgtcgggt tggcggtgtt gaacatgttc     1140
```

```
tccagcatgg ctgaggtcga gccgctcgtt tgtttggtcg acgatctgca gtggctcgac    1200
caggcctcgt cgcagacgc                                                 1219

<210> SEQ ID NO 10
<211> LENGTH: 1122
<212> TYPE: DNA
<213> ORGANISM: Mycobacterium intracellulare

<400> SEQUENCE: 10
aagagtgcaa gatcaagatt gcggcaacgc tccttaacgg tcgcagcaca acctccccgc     60
tccaggaaca atggaccatg cgcagcgacc gtcccctcga aatcgcgctc ggcattgcgc    120
tggccactcg gcgattctga aggcatgaca tcggactggc gccgaatac gacggattcg     180 aatatgcagt gttaccggga atccggacgg ttccgcgatc gcacgtcgcg gttaccgttg    240
gtggcctgag gcaagctttg gccatgacat cgactccctc tgatgtggaa ttaatccgcc    300
tgaggtgatc gacggctcgg cccgttcgac aggataaggc gatgccgccg tacggattcg    360
acattgatga tgagttgcac gatcagttgc gtgctccagt tccaccgggc gtactggcat    420
gggttgagcg ccagacaaag tgtcaggtca ttgcgcagcg gccgttggaa ggcggccagt    480
ccgcggcgat tcaccgcctt gttctcgatg accgaagcgc tgtgatcctg cagcgattcg    540
tcttggattg gatccgcgac gagccgtggg ctcctgcgaa cgaggtactg gtcttaggtc    600
ttttggccga tacatcggtt ccagcgccga aggtgattgc cgccgacccg cacggacagg    660
acaccggtgt tcccaccgta ttgatgaccg cactgccacg cgccgtcgtg tgggacccac    720
cagagctgga cccatggttg gacgccgtca tcgacgtcat gatgacgatt catgccatac    780
gggcgccgca acagttacgc cggtgggagc cttacccgcc ggagaacgcc ccaccggcgt    840
ggacccgcta tcggtgggca tgggaacgcg ccgtcaccac gtaccatgat gtgcgcccaa    900
gcagcgaccg tgtgttctta caccgcgatt ttcatcccgg caacatcttg tggcagcaag    960
gcaaaatatc cggacttgtc gactgggtct cgtcgtgcgc cggacccgtc caggaggata   1020
ccgcccactt ccgcgtgaac ctggccatgc accacggaca aggcgtcgca gatcgcttcc   1080
tgcggcgctg gatgcgcgcc agcggccagt ttgaatacca cc                      1122

<210> SEQ ID NO 11
<211> LENGTH: 1119
<212> TYPE: DNA
<213> ORGANISM: Mycobacterium intracellulare

<400> SEQUENCE: 11
gcttctttcg gcaccgacgt gccgcgacca ctgtggcccg gtagcgacga accaatcctg     60
ggcaatcggt tgcggcaggt gaatcccgac tgccgatgtt gagagccaag gattccattc    120
cacatcgatc aaatcgggga gattgcgtga gcacttcaaa caagggcatt ttcgctcgac    180
gccacgacga cgcgcgtgga cgccctgtga acgggcatca gcggctgctc ggccaaaccg    240
ggttccggat ggtccggaaa gccgacactc caacggattt cagcgtcgtc gaagcccgcg    300
tcagatgact tcgacaccaa tgccggcacc cgaggttgcc gcgcgctacg acttcgtgat    360
ctgtgggtca gggtcttctg gatcggtcgt cgccggtcgg ctttcggaga atccggacgt    420
tacggtgctt ttgctcgagg ccggtgaaac cgatgatgtt tcggcagtcc acgatcccac    480
gcagtggccg ctgaacttgg gtagcgacg tgactggtgt ttcgtctcgc agccgagcgc    540
ccatctcaag ggcagatcgg tgctgctgtc gatggggaag gtgctcggcg ggggtcgag     600
```

```
catcaacgtg atggtgtggg ctcggggaca tcgaagcgac tgggactact tcgcaaccca    660
ggcgggtgac gaagcctggg gctatgaatc ggtgcttgac atctaccgtc gcattgagga    720
ttggcacggg ccggcagtct ccgcccgcgg caccggggc cccatgtccg tgacgtcccc    780
gcccgacccc aatccgatcg ctccggccat cgtcgaggcc gctcgctcgc tggggatccc    840
gagctatccg agcaacaacg gcgccatgat ggaccgcggc ggcggcgcag cgctcttgga    900
cgtgacattg cgaaacgggc tgcggcagtc cgtgtatcgc tcctacgttc atccgcacct    960
gcaccgcccg aacatgacag tcctcaccgg tgcgacggtg actcggttgg tcgtcggccg   1020
aaaccgggct acggcggtcg agttctcgca caacgatcgg acgcaccagg tcgtcgcagc   1080
acacgaggta gttgtttcgc ttggggcgat caacacgcc                          1119

<210> SEQ ID NO 12
<211> LENGTH: 395
<212> TYPE: DNA
<213> ORGANISM: Mycobacterium intracellulare

<400> SEQUENCE: 12
cggcggatcc ccttggtcgt tgcacgaggc gaacgagaat gccccgctga cgccctccag     60
cttcgcggcg gcgacgatct gcttggccgg ctcgatcacc tgcgccttgg tctgatcgtc    120
gctcatggga tgggccgtat cctcgtacgg attcgtcgat cccgcggcat gtggtttgtg    180
tagcactggc gcgcatcctc ctaacaacac ggcgacgacc actagcgaac tgatcagcgc    240
ttggcgcaac ggcatacgtt gttcctcaat ggtggtgttg agcatcgaaa acatggttgt    300
cggtaataga tcctggcgac cgctcccact ccgggtcgat gacggcaggc gtgtgcgggc    360
cgatggtgac cgcacaacag atttgcccgt atgcg                              395

<210> SEQ ID NO 13
<211> LENGTH: 902
<212> TYPE: DNA
<213> ORGANISM: Mycobacterium intracellulare

<400> SEQUENCE: 13
cccaacacgc ccacgctgga agcgatgaca cggcacctcg aatacgccgt cgacctcgtc     60
ggcatcgagc acgtcggtat cagcaccgac ttctgtttcg acgccgccga tttcgccaac    120
gagctgcgcc gcaatcccca cctgttcgac gccagctaca cccgctgggg cccgatccag    180
tgggtgccgc cggaaacctt tgtgacactc ggtgagcacc tgcggggaag gggatggaac    240
ggtcgtgaca tccacgcggt cctcggtggc aacttctatc gggtggccaa caagcctgg     300 cgcgcctgaa caggccaccg gcgcatcact tcacggcagt tcgaccttgc tggccagcca    360
tcggcagata gatgtccacg atggcgcccg cgtcctcggg cgtggccatt cttagcctca    420
cgaccacaga aggctagccg cacgacggcc gatggtcgcg gccttcagga aaagaacctg    480
gccataaggg cttctgcgaa cgggcgatgc gtggtgtttt gcgaagacgc gagcaaccag    540
cgcccgtcgg tccgcacggc gacactggtg ttcacccggg cattgcgccg gttgcgtcgc    600
cgcctcacca ccgtcgcgtt cgcgtgaatc agcgccacgt cgggtgtgag aaaccggagc    660
tgggcgacgt cgatccgtag ccgggtgccc ttgaggagct tgcggaacag cggggcgtac    720
gacggatcct ttctcttgat gctgtcgctg atccgggaca actgaaatgc caagtggacc    780
atggattccc cgccgtataa cggcgaatag gggccgaagt gtcgggttcg ttggtgatga    840
tcagcggctt caccccgcggg cccagaaagg ccgtcgaccg atcgatgttg gcgacaacgg    900
ca                                                                  902
```

<210> SEQ ID NO 14
<211> LENGTH: 952
<212> TYPE: DNA
<213> ORGANISM: Mycobacterium intracellulare

<400> SEQUENCE: 14

| | | | | | |
|---|---|---|---|---|---|
| gacgtgacca | agcagtacgg | ccggggccgg | tcggccgtca | cagccctcga ttccatcacc | 60 |
| ttgacggtca | actccggtga | attcgtctgc | gttgtggggg | catccggctg cggtaagagc | 120 |
| tcactgctgt | cgctgatcgc | cgggatggac | caaccgtccg | ccggcgagct cagcaccgat | 180 |
| gggcaacggg | tggccttgat | gtttcaggaa | ccggcactgt | tcccatggct gacgtcggcc | 240 |
| gccaacgtcg | agttggcctt | gcgggcgcgc | tcggtgccgc | gcccgcaacg ccgccagcgg | 300 |
| acgactgact | tgttgcaaac | ggtcggcttg | gctgactttg | ccgacaaccg tcctcatcag | 360 |
| ctgtccggtg | gcatgcagca | gcgcgtcgca | ttggcgcgtg | cgctcgccca agacgccgac | 420 |
| gtcttgctga | tggacgagcc | gttcggggcg | ctggatgccc | tgacccgtga tcgcctgcac | 480 |
| gaagaactcg | agcgcatcgt | tgacgaacgc | ggactgaccg | tcgtgttcgt tacgcacaac | 540 |
| gttcgcgagg | cagtgcgact | cgccgatcgt | gtcgtattgc | tcagcccgcg gcccggtcgc | 600 |
| atcgtcgaag | agatcgcggt | cccggtggcg | cggcgccaca | gagtcaacaa cccgggcgtt | 660 |
| gccgaattgg | cctcccgcat | ctccacccag | ctacggaacg | agggaaaccg tggcggtgct | 720 |
| tgacagcgat | ctcgctacca | agagtcaccg | gcctgcatcg | acgccgcaag cgccgcaccc | 780 |
| gaaccgcatg | cggatcaggt | cggtgctggc | ggcgatgcgg | gcgaaagtct ttgccgtcgc | 840 |
| gatggttctg | ctgatctggc | agctcgtgta | cctcagcggg | tggaagccgt cattcgtgct | 900 |
| gcccggcccc | ggaaccgtcg | cggccaacct | ctggcagcgg | ctgcatgagg cc | 952 |

<210> SEQ ID NO 15
<211> LENGTH: 460
<212> TYPE: DNA
<213> ORGANISM: Mycobacterium intracellulare

<400> SEQUENCE: 15

| | | | | | |
|---|---|---|---|---|---|
| cgaagatcaa | attcgccgcc | acatccaccg | tcagcgtcgg | gggtagctgt cgttgaagcc | 60 |
| ggtgcggatt | tcgctgacgt | aatagacgag | ggtcccggtg | agcagcaccg cgacgccgaa | 120 |
| gaacgtcagc | caaagacact | tgatccgcga | ctcgtcgggt | aaatccttgc gcaacaaacg | 180 |
| aagccacacg | atggtgagca | tgatgccgac | gagcactgcg | ccgaattcca ggccgaagat | 240 |
| ccacgggtcg | tcgctgcggt | agcgggtatc | ggccaggccg | tactgccacc acagccaccg | 300 |
| ccaccctggg | tccgtggtgg | cggtccacag | gttgaacggg | tgaccgagca agaacggcaa | 360 |
| ctcataggtc | agctggcttc | ccgccgtcag | agggatgtag | atcagtgtca gctcggccgc | 420 |
| aagctgcaga | cgggatcgct | gctctcccct | tcccttcccg | | 460 |

<210> SEQ ID NO 16
<211> LENGTH: 22
<212> TYPE: DNA
<213> ORGANISM: Artificial
<220> FEATURE:
<223> OTHER INFORMATION: oligonucleotide primer

<400> SEQUENCE: 16
cgtggtgtag tagtcagcca ga                                              22

<210> SEQ ID NO 17

```
<211> LENGTH: 21
<212> TYPE: DNA
<213> ORGANISM: Artificial
<220> FEATURE:
<223> OTHER INFORMATION: oligonucleotide primer

<400> SEQUENCE: 17
aaaaacggat cagaaggaga c                                          21

<210> SEQ ID NO 18
<211> LENGTH: 18
<212> TYPE: DNA
<213> ORGANISM: Artificial
<220> FEATURE:
<223> OTHER INFORMATION: oligonucleotide primer

<400> SEQUENCE: 18
gcgaacttgg ggaatgtg                                              18

<210> SEQ ID NO 19
<211> LENGTH: 18
<212> TYPE: DNA
<213> ORGANISM: Artificial
<220> FEATURE:
<223> OTHER INFORMATION: oligonucleotide primer

<400> SEQUENCE: 19
cgaaaccgca gtcgttct                                              18

<210> SEQ ID NO 20
<211> LENGTH: 19
<212> TYPE: DNA
<213> ORGANISM: Artificial
<220> FEATURE:
<223> OTHER INFORMATION: oligonucleotide primer

<400> SEQUENCE: 20
ggccatcatc agcaagacc                                             19

<210> SEQ ID NO 21
<211> LENGTH: 20
<212> TYPE: DNA
<213> ORGANISM: Artificial
<220> FEATURE:
<223> OTHER INFORMATION: oligonucleotide primer

<400> SEQUENCE: 21
atgaacacac accgaagcac                                            20

<210> SEQ ID NO 22
<211> LENGTH: 18
<212> TYPE: DNA
<213> ORGANISM: Artificial
<220> FEATURE:
<223> OTHER INFORMATION: oligonucleotide primer

<400> SEQUENCE: 22
gcgaacgaca tccagatt                                              18

<210> SEQ ID NO 23
<211> LENGTH: 18
<212> TYPE: DNA
<213> ORGANISM: Artificial
<220> FEATURE:
<223> OTHER INFORMATION: oligonucleotide primer

<400> SEQUENCE: 23
```
accgtggtgg aacgagac					18

<210> SEQ ID NO 24
<211> LENGTH: 20
<212> TYPE: DNA
<213> ORGANISM: Artificial
<220> FEATURE:
<223> OTHER INFORMATION: oligonucleotide primer

<400> SEQUENCE: 24
gcctcagatc ctcctcagtg					20

<210> SEQ ID NO 25
<211> LENGTH: 19
<212> TYPE: DNA
<213> ORGANISM: Artificial
<220> FEATURE:
<223> OTHER INFORMATION: oligonucleotide primer

<400> SEQUENCE: 25
gcgagcgttc atggaataa					19

<210> SEQ ID NO 26
<211> LENGTH: 19
<212> TYPE: DNA
<213> ORGANISM: Artificial
<220> FEATURE:
<223> OTHER INFORMATION: oligonucleotide primer

<400> SEQUENCE: 26
gacgcgctgg taaagaaca					19

<210> SEQ ID NO 27
<211> LENGTH: 20
<212> TYPE: DNA
<213> ORGANISM: Artificial
<220> FEATURE:
<223> OTHER INFORMATION: oligonucleotide primer

<400> SEQUENCE: 27
ctacggaggt gtcagggtct					20

<210> SEQ ID NO 28
<211> LENGTH: 18
<212> TYPE: DNA
<213> ORGANISM: Artificial
<220> FEATURE:
<223> OTHER INFORMATION: oligonucleotide primer

<400> SEQUENCE: 28
agagcgcggc agtgagtt					18

<210> SEQ ID NO 29
<211> LENGTH: 20
<212> TYPE: DNA
<213> ORGANISM: Artificial
<220> FEATURE:
<223> OTHER INFORMATION: oligonucleotide primer

<400> SEQUENCE: 29
gatacattcc gagcatcacc					20

<210> SEQ ID NO 30
<211> LENGTH: 19
<212> TYPE: DNA

<213> ORGANISM: Artificial
<220> FEATURE:
<223> OTHER INFORMATION: oligonucleotide primer

<400> SEQUENCE: 30
atacatggcg accttgctg                    19

<210> SEQ ID NO 31
<211> LENGTH: 20
<212> TYPE: DNA
<213> ORGANISM: Artificial
<220> FEATURE:
<223> OTHER INFORMATION: oligonucleotide primer

<400> SEQUENCE: 31
gccagatcca gagggagact                    20

<210> SEQ ID NO 32
<211> LENGTH: 18
<212> TYPE: DNA
<213> ORGANISM: Artificial
<220> FEATURE:
<223> OTHER INFORMATION: oligonucleotide primer

<400> SEQUENCE: 32
ggcgtcggca tcatttat                    18

<210> SEQ ID NO 33
<211> LENGTH: 18
<212> TYPE: DNA
<213> ORGANISM: Artificial
<220> FEATURE:
<223> OTHER INFORMATION: oligonucleotide primer

<400> SEQUENCE: 33
cacatcctgc gccaatca                    18

<210> SEQ ID NO 34
<211> LENGTH: 20
<212> TYPE: DNA
<213> ORGANISM: Artificial
<220> FEATURE:
<223> OTHER INFORMATION: oligonucleotide primer

<400> SEQUENCE: 34
ctcccaccaa taaggcagag                    20

<210> SEQ ID NO 35
<211> LENGTH: 18
<212> TYPE: DNA
<213> ORGANISM: Artificial
<220> FEATURE:
<223> OTHER INFORMATION: oligonucleotide primer

<400> SEQUENCE: 35
gaccgggcag gagattgt                    18

<210> SEQ ID NO 36
<211> LENGTH: 18
<212> TYPE: DNA
<213> ORGANISM: Artificial
<220> FEATURE:
<223> OTHER INFORMATION: oligonucleotide primer

<400> SEQUENCE: 36
gcgcctgaaa ccgaagtc                    18

<210> SEQ ID NO 37
<211> LENGTH: 19
<212> TYPE: DNA
<213> ORGANISM: Artificial
<220> FEATURE:
<223> OTHER INFORMATION: oligonucleotide primer

<400> SEQUENCE: 37
aagccgaacc gatagcact                                                  19

<210> SEQ ID NO 38
<211> LENGTH: 20
<212> TYPE: DNA
<213> ORGANISM: Artificial
<220> FEATURE:
<223> OTHER INFORMATION: oligonucleotide primer

<400> SEQUENCE: 38
cagagaatca ccctcctggt                                                 20

<210> SEQ ID NO 39
<211> LENGTH: 19
<212> TYPE: DNA
<213> ORGANISM: Artificial
<220> FEATURE:
<223> OTHER INFORMATION: oligonucleotide primer

<400> SEQUENCE: 39
tggccgacat ggtctactc                                                  19

<210> SEQ ID NO 40
<211> LENGTH: 18
<212> TYPE: DNA
<213> ORGANISM: Artificial
<220> FEATURE:
<223> OTHER INFORMATION: oligonucleotide primer

<400> SEQUENCE: 40
ccgtgggctt gttttgag                                                   18

<210> SEQ ID NO 41
<211> LENGTH: 20
<212> TYPE: DNA
<213> ORGANISM: Artificial
<220> FEATURE:
<223> OTHER INFORMATION: oligonucleotide primer

<400> SEQUENCE: 41
ggccgtatca tctgtgtgag                                                 20

<210> SEQ ID NO 42
<211> LENGTH: 20
<212> TYPE: DNA
<213> ORGANISM: Artificial
<220> FEATURE:
<223> OTHER INFORMATION: oligonucleotide primer

<400> SEQUENCE: 42
cgtaaccacc cacaagatcg                                                 20

<210> SEQ ID NO 43
<211> LENGTH: 20
<212> TYPE: DNA
<213> ORGANISM: Artificial
<220> FEATURE:

<223> OTHER INFORMATION: oligonucleotide primer

<400> SEQUENCE: 43
gggcgtattc aggtacttcg                                          20

<210> SEQ ID NO 44
<211> LENGTH: 18
<212> TYPE: DNA
<213> ORGANISM: Artificial
<220> FEATURE:
<223> OTHER INFORMATION: oligonucleotide primer

<400> SEQUENCE: 44
gcgataccgg ctgatgac                                            18

<210> SEQ ID NO 45
<211> LENGTH: 18
<212> TYPE: DNA
<213> ORGANISM: Artificial
<220> FEATURE:
<223> OTHER INFORMATION: oligonucleotide primer

<400> SEQUENCE: 45
cacgccagac caagacga                                            18

<210> SEQ ID NO 46
<211> LENGTH: 19
<212> TYPE: DNA
<213> ORGANISM: Artificial
<220> FEATURE:
<223> OTHER INFORMATION: oligonucleotide primer

<400> SEQUENCE: 46
gcaggagatc catcaggaa                                           19

<210> SEQ ID NO 47
<211> LENGTH: 18
<212> TYPE: DNA
<213> ORGANISM: Artificial
<220> FEATURE:
<223> OTHER INFORMATION: oligonucleotide primer

<400> SEQUENCE: 47
aggtcttcac cggcaagc                                            18

<210> SEQ ID NO 48
<211> LENGTH: 20
<212> TYPE: DNA
<213> ORGANISM: Artificial
<220> FEATURE:
<223> OTHER INFORMATION: oligonucleotide primer

<400> SEQUENCE: 48
tacgtgtggt ggtgatgtcc                                          20

<210> SEQ ID NO 49
<211> LENGTH: 18
<212> TYPE: DNA
<213> ORGANISM: Artificial
<220> FEATURE:
<223> OTHER INFORMATION: oligonucleotide primer

<400> SEQUENCE: 49
cggcggtgtt cttactgc                                            18

```
<210> SEQ ID NO 50
<211> LENGTH: 19
<212> TYPE: DNA
<213> ORGANISM: Artificial
<220> FEATURE:
<223> OTHER INFORMATION: oligonucleotide primer

<400> SEQUENCE: 50
gcgataaggt ccgtggtgt                                                  19

<210> SEQ ID NO 51
<211> LENGTH: 20
<212> TYPE: DNA
<213> ORGANISM: Artificial
<220> FEATURE:
<223> OTHER INFORMATION: oligonucleotide primer

<400> SEQUENCE: 51
gcccgaagtt gtttctgagt                                                 20

<210> SEQ ID NO 52
<211> LENGTH: 21
<212> TYPE: DNA
<213> ORGANISM: Artificial
<220> FEATURE:
<223> OTHER INFORMATION: oligonucleotide primer

<400> SEQUENCE: 52
tcatccgaga tcacacaaac a                                               21

<210> SEQ ID NO 53
<211> LENGTH: 18
<212> TYPE: DNA
<213> ORGANISM: Artificial
<220> FEATURE:
<223> OTHER INFORMATION: oligonucleotide primer

<400> SEQUENCE: 53
cgagagacgc accgattt                                                   18

<210> SEQ ID NO 54
<211> LENGTH: 20
<212> TYPE: DNA
<213> ORGANISM: Artificial
<220> FEATURE:
<223> OTHER INFORMATION: oligonucleotide primer

<400> SEQUENCE: 54
cagaccctga cacctccgta                                                 20

<210> SEQ ID NO 55
<211> LENGTH: 19
<212> TYPE: DNA
<213> ORGANISM: Artificial
<220> FEATURE:
<223> OTHER INFORMATION: oligonucleotide primer

<400> SEQUENCE: 55
agagtgcgcc gattttctt                                                  19

<210> SEQ ID NO 56
<211> LENGTH: 18
<212> TYPE: DNA
<213> ORGANISM: Artificial
<220> FEATURE:
<223> OTHER INFORMATION: oligonucleotide primer
```

```
<400> SEQUENCE: 56
gtagccccgc gtgaagtc                                                      18

<210> SEQ ID NO 57
<211> LENGTH: 20
<212> TYPE: DNA
<213> ORGANISM: Artificial
<220> FEATURE:
<223> OTHER INFORMATION: oligonucleotide primer

<400> SEQUENCE: 57
ggggtggtca actacgtctc                                                    20

<210> SEQ ID NO 58
<211> LENGTH: 20
<212> TYPE: DNA
<213> ORGANISM: Artificial
<220> FEATURE:
<223> OTHER INFORMATION: oligonucleotide primer

<400> SEQUENCE: 58
ggtgagagtc gtgttctggt                                                    20

<210> SEQ ID NO 59
<211> LENGTH: 19
<212> TYPE: DNA
<213> ORGANISM: Artificial
<220> FEATURE:
<223> OTHER INFORMATION: oligonucleotide primer

<400> SEQUENCE: 59
gtaggccagc tccatctcc                                                     19

<210> SEQ ID NO 60
<211> LENGTH: 18
<212> TYPE: DNA
<213> ORGANISM: Artificial
<220> FEATURE:
<223> OTHER INFORMATION: oligonucleotide primer

<400> SEQUENCE: 60
acggtcttga gtgcttcg                                                      18

<210> SEQ ID NO 61
<211> LENGTH: 19
<212> TYPE: DNA
<213> ORGANISM: Artificial
<220> FEATURE:
<223> OTHER INFORMATION: oligonucleotide primer

<400> SEQUENCE: 61
tcgaaatcgc atcggtaga                                                     19

<210> SEQ ID NO 62
<211> LENGTH: 19
<212> TYPE: DNA
<213> ORGANISM: Artificial
<220> FEATURE:
<223> OTHER INFORMATION: oligonucleotide primer

<400> SEQUENCE: 62
gtacaagccg gagggtgtc                                                     19

<210> SEQ ID NO 63
<211> LENGTH: 18
```

<212> TYPE: DNA
<213> ORGANISM: Artificial
<220> FEATURE:
<223> OTHER INFORMATION: oligonucleotide primer

<400> SEQUENCE: 63
cttgagcccc caggttcc                                                 18

<210> SEQ ID NO 64
<211> LENGTH: 20
<212> TYPE: DNA
<213> ORGANISM: Artificial
<220> FEATURE:
<223> OTHER INFORMATION: oligonucleotide primer

<400> SEQUENCE: 64
cagcgaccgt gtgttcttac                                               20

<210> SEQ ID NO 65
<211> LENGTH: 18
<212> TYPE: DNA
<213> ORGANISM: Artificial
<220> FEATURE:
<223> OTHER INFORMATION: oligonucleotide primer

<400> SEQUENCE: 65
ggaagtgggc ggtatcct                                                 18

<210> SEQ ID NO 66
<211> LENGTH: 20
<212> TYPE: DNA
<213> ORGANISM: Artificial
<220> FEATURE:
<223> OTHER INFORMATION: oligonucleotide primer

<400> SEQUENCE: 66
tcgaatatgc agtgttaccg                                               20

<210> SEQ ID NO 67
<211> LENGTH: 20
<212> TYPE: DNA
<213> ORGANISM: Artificial
<220> FEATURE:
<223> OTHER INFORMATION: oligonucleotide primer

<400> SEQUENCE: 67
ttccacatca gagggagtcg                                               20

<210> SEQ ID NO 68
<211> LENGTH: 19
<212> TYPE: DNA
<213> ORGANISM: Artificial
<220> FEATURE:
<223> OTHER INFORMATION: oligonucleotide primer

<400> SEQUENCE: 68
tgagcgccag acaaagtgt                                                19

<210> SEQ ID NO 69
<211> LENGTH: 20
<212> TYPE: DNA
<213> ORGANISM: Artificial
<220> FEATURE:
<223> OTHER INFORMATION: oligonucleotide primer

<400> SEQUENCE: 69
ggccaaaaga cctaagacca                              20

<210> SEQ ID NO 70
<211> LENGTH: 20
<212> TYPE: DNA
<213> ORGANISM: Artificial
<220> FEATURE:
<223> OTHER INFORMATION: oligonucleotide primer

<400> SEQUENCE: 70
tctgtgggtc agggtcttct                              20

<210> SEQ ID NO 71
<211> LENGTH: 20
<212> TYPE: DNA
<213> ORGANISM: Artificial
<220> FEATURE:
<223> OTHER INFORMATION: oligonucleotide primer

<400> SEQUENCE: 71
gagacgaaac accagtcacg                              20

<210> SEQ ID NO 72
<211> LENGTH: 18
<212> TYPE: DNA
<213> ORGANISM: Artificial
<220> FEATURE:
<223> OTHER INFORMATION: oligonucleotide primer

<400> SEQUENCE: 72
cgtcgcattg aggattgg                                18

<210> SEQ ID NO 73
<211> LENGTH: 19
<212> TYPE: DNA
<213> ORGANISM: Artificial
<220> FEATURE:
<223> OTHER INFORMATION: oligonucleotide primer

<400> SEQUENCE: 73
gccgttgttg ctcggatag                               19

<210> SEQ ID NO 74
<211> LENGTH: 19
<212> TYPE: DNA
<213> ORGANISM: Artificial
<220> FEATURE:
<223> OTHER INFORMATION: oligonucleotide primer

<400> SEQUENCE: 74
gatgggccgt atcctcgta                               19

<210> SEQ ID NO 75
<211> LENGTH: 23
<212> TYPE: DNA
<213> ORGANISM: Artificial
<220> FEATURE:
<223> OTHER INFORMATION: oligonucleotide primer

<400> SEQUENCE: 75
ggatctatta ccgacaacca tgt                          23

<210> SEQ ID NO 76
<211> LENGTH: 18
<212> TYPE: DNA
<213> ORGANISM: Artificial

```
<220> FEATURE:
<223> OTHER INFORMATION: oligonucleotide primer

<400> SEQUENCE: 76
gatccccttg gtcgttgc                                                 18

<210> SEQ ID NO 77
<211> LENGTH: 20
<212> TYPE: DNA
<213> ORGANISM: Artificial
<220> FEATURE:
<223> OTHER INFORMATION: oligonucleotide primer

<400> SEQUENCE: 77
ccagtgctac acaaaccaca                                               20

<210> SEQ ID NO 78
<211> LENGTH: 20
<212> TYPE: DNA
<213> ORGANISM: Artificial
<220> FEATURE:
<223> OTHER INFORMATION: oligonucleotide primer

<400> SEQUENCE: 78
gccattctta gcctcacgac                                               20

<210> SEQ ID NO 79
<211> LENGTH: 18
<212> TYPE: DNA
<213> ORGANISM: Artificial
<220> FEATURE:
<223> OTHER INFORMATION: oligonucleotide primer

<400> SEQUENCE: 79
ctggttgctc gcgtcttc                                                 18

<210> SEQ ID NO 80
<211> LENGTH: 20
<212> TYPE: DNA
<213> ORGANISM: Artificial
<220> FEATURE:
<223> OTHER INFORMATION: oligonucleotide primer

<400> SEQUENCE: 80
ctgttcgacg ccagctacac                                               20

<210> SEQ ID NO 81
<211> LENGTH: 19
<212> TYPE: DNA
<213> ORGANISM: Artificial
<220> FEATURE:
<223> OTHER INFORMATION: oligonucleotide primer

<400> SEQUENCE: 81
ggccacccga tagaagttg                                                19

<210> SEQ ID NO 82
<211> LENGTH: 19
<212> TYPE: DNA
<213> ORGANISM: Artificial
<220> FEATURE:
<223> OTHER INFORMATION: oligonucleotide primer

<400> SEQUENCE: 82
ggtggccttg atgtttcag                                                19
```

<210> SEQ ID NO 83
<211> LENGTH: 20
<212> TYPE: DNA
<213> ORGANISM: Artificial
<220> FEATURE:
<223> OTHER INFORMATION: oligonucleotide primer

<400> SEQUENCE: 83
agctgatgag gacggttgtc                                           20

<210> SEQ ID NO 84
<211> LENGTH: 19
<212> TYPE: DNA
<213> ORGANISM: Artificial
<220> FEATURE:
<223> OTHER INFORMATION: oligonucleotide primer

<400> SEQUENCE: 84
cgccacagag tcaacaacc                                            19

<210> SEQ ID NO 85
<211> LENGTH: 19
<212> TYPE: DNA
<213> ORGANISM: Artificial
<220> FEATURE:
<223> OTHER INFORMATION: oligonucleotide primer

<400> SEQUENCE: 85
cgagatcgct gtcaagcac                                            19

<210> SEQ ID NO 86
<211> LENGTH: 20
<212> TYPE: DNA
<213> ORGANISM: Artificial
<220> FEATURE:
<223> OTHER INFORMATION: oligonucleotide primer

<400> SEQUENCE: 86
agcggacgac tgacttgttg                                           20

<210> SEQ ID NO 87
<211> LENGTH: 18
<212> TYPE: DNA
<213> ORGANISM: Artificial
<220> FEATURE:
<223> OTHER INFORMATION: oligonucleotide primer

<400> SEQUENCE: 87
tcttcgtgca ggcgatca                                             18

<210> SEQ ID NO 88
<211> LENGTH: 21
<212> TYPE: DNA
<213> ORGANISM: Artificial
<220> FEATURE:
<223> OTHER INFORMATION: oligonucleotide primer

<400> SEQUENCE: 88
tttcgctgac gtaatagacg a                                         21

<210> SEQ ID NO 89
<211> LENGTH: 18
<212> TYPE: DNA
<213> ORGANISM: Artificial
<220> FEATURE:
<223> OTHER INFORMATION: oligonucleotide primer

<400> SEQUENCE: 89
ggatcttcgg cctggaat                                                          18

<210> SEQ ID NO 90
<211> LENGTH: 20
<212> TYPE: DNA
<213> ORGANISM: Artificial
<220> FEATURE:
<223> OTHER INFORMATION: oligonucleotide primer

<400> SEQUENCE: 90
acggcaactc ataggtcagc                                                        20

<210> SEQ ID NO 91
<211> LENGTH: 18
<212> TYPE: DNA
<213> ORGANISM: Artificial
<220> FEATURE:
<223> OTHER INFORMATION: oligonucleotide primer

<400> SEQUENCE: 91
gaagggaagg ggagagca                                                          18

<210> SEQ ID NO 92
<211> LENGTH: 116
<212> TYPE: DNA
<213> ORGANISM: Artificial
<220> FEATURE:
<223> OTHER INFORMATION: oligonucleotide probe

<400> SEQUENCE: 92
cgtggtgtag tagtcagcca gaacacgggc ggccatcagg ccggcgatgc ttcccccag             60 aacgactgcg gtttcgccga attcaggcac actgagtctc cttctgatcc gttttt               116

<210> SEQ ID NO 93
<211> LENGTH: 169
<212> TYPE: DNA
<213> ORGANISM: Artificial
<220> FEATURE:
<223> OTHER INFORMATION: oligonucleotide probe

<400> SEQUENCE: 93
gcgaacttgg ggaatgtgcg gactggggcc atgggcact ccgcggcggg ccactgggcg             60
ttcgggcaga acgtctcgtt ccaccacggt caccgtggtg tagtagtcag ccagaacacg           120
ggcggccatc aggccggcga tgcttccccc cagaacgact gcggtttcg                       169

<210> SEQ ID NO 94
<211> LENGTH: 165
<212> TYPE: DNA
<213> ORGANISM: Artificial
<220> FEATURE:
<223> OTHER INFORMATION: oligonucleotide probe

<400> SEQUENCE: 94
ggccatcatc agcaagaccg tggcgaggcc gtgcaggaca agttgtcgca aaacgacatc            60
ccggccaagc gagtcgtcca attcggtcga ccgcgaataa tccgggatca caaagcgata          120
gcgctctgag ccgaatctcg ttctcgtgct tcggtgtgtg ttcat                           165

<210> SEQ ID NO 95
<211> LENGTH: 200
<212> TYPE: DNA

```
<213> ORGANISM: Artificial
<220> FEATURE:
<223> OTHER INFORMATION: oligonucleotide probe

<400> SEQUENCE: 95
gcgaacgaca tccagattcg cgataggtca ccgtccttcc acactcgcgc tcccatcgcc      60
accaactcat cgaggagccc ggggaacagc tcctccatgg tctgcgtggc gcgaacttgg     120
ggaatgtgcg gactgggcc atggggcact ccgcggcggg ccactgggcg ttcgggcaga     180
acgtctcgtt ccaccacggt                                                 200

<210> SEQ ID NO 96
<211> LENGTH: 166
<212> TYPE: DNA
<213> ORGANISM: Artificial
<220> FEATURE:
<223> OTHER INFORMATION: oligonucleotide probe

<400> SEQUENCE: 96
gcctcagatc ctcctcagtg agcacggcct ccagcgggcc tgattcatca gatgaacccg      60
gcgtagttct gccgtctggt gcataagccc acaccagccc tgggtcagat tgcaccgcaa     120
catctttgat gtcggcgctt aaccgactta ttccatgaac gctcgc                    166

<210> SEQ ID NO 97
<211> LENGTH: 145
<212> TYPE: DNA
<213> ORGANISM: Artificial
<220> FEATURE:
<223> OTHER INFORMATION: oligonucleotide probe

<400> SEQUENCE: 97
gacgcgctgg taaagaacag cggcggggtg gacctgatca ccggaccagg ctcgagtttg      60
ccaggcccac cggcggccag gtgtgctcga agacccgata acgccatcgg ccgcggccca     120
ctggcagacc ctgacacctc cgtag                                           145

<210> SEQ ID NO 98
<211> LENGTH: 170
<212> TYPE: DNA
<213> ORGANISM: Artificial
<220> FEATURE:
<223> OTHER INFORMATION: oligonucleotide probe

<400> SEQUENCE: 98
agagcgcggc agtgagttga ccgacatccg gcgtgagcat gtccgttcga tcgagccaaa      60
gctcgtcccg agcgtggcgg ccggtaccga gcggttgcaa gtcgaagtcg cctaccagcc     120
cgccgatgtc agcagcgagg cgaccgcgac ggtgatgctc ggaatgtatc                170

<210> SEQ ID NO 99
<211> LENGTH: 149
<212> TYPE: DNA
<213> ORGANISM: Artificial
<220> FEATURE:
<223> OTHER INFORMATION: oligonucleotide probe

<400> SEQUENCE: 99
atacatggcg accttgctgt tccccctaat cgcgatcgcc atgattggcg caggatgtgc      60
acccggtaat ccggcgtggc tgtggtacgg cggggccatt ctgctggcca tctctgcctt     120
attggtggga gtctccctct ggatctggc                                       149
```

<210> SEQ ID NO 100
<211> LENGTH: 166
<212> TYPE: DNA
<213> ORGANISM: Artificial
<220> FEATURE:
<223> OTHER INFORMATION: oligonucleotide probe

<400> SEQUENCE: 100

```
ggcgtcggca tcatttatgg gagcggccgc cgaattttcg gcgccggggt caggcggacc      60
gggcaggaga ttgtctgccg ctatcttccg tggtacgaga gcaacccata catggcgacc     120
ttgctgttcc ccctaatcgc gatcgccatg attggcgcag gatgtg                   166
```

<210> SEQ ID NO 101
<211> LENGTH: 182
<212> TYPE: DNA
<213> ORGANISM: Artificial
<220> FEATURE:
<223> OTHER INFORMATION: oligonucleotide probe

<400> SEQUENCE: 101

```
ctcccaccaa taaggcagag atggccagca gaatggcccc gccgtaccac agccacgccg      60
gattaccggg tgcacatcct gcgccaatca tggcgatcgc gattaggggg aacagcaagg     120
tcgccatgta tgggttgctc tcgtaccacg gaagatagcg gcagacaatc tcctgcccgg     180
tc                                                                   182
```

<210> SEQ ID NO 102
<211> LENGTH: 115
<212> TYPE: DNA
<213> ORGANISM: Artificial
<220> FEATURE:
<223> OTHER INFORMATION: oligonucleotide probe

<400> SEQUENCE: 102

```
gcgcctgaaa ccgaagtcgc cccgcagcgg gtatgtcgat ggagcgtggt ggccgcatag      60
tgacgacctg acggcggagc tgccagatct gctggcagtg ctatcggttc ggctt          115
```

<210> SEQ ID NO 103
<211> LENGTH: 157
<212> TYPE: DNA
<213> ORGANISM: Artificial
<220> FEATURE:
<223> OTHER INFORMATION: oligonucleotide probe

<400> SEQUENCE: 103

```
cagagaatca ccctcctggt ggtttcaccg cacaccgacg aaaacgatgc gcacaccgtc      60
atgatgaccg cggccggccc gaacaacgcc ttgacggtcg cgaacctcat gatcagcggg     120
caaaaagtgg acgcccgcga gtagaccatg tcggcca                             157
```

<210> SEQ ID NO 104
<211> LENGTH: 137
<212> TYPE: DNA
<213> ORGANISM: Artificial
<220> FEATURE:
<223> OTHER INFORMATION: oligonucleotide probe

<400> SEQUENCE: 104

```
ccgtgggctt gttttgagcg gctatcaccg agtggaagac gctgatgagt ccgaaggctt      60
tgagaactca tgtagcctcg ggtatcgacc aacccacgag ccgatcaggc aggtgctctc     120
acacagatga tacggcc                                                   137
```

<210> SEQ ID NO 105
<211> LENGTH: 128
<212> TYPE: DNA
<213> ORGANISM: Artificial
<220> FEATURE:
<223> OTHER INFORMATION: oligonucleotide probe

<400> SEQUENCE: 105
cgtaaccacc cacaagatcg gacgtgaccc cttttgccgc ggttcgtaaa cccgccctgt      60
ccgcatgcct ccgctcagcc cgaatctcac tgattccatg gcgattaccg aagtacctga     120
atacgccc                                                              128

<210> SEQ ID NO 106
<211> LENGTH: 170
<212> TYPE: DNA
<213> ORGANISM: Artificial
<220> FEATURE:
<223> OTHER INFORMATION: oligonucleotide probe

<400> SEQUENCE: 106
gcgataccgg ctgatgacat cgacgcgctc gctgaccgga cggttcgccc agtcggcctg      60
cgccgcgcgc gcctcggcga aggcggcttc gacgtcttcg gccgtgccga cggggatggt     120
ggtcagcggc ttgccggtga agacctcgtc gatcgtcttg gtctggcgtg                170

<210> SEQ ID NO 107
<211> LENGTH: 189
<212> TYPE: DNA
<213> ORGANISM: Artificial
<220> FEATURE:
<223> OTHER INFORMATION: oligonucleotide probe

<400> SEQUENCE: 107
gcaggagatc catcaggaac tcgcggttct cgacgaccag gtcgcgatac cggctgatga      60
catcgacgcg ctcgctgacc ggacggttcg cccagtcggc ctgcgccgcg cgcgcctcgg     120
cgaaggcggc ttcgacgtct tcggccgtgc cgacgggat ggtggtcagc ggcttgccgg     180
tgaagacct                                                             189

<210> SEQ ID NO 108
<211> LENGTH: 126
<212> TYPE: DNA
<213> ORGANISM: Artificial
<220> FEATURE:
<223> OTHER INFORMATION: oligonucleotide probe

<400> SEQUENCE: 108
tacgtgtggt ggtgatgtcc gctcaggggc atggcgataa ggtccgtggt gtcgacggcc      60
ggacccacca attcgtatgc cgatttgttt tcgaaccgcc agatcgctgc agtaagaaca     120
ccgccg                                                                126

<210> SEQ ID NO 109
<211> LENGTH: 150
<212> TYPE: DNA
<213> ORGANISM: Artificial
<220> FEATURE:
<223> OTHER INFORMATION: oligonucleotide probe

<400> SEQUENCE: 109
gcgataaggt ccgtggtgtc gacggccgga cccaccaatt cgtatgccga tttgttttcg      60
aaccgccaga tcgctgcagt aagaacaccg ccggagccgg tgatgcgttg tccgggcttg     120
aagcccaggc actcagaaac aacttcgggc 150

<210> SEQ ID NO 110
<211> LENGTH: 130
<212> TYPE: DNA
<213> ORGANISM: Artificial
<220> FEATURE:
<223> OTHER INFORMATION: oligonucleotide probe

<400> SEQUENCE: 110
tcatccgaga tcacacaaac aagtctcgac tcggtgtcgg gccttcagcc accgatgatg 60
ggacacgttt cccacagata gcgacatcgt ccggctacgc acgacattcc cgaaatcggt 120
gcgtctctcg 130

<210> SEQ ID NO 111
<211> LENGTH: 139
<212> TYPE: DNA
<213> ORGANISM: Artificial
<220> FEATURE:
<223> OTHER INFORMATION: oligonucleotide probe

<400> SEQUENCE: 111
cagaccctga cacctccgta gacccagtg cgctgaaccc caagaactga gttgattccg 60
cgaaaccacg gcagcgcggt gtgaatccag gtattgcggt tgatgtcctc gtcgatggtg 120
aagaaaatcg gcgcactct 139

<210> SEQ ID NO 112
<211> LENGTH: 168
<212> TYPE: DNA
<213> ORGANISM: Artificial
<220> FEATURE:
<223> OTHER INFORMATION: oligonucleotide probe

<400> SEQUENCE: 112
gtagccccgc gtgaagtctg acggtgtcga cccacccggc ttgccgtatt ggtagttact 60
gacaatcacc aaacccgcag ctgtcagtga gtcggcgtag gaccgagtga tgggcttggc 120
gccgaacgag gagccggggc gtgacaacga gacgtagttg accaccccc 168

<210> SEQ ID NO 113
<211> LENGTH: 138
<212> TYPE: DNA
<213> ORGANISM: Artificial
<220> FEATURE:
<223> OTHER INFORMATION: oligonucleotide probe

<400> SEQUENCE: 113
ggtgagagtc gtgttctggt acttcatgga gagccgggtg tcggtaagac ggccttgctg 60
gactacgtcg gtgaacgggc cgccggctgt cgcgtcatcc gtgccagcgg ggtcgagtcg 120
gagatggagc tggcctac 138

<210> SEQ ID NO 114
<211> LENGTH: 172
<212> TYPE: DNA
<213> ORGANISM: Artificial
<220> FEATURE:
<223> OTHER INFORMATION: oligonucleotide probe

<400> SEQUENCE: 114
acggtcttga gtgcttcgat gagagcggga tcgatcggcc gcccgatcag tgtgtcaccg 60

```
cccgcgacca tgacggtgtc gacggattcg agggccgaga ggggacacgt cacagcgaat    120
cgggtgccga tcgacgtggt cacatcgcgt ccgtctaccg atgcgatttc ga            172

<210> SEQ ID NO 115
<211> LENGTH: 148
<212> TYPE: DNA
<213> ORGANISM: Artificial
<220> FEATURE:
<223> OTHER INFORMATION: oligonucleotide probe

<400> SEQUENCE: 115
gtacaagccg gagggtgtca caacgtgtgg atcggcgaca tgaacggcga tcacctgaga    60
aacgctgccg gataagtggc ggcgtgcgcg acgctggact cacactgcga caaagaaatt   120
caccgggggc ggaacctggg ggctcaag                                      148

<210> SEQ ID NO 116
<211> LENGTH: 131
<212> TYPE: DNA
<213> ORGANISM: Artificial
<220> FEATURE:
<223> OTHER INFORMATION: oligonucleotide probe

<400> SEQUENCE: 116
cagcgaccgt gtgttcttac accgcgattt tcatcccggc aacatcttgt ggcagcaagg    60
caaaatatcc ggacttgtcg actgggtctc gtcgtgcgcc ggacccgtcc aggaggatac   120
cgcccacttc c                                                        131

<210> SEQ ID NO 117
<211> LENGTH: 113
<212> TYPE: DNA
<213> ORGANISM: Artificial
<220> FEATURE:
<223> OTHER INFORMATION: oligonucleotide probe

<400> SEQUENCE: 117
tcgaatatgc agtgttaccg ggaatccgga cggttccgcg atcgcacgtc gcggttaccg    60
ttggtggcct gaggcaagct ttggccatga catcgactcc ctctgatgtg aa           113

<210> SEQ ID NO 118
<211> LENGTH: 184
<212> TYPE: DNA
<213> ORGANISM: Artificial
<220> FEATURE:
<223> OTHER INFORMATION: oligonucleotide probe

<400> SEQUENCE: 118
tgagcgccag acaaagtgtc aggtcattgc gcagcggccg ttggaaggcg gccagtccgc    60
ggcgattcac cgccttgttc tcgatgaccg aagcgctgtg atcctgcagc gattcgtctt   120
ggattggatc cgcgacgagc cgtgggctcc tgcgaacgag gtactggtct taggtctttt   180
ggcc                                                                184

<210> SEQ ID NO 119
<211> LENGTH: 169
<212> TYPE: DNA
<213> ORGANISM: Artificial
<220> FEATURE:
<223> OTHER INFORMATION: oligonucleotide probe

<400> SEQUENCE: 119
tctgtgggtc agggtcttct ggatcggtcg tcgccggtcg gctttcggag aatccggacg    60
```

```
ttacggtgct tttgctcgag gccggtgaaa ccgatgatgt tcggcagtc cacgatccca      120 cgcagtggcc gctgaacttg ggtagcgagc gtgactggtg tttcgtctc                 169

<210> SEQ ID NO 120
<211> LENGTH: 156
<212> TYPE: DNA
<213> ORGANISM: Artificial
<220> FEATURE:
<223> OTHER INFORMATION: oligonucleotide probe

<400> SEQUENCE: 120
cgtcgcattg aggattggca cgggccggca gtctccgccc gcggcaccgg gggcccatg       60 tccgtgacgt ccccgcccga ccccaatccg atcgctccgg ccatcgtcga ggccgctcgc    120
tcgctgggga tcccgagcta tccgagcaac aacggc                              156

<210> SEQ ID NO 121
<211> LENGTH: 185
<212> TYPE: DNA
<213> ORGANISM: Artificial
<220> FEATURE:
<223> OTHER INFORMATION: oligonucleotide probe

<400> SEQUENCE: 121
gatgggccgt atcctcgtac ggattcgtcg atcccgcggc atgtggtttg tgtagcactg      60
gcgcgcatcc tcctaacaac acggcgacga ccactagcga actgatcagc gcttggcgca    120
acggcatacg ttgttcctca atggtggtgt tgagcatcga aaacatggtt gtcggtaata    180
gatcc                                                                185

<210> SEQ ID NO 122
<211> LENGTH: 184
<212> TYPE: DNA
<213> ORGANISM: Artificial
<220> FEATURE:
<223> OTHER INFORMATION: oligonucleotide probe

<400> SEQUENCE: 122
gatccccttg gtcgttgcac gaggcgaacg agaatgcccc gctgacgccc tccagcttcg      60
cggcggcgac gatctgcttg gccggctcga tcacctgcgc cttggtctga tcgtcgctca    120
tgggatgggc cgtatcctcg tacggattcg tcgatcccgc ggcatgtggt ttgtgtagca    180
ctgg                                                                 184

<210> SEQ ID NO 123
<211> LENGTH: 136
<212> TYPE: DNA
<213> ORGANISM: Artificial
<220> FEATURE:
<223> OTHER INFORMATION: oligonucleotide probe

<400> SEQUENCE: 123
gccattctta gcctcacgac cacagaaggc tagccgcacg acggccgatg gtcgcggcct      60
tcaggaaaag aacctggcca taagggcttc tgcgaacggg cgatgcgtgg tgttttgcga    120
agacgcgagc aaccag                                                    136

<210> SEQ ID NO 124
<211> LENGTH: 147
<212> TYPE: DNA
<213> ORGANISM: Artificial
<220> FEATURE:
```

<223> OTHER INFORMATION: oligonucleotide probe

<400> SEQUENCE: 124

```
ctgttcgacg ccagctacac ccgctggggc ccgatccagt gggtgccgcc ggaaaccttt      60
gtgacactcg gtgagcacct gcggggaagg ggatggaacg gtcgtgacat ccacgcggtc     120
ctcggtggca acttctatcg ggtggcc                                         147
```

<210> SEQ ID NO 125
<211> LENGTH: 174
<212> TYPE: DNA
<213> ORGANISM: Artificial
<220> FEATURE:
<223> OTHER INFORMATION: oligonucleotide probe

<400> SEQUENCE: 125

```
ggtggccttg atgtttcagg aaccggcact gttcccatgg ctgacgtcgg ccgccaacgt      60
cgagttggcc ttgcgggcgc gctcggtgcc gcgcccgcaa cgccgccagc ggacgactga     120
cttgttgcaa acggtcggct tggctgactt tgccgacaac cgtcctcatc agct           174
```

<210> SEQ ID NO 126
<211> LENGTH: 101
<212> TYPE: DNA
<213> ORGANISM: Artificial
<220> FEATURE:
<223> OTHER INFORMATION: oligonucleotide probe

<400> SEQUENCE: 126

```
cgccacagag tcaacaaccc gggcgttgcc gaattggcct cccgcatctc cacccagcta      60
cggaacgagg gaaaccgtgg cggtgcttga cagcgatctc g                         101
```

<210> SEQ ID NO 127
<211> LENGTH: 190
<212> TYPE: DNA
<213> ORGANISM: Artificial
<220> FEATURE:
<223> OTHER INFORMATION: oligonucleotide probe

<400> SEQUENCE: 127

```
agcggacgac tgacttgttg caaacggtcg gcttggctga ctttgccgac aaccgtcctc      60
atcagctgtc cggtggcatg cagcagcgcg tcgcattggc gcgtgcgctc gcccaagacg     120
ccgacgtctt gctgatggac gagccgttcg gggcgctgga tgccctgacc cgtgatcgcc     180
tgcacgaaga                                                            190
```

<210> SEQ ID NO 128
<211> LENGTH: 174
<212> TYPE: DNA
<213> ORGANISM: Artificial
<220> FEATURE:
<223> OTHER INFORMATION: oligonucleotide probe

<400> SEQUENCE: 128

```
tttcgctgac gtaatagacg agggtcccgg tgagcagcac cgcgacgccg aagaacgtca      60
gccaaagaca cttgatccgc gactcgtcgg gtaaatcctt gcgcaacaaa cgaagccaca     120
cgatggtgag catgatgccg acgagcactg cgccgaattc caggccgaag atcc           174
```

<210> SEQ ID NO 129
<211> LENGTH: 104
<212> TYPE: DNA
<213> ORGANISM: Artificial

```
<220> FEATURE:
<223> OTHER INFORMATION: oligonucleotide probe

<400> SEQUENCE: 129
acggcaactc ataggtcagc tggcttcccg ccgtcagagg gatgtagatc agtgtcagct    60
cggccgcaag ctgcagacgg gatcgctgct ctccccttcc cttc                   104
```

PRIMER AND PROBE FOR DETECTION OF *MYCOBACTERIUM INTRACELLULARE*, AND METHOD FOR DETECTION OF *MYCOBACTERIUM INTRACELLULARE* USING THE PRIMER OR THE PROBE

RELATED APPLICATION

This application is the national stage of International Application No. PCT/JP2009/059593, filed May 26, 2009, which claims the benefit of Japanese Application No. JP2008/139105, filed May 28, 2008, which are both incorporated herein by reference.

TECHNICAL FIELD

The present invention relates to a method for detecting and/or identifying *Mycobacterium intracellulare* (hereinafter, optionally abbreviated as *M. intracellulare*) through the use of amplification of nucleic acid and detection system thereof.

BACKGROUND ART

In the following document of the present description, when nucleic-acid base is indicated, A represents adenine; C represents cytosine; G represents guanine; T represents thymine and U represents uracil; respectively. In addition, when "oligonucleotide" is mentioned, it includes "polynucleotide" in some cases.

Nontuberculous mycobacteria is a gram positive *bacillus* having acid-fast characteristics classified into genus *Mycobacterium* (hereinafter, optionally abbreviated simply as M.), and is a kind of acid-fast bacterium other than tuberculosis complex and *Mycobacterium leprae*. Fifteen to 20% of cases showing positive for sputum smear examination for acid-fast bacterium have been diagnosed thereafter to be nontuberculous mycobacterium by the test for the identification of bacterial species.

Among nontuberculous mycobacteria, clinically problematic bacterial species are known to be *M. intracellulare, Mycobacterium kansasii, Mycobacterium marinum, Mycobacterium gordonae, Mycobacterium szulgai, Mycobacterium avium, Mycobacterium xenopi, Mycobacterium fortuitum, Mycobacterium chelonei, Mycobacterium abscessus*, and so on.

Above all, the commonly noted strains are *M. intracellulare* and *M. avium*. Since *M. intracellulare* and *M. avium* are closely resemble each other and difficult to distinguish between them, *M. intracellulare* and *M. avium* have been referred to collectively as *Mycobacterium avium* complex (MAC). About 70% of patients with nontuberculous mycobacterial disease are MAC infection, and the second large population is *M. kansasii* infection accounting 20%. And the rest of 10% are the infection by other bacterial species.

In general, since the nontuberculous mycobacteria have weak toxicity, they are believed to be harmless to a healthy subject. However, on rare occasions, they may exert infectivity to human. Among them, the MAC is known to cause sometimes aftereffects of tuberculosis (lung infectious disease), or to cause opportunistic infections to a compromised patient such as AIDS patient. Therefore, it is particularly important in the therapy to detect the nontuberculous mycobacterium with rapidity and preciseness.

In addition, in recent years, the incidence of nontuberculous mycobacterial infection demonstrates upward trend, and therefore, development of a method for discriminating tuberculosis bacterium from nontuberculous mycobacterium in a short period of time has been desired strongly. Moreover, from the viewpoint of the fact that the method of detecting/diagnosing *M. intracellulare* and *M. avium* by nucleic acid amplification technology has been included in health insurance coverage, its diagnostic significance is obviously great.

In addition, most of the nontuberculous mycobacteria demonstrate resistance against antituberucular agents. Therefore, when a patient is suspected of acid-fast bacterium infection, differential diagnosis whether the disease is tuberculosis or nontuberculous mycobacterial disease is quite important to decide a course of treatment. Further, as a method for treatment of the diseases caused by nontuberculous mycobacterium may vary depending on the individual species of bacterium, the identification of bacterial species is also quite important. However, nontuberculous mycobacteral diseases do not show any specific clinical symptom. Therefore, it is quite difficult to differentiate tuberculosis from nontuberculous mycobacterial disease by clinical observation and histopathological manifestation, and to specify the species of the nontuberculous mycobacterium. Consequently, the diagnosis whether the disease is tuberculosis or nontuberculous mycobacterial disease has to be carried out by identification of the infected bacterium.

A typical method for the identification of bacterium to be carried out for the diagnosis of nontuberculous mycobacterial disease is sputum smear examination. However, by this test, it can be recognized only whether the pathogenic bacterium is "acid-fast bacterium-positive" or not, and cannot be identified whether the pathogenic bacterium is tuberculosis bacteria or nontuberculous mycobacterium. Therefore, when result of the sputum smear examination is positive, bacterial culture examination by isolation culture on a culture medium such as Ogawa's medium is carried out to differentiate between tuberculosis bacteria and nontuberculous mycobacterium. And further, by performing additional biochemical examinations, bacterial species of the infected bacterium is identified. However, in general, growth of genus *Mycobacterium* is slow; for example, it takes 3 to 4 weeks only for its isolation culture. And further, it requires additional 2 to 3 weeks to obtain results of various biochemical tests for the identification of bacterial species. Accordingly, the conventional basic method, in which a diagnostic outcome on whether the disease is tuberculosis or not is obtained by conducting the above described smear examination and a cell culture assay, is a considerably time-consuming method.

On the other hand, in recent years, a technology of detecting bacteria on a genetic level has been developed. For example, a diagnostic technique utilizing the nucleic acid amplification technology such as polymerase chain reaction (PCR) and the like has been studied as a useful means for detecting bacteria. Because of high sensitivity of this method, even if there are only several cells of the bacteria in a sample, the bacteria can be detected. In addition, this method has an advantage that the detection (identification of bacterial species) can be completed in a short time (in 4 days at the longest). However, in the usual PCR method, the number of bacteria cannot be determined. In addition, in this method, cells are detected regardless of live cells or dead cells. Further, if some bacteria exist in the sample, the determination is made positive regardless of size of the bacterial count. Therefore, by the PCR method, diagnosis of infectivity will be provided with uncertainty. Furthermore, the method has other problems such as that judgment of false positive tends to be made due to too high sensitivity.

With respect to the method for detection of *M. intracellulare* using the PCR method, there is a method for detection of existence or absence of MAC nucleic acid using a multiple primer set of oligonucleotide primer specific for 2 or more of gene regions comprising, for example, MacSequevar gene region, 19 kD protein (MAV 19k) gene region of *M. avium*, and ribosomal protein s1 gene region of *M. intracellulare* (Patent Literature 1). However, by this method, discrimination between *M. intracellulare* and *M. avium* cannot be achieved. In addition, in the PCR using the employed rps1 primer (a primer designed from the ribosomal protein s1 gene region of *M. intracellulare*), even when the isolated strain of *M. avium* is used as a sample, the amplification product has also been detected; there remains a problem in terms of the specificity for *M. intracellulare*.

In addition, a method has also been known, in which PCR is performed by using a primer which is capable of amplifying a DNA nucleotide sequence targeting insertion site of the gene insertion sequence IS901, and determining whether it is avian tuberculosis bacterium (*M. avium*) or *M. intracellulare* based on a chain length of the obtained amplification product (Patent Literature 2). However, in the PCR using the aforementioned primer, the primer extension product can be obtained not only when the sample is avian tuberculosis bacterium (*M. avium*) but also *M. intracellulare*, and therefore, this determination method can not be said as a specific method for *M. intracellulare*. In addition, the method, whereby the discrimination between both bacterial species is carried out based on the chain length of the primer extension product, is cumbersome; and it is conceivable that different determination may be made depending on the judge; and in consequence, the method cannot be said as a reliable determination method.

Other than the PCR method, there is a determination method through the use of Strand Displacement Amplification Method (SDA method). For example, JP-A-10-4984 (Patent Literature 3) discloses a method in which the 63 nucleotide segment of BCG85-B gene coding a part of $\alpha$-antigen of mycobacteria is targeted. In this method, using a primer which is capable of amplifying the target sequence in the BCG85-B gene owned by both *M. intracellulare* and *M. avium*, nucleic acid amplification reaction is performed by the SDA method, and then MAC is detected based on the results. That is, the primer used in the aforementioned method is a primer capable of amplifying both *M. intracellulare* and *M. avium*. However, in this method, as a matter of course, a primer extension product will be obtained in both cases where either of *M. intracellulare* or *M. avium* exists in a sample. Because of this, MAC can be detected by this method; however, it is impossible to detect *M. intracellulare* specifically. In addition, even when MAC is detected, there can be an instance where false-positive result is provided.

In JP-A-2001-103986 (Patent Literature 4), a primer to be used for the detection of MAC and an oligonucleotide to be used as a capture probe and a detection probe have been disclosed. However, the aforementioned primer can amplify a 48 bp target sequence from dnaJ gene which is owned commonly by both *M. intracellulare* and avian tuberculosis bacteria (*M. avium*). Namely, amplification reaction will take place in both cases where either of *M. intracellulare* or *M. avium* is present in a sample. Therefore, if the SDA method is practiced using aforementioned primer, the primer extension product will be detected using the capture probe and detection probe, and based on the results, detection of MAC can be achieved. However, specific detection of *M. intracellulare* is impossible to achieve without detection of *M. avium*.

Beyond that, there is a method of amplification of nucleic acid of *M. intracellulare* through the use of LAMP (Loop-Mediated Isothermal Amplification) method, and the like. However, in the LAMP method, there remains some problems such as that the nucleotide sequence of amplified DNA cannot be determined; that efficient length of DNA to be amplified is limited; and that the method provides false-positive result occasionally; and the like.

To solve these problems, the present inventor have already applied PCT/JP2007/059251 for patent (Patent Literature 6). In this application, a primer and a probe which were developed focusing on the capability of distinguishing/detecting in distinction of *M. intracellulare* from *M. avium* have been disclosed. In addition, by this invention, as compared to the conventional methods, specific and rapid detection of *M. intracellulare* in distinction from other *Mycobacterium* species was enabled.

CITATION LIST

Patent Literature

Patent Literature 1: JP-A-11-69999;
Patent Literature 2: JP-B-3111213;
Patent Literature 3: JP-A-10-4984;
Patent Literature 4: JP-A-2001-103986;
Patent Literature 5: JP-A-2005-204582;
Patent Literature 6: WO 2007/129628.

Non Patent Literature

Non-Patent Literature 1: F. Poly et al., J. Bacteriology, 2004, 186(14), p. 4781-4795.

SUMMARY OF INVENTION

Technical Problem

An object of the present invention is to provide a new primer for detecting *M. intracellulare* which can exclude any false-positive result for the diagnosis; and to provide a method for detecting *M. intracellulare* more simply, rapidly and with high accuracy.

Solution to Problem

The present invention was made for the purpose of solving the above described problems, and comprises the following aspects:

(1) An oligonucleotide comprising a part or the entire of the nucleotide sequence shown in any of SEQ ID NO: 1 to SEQ ID NO: 15 (wherein the characters of A, C, G and T represent adenine, cytosine, guanine and thymine, respectively; and, T at arbitrary position may be replaced by uracil (U); and hereinafter, the same as above), or a part or the entire of the sequence complementary to the nucleotide sequence shown in any of SEQ ID NO: 1 to SEQ ID NO: 15, wherein the oligonucleotide is capable of hybridizing with a nucleotide sequence of *Mycobacterium intracellulare* gene.

(2) A primer for detecting *Mycobacterium intracellulare*, comprising;

an oligonucleotide comprising a part or the entire of the nucleotide sequence shown in any of SEQ ID NO: 1 to SEQ ID NO: 15, or a part or the entire of the sequence complementary to the nucleotide sequence shown in any of SEQ ID NO: 1 to SEQ ID NO: 15,
wherein the oligonucleotide is capable of hybridizing with a nucleotide sequence of *Mycobacterium intracellulare* gene.
(3) A probe for detecting *Mycobacterium intracellulare*, comprising;
an oligonucleotide comprising a part or the entire of the nucleotide sequence shown in any of SEQ ID NO: 1 to SEQ NO: 15, or a part or the entire of the sequence complementary to the nucleotide sequence shown in any of SEQ ID NO: 1 to SEQ ID NO: 15,
wherein the oligonucleotide is capable of hybridizing with the nucleotide sequence to *Mycobacterium intracellulare* gene.
(4) A method for detecting *Mycobacterium intracellulare*, comprising:
using an oligonucleotide comprising a part or the entire of the nucleotide sequence shown in any of SEQ ID NO: 1 to SEQ ID NO: 15, or a part or the entire of the sequence complementary to the nucleotide sequence shown in any of SEQ ID NO: 1 to SEQ ID NO: 15, wherein the oligonucleotide is capable of hybridizing with a nucleotide sequence of *Mycobacterium intracellulare* gene as a primer or/and a probe.
(5) A reagent kit for detecting *Mycobacterium intracellulare*, comprising:
an oligonucleotide comprising a part or the entire of the nucleotide sequence shown in any of SEQ ID NO: 1 to SEQ ID NO: 15, or a part or the entire of the sequence complementary to the nucleotide sequence shown in any of SEQ ID NO: 1 to SEQ ID NO: 15, wherein the oligonucleotide is capable of hybridizing with the nucleotide sequence of *Mycobacterium intracellulare* gene, as a primer or/and a probe.

It has been known that there exist 28 kinds of serotype for *Mycobacterium avium* complex (MAC) consisting of *M. intracellulare* and *M. avium*. Therefore, it is technically quite difficult to specify a DNA region (1) which is a frequently-conserved consensus sequence within the strains of *M. intracellulare*, and (2) which can be used as a marker sequence (target) for distinguishing/identifying only *M. intracellulare* from the closely-related species including *M. avium*.

Therefore, among primer sets known today, by the one which has been followed after specificity (avoidance of false-positive), the consensus sequence among various species of *M. intracellulare* can not be caught. Namely, it is possible to distinguish/identify a specified strain of *M. intracellulare* from the other closely-related species including *M. avium*. However, when the determination is carried out using said primer set, the determination can be made only when a patient is infected with a specified *M. intracellulare* strain which can be detected by the primer set, and can not be made when the patient is infected with other *M. intracellulare* strain.

On the other hand, when the primer set focused on the consensus sequence (avoidance of false-negative) is employed, the specificity for a *M. intracellulare* is conversely low.

Accordingly, at the present time, to determine whether a patient is infected any of *M. intracellulare* of plural serotypes or strains, it is necessary to conduct two-step of operations such that the PCR is carried out using a primer set which is capable of amplifying all acid-fast bacteria; and then, for the obtained amplified DNA fragments, a probe sequence which is specific for *M. intracellulare* is hybridized to detect *M. intracellulare*. These operations were very complicated.

In view of the above described situation, the present inventor has studied intensively, on the basis of the invention involved in the above described patent application, to establish a further superior method for detection of *M. intracellulare*.

As a result, a primer and a probe which are specific for *M. intracellulare*, and which can detect in distinction from other Mycobacterium species, and furthermore, which can detect a sequence region highly conserved within plural strains of *M. intracellulare* were developed. And, it was found that only by performing PCR employing a pair of primer set selected from the developed primers (two-step detection operation described above was unnecessary), the case where any of *M. intracellulare* of plural serotypes or strains exists was detectable, and thus the invention was completed.

Advantageous Effects of Invention

According to the method for detection of *M. intracellulare* using the primer and/or probe of the present invention, *M. intracellulare* can be detected and diagnosed more rapidly and with high accuracy compared to the conventional bacterium identification method by a cell culture assay and the like. In addition, by performing the detection by the method of the present invention, any false-positive result in diagnosis can be eliminated as compared with the diagnosis method by PCR using a conventional primer and/or a probe, and as the results, *M. intracellulare* can be detected and diagnosed with higher accuracy and preciseness in a specific manner. Further, by the use of the detection method of the present invention, *M. intracellulare* cell can also be quantified.

Further, according to the method for detecting *M. intracellulare* using the primer of the present invention, it is possible to detect the case where any of *M. intracellulare* of plural serotypes or strains exists without using two or more of primer set in a single procedure. In addition, advantageous effects such that this makes the detection operation simple and that the time required for diagnosis is cut down can also be obtained.

BRIEF DESCRIPTION OF DRAWINGS

FIG. 1 shows a result of melting curve analysis obtained in Example 2, which is obtained based on the result of the real-time PCR by the intercalator method using Mint 02_T7pa Fw1 and a primer Mint 02_T7pa Rv1, and using respective DNA sample derived from each *M. intracellulare* strain and a DNA sample derived from *M. avium* as a template.

FIG. 2 shows a result of melting curve analysis obtained in Example 4, which is obtained based on the result of the real-time PCR by the intercalator method using primer Mint 02_T7pa Fw1 and primer Mint 02_T7pa Rv1, and using DNA samples derived from 18 species of *Mycobacterium* genus and a DNA sample derived from *Escherichia coli* as a template.

FIG. 3 shows an amplification curve obtained in Example 6, which is obtained by the real-time PCR using primer Mint 02_T7pa Fw1 and primer Mint 02_T7pa Rv1, and using DNA sample derived from *M. intracellulare* as a template.

FIG. 4 shows the results of detection performed by the real-time PCR in Example 6, which is a standard curve drawn by plotting Ct value (y-axis) for the copy number of genome (x-axis, logarithmic scale) of each DNA sample for PCR.

DESCRIPTION OF EMBODIMENTS

In the present invention, *M. intracellulare* gene refers to an arbitral unit of nucleotide sequence (a region) in the entire genome sequence owned by *Mycobacterium intracellulare*. The entire genome sequence of *Mycobacterium intracellulare* has not been completed yet.

The oligonucleotide of the present invention includes an oligonucleotide comprising a part or the entire of the nucleotide sequence shown in any of SEQ ID NO: 1 to SEQ ID NO: 15, or a part or the entire of the sequence complementary to the nucleotide sequence shown in any of SEQ ID NO: 1 to SEQ ID NO: 15, wherein the oligonucleotide is capable of hybridizing with a nucleotide sequence of *Mycobacterium intracellulare* gene (hereinafter, optionally, briefly referred to as "the oligonucleotide of the present invention").

An example of the oligonucleotide of the present invention which comprises a part or the entire of the nucleotide sequences shown in any of SEQ ID NO: 1 to SEQ ID NO: 15 includes, for example, (1) an oligonucleotide comprising a nucleotide sequence having a sequence homology of not less than 70%, preferably not less than 80%, more preferably not less than 90%, further more preferably not less than 95% to any of the nucleotide sequences shown in SEQ ID NO: 1 to SEQ ID NO: 15, or (2) an oligonucleotide comprising not less than 10 consecutive nucleotides, preferably not less than 15 consecutive nucleotides, more preferably not less than 18 consecutive nucleotides in the sequences shown in any of SEQ ID NO: 1 to SEQ ID NO: 15, or the like.

A specific example of the oligonucleotide of the present invention which comprises the entire of the nucleotide sequences shown in any of SEQ ID NO: 1 to SEQ ID NO: 15 includes, for example, the oligonucleotide which consists of the nucleotide sequence shown in any of SEQ ID NO: 1 to SEQ ID NO: 15, or the oligonucleotide which comprises the nucleotide sequence shown in any of SEQ ID NO: 1 to SEQ ID NO: 15.

A specific example of the oligonucleotide comprising a part of the nucleotide sequence shown in any of SEQ ID NO: 1 to SEQ ID NO: 15 includes, for example, the one comprising a part or the entire of the nucleotide sequence shown in any of SEQ ID NO: 16 to SEQ ID NO: 129. Preferably, an oligonucleotide comprising not less than 10 consecutive nucleotides, preferably not less than 15 consecutive nucleotides, more preferably not less than 18 consecutive nucleotides in the nucleotide sequence shown in any of SEQ ID NO: 16 to SEQ ID NO: 129, is included.

A specific example of the oligonucleotide comprising the entire of the nucleotide sequence shown in any of SEQ ID NO: 16 to SEQ ID NO: 129 includes an oligonucleotide consisting of a nucleotide sequences shown in any of SEQ ID NO: 16 to SEQ ID NO: 129, or an oligonucleotide comprising a nucleotide sequence shown in any of SEQ ID NO: 16 to SEQ ID NO: 129.

A specific example of an oligonucleotide comprising a part of the nucleotide sequence shown in SEQ ID NO: 1 includes, for example, the one comprising a part or the entire of the nucleotide sequence shown in any of SEQ ID NO: 16 to SEQ ID NO: 23, or SEQ ID NO: 92 to SEQ ID NO: 95.

A specific example of an oligonucleotide comprising a part of the nucleotide sequence shown in SEQ ID NO: 2 includes, for example, the one comprising a part or the entire of the nucleotide sequence shown in any of SEQ ID NO: 24 to SEQ ID NO: 27, or SEQ ID NO: 96 to SEQ ID NO: 97.

A specific example of an oligonucleotide comprising a part of the nucleotide sequence shown in SEQ ID NO: 3 includes, for example, the one comprising a part or the entire of the nucleotide sequence shown in any of SEQ ID NO: 28 to SEQ ID NO: 33, or SEQ ID NO: 98 to SEQ ID NO: 100.

A specific example of an oligonucleotide comprising a part of the nucleotide sequence shown in SEQ ID NO: 4 includes, for example, the one comprising a part or the entire of the nucleotide sequence shown in any of SEQ ID NO: 34 to SEQ ID NO: 35, or SEQ ID NO: 101.

A specific example of an oligonucleotide comprising a part of the nucleotide sequence shown in SEQ ID NO: 5 includes, for example, the one comprising a part or the entire of the nucleotide sequence shown in any of SEQ ID NO: 36 to SEQ ID NO: 39, or SEQ ID NO: 102 to SEQ ID NO: 103.

A specific example of an oligonucleotide comprising a part of the nucleotide sequence shown in SEQ ID NO: 6 includes, for example, the one comprising a part or the entire of the nucleotide sequence shown in any of SEQ ID NO: 40 to SEQ ID NO: 47, or SEQ ID NO: 104 to SEQ ID NO: 107.

A specific example of an oligonucleotide comprising a part of the nucleotide sequence shown in SEQ ID NO: 7 includes, for example, the one comprising a part or the entire of the nucleotide sequence shown in any of SEQ ID NO: 48 to SEQ ID NO: 53, or SEQ ID NO: 108 to SEQ ID NO: 110.

A specific example of an oligonucleotide comprising a part of the nucleotide sequence shown in SEQ ID NO: 8 includes, for example, the one comprising a part or the entire of the nucleotide sequence shown in any of SEQ ID NO: 54 to SEQ ID NO: 57, or SEQ ID NO: 111 to SEQ ID NO: 112.

A specific example of an oligonucleotide comprising a part of the nucleotide sequence shown in SEQ ID NO: 9 includes, for example, the one comprising a part or the entire of the nucleotide sequence shown in any of SEQ ID NO: 58 to SEQ ID NO: 63, or SEQ ID NO: 113 to SEQ ID NO: 115.

A specific example of an oligonucleotide comprising a part of the nucleotide sequence shown in SEQ ID NO: 10 includes, for example, the one comprising a part or the entire of the nucleotide sequence shown in any of SEQ ID NO: 64 to SEQ ID NO: 69, or SEQ ID NO: 116 to SEQ ID NO: 118.

A specific example of an oligonucleotide comprising a part of the nucleotide sequence shown in SEQ ID NO: 11 includes, for example, the one comprising a part or the entire of the nucleotide sequence shown in any of SEQ ID NO: 70 to SEQ ID NO: 73, or SEQ ID NO: 119 to SEQ ID NO: 120.

A specific example of an oligonucleotide comprising a part of the nucleotide sequence shown in SEQ ID NO: 12 includes, for example, the one comprising a part or the entire of the nucleotide sequence shown in any of SEQ ID NO: 74 to SEQ ID NO: 77, or SEQ ID NO: 121 to SEQ ID NO: 122.

A specific example of an oligonucleotide comprising a part of the nucleotide sequence shown in SEQ ID NO: 13 includes, for example, the one comprising a part or the entire of the nucleotide sequence shown in any of SEQ ID NO: 78 to SEQ ID NO: 81, or SEQ ID NO: 123 to SEQ ID NO: 124.

A specific example of an oligonucleotide comprising a part of the nucleotide sequence shown in SEQ ID NO: 14 includes, for example, the one comprising a part or the entire of the nucleotide sequence shown in any of SEQ ID NO: 82 to SEQ ID NO: 87, or SEQ ID NO: 125 to SEQ ID NO: 127.

A specific example of an oligonucleotide comprising a part of the nucleotide sequence shown in SEQ ID NO: 15 includes, for example, the one comprising a part or the entire of the nucleotide sequence shown in any of SEQ ID NO: 88 to SEQ ID NO: 91, or SEQ ID NO: 128 to SEQ ID NO: 129.

An oligonucleotide of the present invention which comprises a part or the entire of the sequence complementary to the nucleotide sequence shown in any of SEQ ID NO: 1 to SEQ ID NO: 15 includes, for example, an oligonucleotide comprising a part or the entire of the nucleotide sequence, wherein the oligonucleotide is capable of hybridizing with the nucleotide sequence shown in any of SEQ ID NO: 1 to SEQ ID NO: 15 of the present invention, and the like.

The above described oligonucleotide comprising a part or the entire of the nucleotide sequence which is capable of hybridizing with the nucleotide sequence shown in any of SEQ ID NO: 1 to SEQ ID NO: 15 of the present invention includes, in particular, an oligonucleotide having a part or the entire of the nucleotide sequence which is capable of hybridizing under high stringent condition or stringent condition with the oligonucleotide shown in any of SEQ ID NO: 1 to SEQ ID NO: 15 of the present invention, and the like.

It should be noted that, the phrase of "high stringent condition" used herein means, specifically, for example, "the condition where hybridization is carried out in 50% formamide at 42 to 70° C., preferably 60 to 70° C., and followed by washing with 0.2 to 2×SSC containing 0.1% sodium dodecyl sulfate (SDS) at 25 to 70° C."

In addition, the phrase of "stringent condition" means, specifically, for example, "the condition where hybridization is carried out in 6×SSC or a hybridization solution with equivalent salt concentration at the temperature of 50 to 70° C. for 16 hours, and then, if needed, pre-washing with 6×SSC or a solution with the equivalent salt concentration, and followed by washing with 1×SSC or a solution with the equivalent salt concentration and the like".

An example of the oligonucleotide comprising a part or the entire of the sequence complementary to the nucleotide sequences shown in any of SEQ ID NO: 1 to SEQ ID NO: 15 of the present invention includes, for example, (1) an oligonucleotide comprising a nucleotide sequence having a sequence homology of not less than 70%, preferably not less than 80%, more preferably not less than 90%, further more preferably not less than 95% to the nucleotide sequence complementary to the nucleotide sequence shown in any of SEQ ID NO: 1 to SEQ ID NO: 15, or (2) an oligonucleotide comprising not less than 10 consecutive nucleotides, preferably not less than 15 consecutive nucleotides, more preferably not less than 20 consecutive nucleotides in the sequence complementary to the nucleotide sequence shown in any of SEQ ID NO: 1 to SEQ ID NO: 15, and the like.

A specific example of the oligonucleotide comprising the entire of the sequence complementary to the nucleotide sequence shown in any of SEQ ID NO: 1 to SEQ ID NO: 15 of the present invention includes, for example, an oligonucleotide consisting of the sequence complementary to the nucleotide sequence shown in any of SEQ ID NO: 1 to SEQ ID NO: 15, or an oligonucleotide which comprises the sequence complementary to the nucleotide sequence shown in any of SEQ ID NO: 1 to SEQ ID NO: 15.

A specific example of the oligonucleotide comprising a part of the sequence complementary to the nucleotide sequence shown in any of SEQ ID NO: 1 to SEQ ID NO: 15 includes, for example, an oligonucleotide comprising a part or the entire of the sequence complementary to the nucleotide sequence shown in any of SEQ ID NO: 16 to SEQ ID NO: 129. Preferably, an oligonucleotide comprising not less than 10 consecutive nucleotides, preferably not less than 15 consecutive nucleotides, more preferably not less than 18 consecutive nucleotides in the sequence complementary to the nucleotide sequence shown in any of SEQ ID NO: 16 to SEQ ID NO: 129, is included.

A specific example of the oligonucleotide comprising the entire of the sequence complementary to the nucleotide sequence shown in any of SEQ ID NO: 16 to SEQ ID NO: 129 includes, for example, an oligonucleotide consisting of a sequence complementary to the nucleotide sequence shown in any of SEQ ID NO: 16 to SEQ ID NO: 129, or an oligonucleotide comprising a nucleotide sequence complementary to the sequence shown in any of SEQ ID NO: 16 to SEQ ID NO: 129.

The oligonucleotide capable of hybridizing with the nucleotide sequence of *M. intracellulare* gene involved in the present invention includes an oligonucleotide comprising a nucleotide sequence capable of hybridizing with the nucleotide sequence of *M. intracellulare* gene under the above described high stringent condition or the stringent condition, and the like. The high stringent condition and the stringent condition are as described above.

It should be noted that, the oligonucleotide of the present invention may be either deoxyribonucleic acid (DNA) or ribonucleic acid (RNA). In the case of ribonucleic acid, it goes without saying that thymidine residue (T) may be read as uridine (U) residue. In addition, it may be a DNA comprising uridine residue which is synthesized by exchanging T at arbitral position by U. Also, it may be an RNA comprising thymidine residue which is synthesized by exchanging U at arbitral position by T. In addition, there may be deletion, insertion or replacement of one or plural nucleotides. One or plural nucleotides may be a modified nucleotide such as inosine (I).

Method for obtaining the oligonucleotide of the present invention includes, for example, but not limited to, a method for preparing by chemical synthesis well known per se. In this method, it is possible to obtain an oligonucleotide of the same quality without difficulty in larger scale at lower cost compared to the method of obtaining the oligonucleotide or the polynucleotide by genetic engineering technique using a vector and the like (cloning method).

For example, by a conventional method of DNA synthesis using a DNA synthesizer, an oligonucleotide is synthesized according to the conventional phosphoramidite method, and purified by a routine procedure using the anion exchange column chromatography. And thus, an objective oligonucleotide of the present invention can be obtained.

Alternatively, using vendor's custom service of contract synthesis, the oligonucleotide may be purchased from the vendor.

The means for searching (screening) an oligonucleotide which can attain the purpose of the present invention include the subtraction method as described in FEMS Microbiology Letters 166: 63-70, 1998 or Systematic and Applied Microbiology 24: 109-112, 2001. This is a methodology concentrating a candidate sequence by subtracting a nucleotide sequence which reacts with a fragment of genomic DNA derived from a species to be differentiated from a group of fragments derived from the target genomic DNA.

In addition, there is an approach such that a target genomic DNA and a differential display of amplification products from a target genomic DNA derived from a species to be differentiated are prepared. Namely, there is a method utilizing the arbitrarily primed polymerase chain reaction (AP-PCR) and the like (JP-A-11-155589).

Further, also by the use of so called microarray method, searching of an oligonucleotide which can attain the purpose of the present invention can also be performed, and the oligonucleotide of the present invention can be obtained. The brief description of the method is as follows:

That is, for example, a shotgun clone of genomic DNA derived from *M. intracellulare* is prepared, and then the DNA is purified from the obtained shotgun clone. After that, the purified DNA derived from the shotgun clone is amplified by the PCR and the like, the amplified DNA is arranged on a slide glass and a microarray is prepared by the conventional method. Separately, a fluorescence-labeled DNA fragment group (Label-1) is prepared from genomic DNA derived from detection target of *M. intracellulare*. On the other hand, a fluorescent labeled DNA fragment group (Label-2) is prepared separately from the genomic DNA derived from a species to be differentiated. And the reactivity (binding potency) of each Label-1 and Label-2 to the purified DNA on the microarray is assayed by a competitive hybridization method using the Label-1 and Label-2 in the same reaction system. By this assay, the candidate sequence group which react more specifically to the fragment group (Label-1) derived from genomic DNA of the target *M. intracellulare* can be selected (for example, Non-Patent Literature 1, etc.).

By the above described method, an oligonucleotide which hybridizes specifically with a nucleotide sequence of target *M. intracellulare* gene can be selected.

An example of the method for selection of the oligonucleotide of the present invention using the microarray method will be described in detail as follows:

(1) Preparation of Purified Genomic DNA Derived from *M. intracellulare*

At first, the microbial cell of *M. intracellulare* strain is subjected to conventional disrupting treatment (for example, the pulverizing treatment of microbial cell by autoclaving and using glass beads and the like), and then extraction and purification of DNA may be carried out according to the conventional procedures.

(2) Preparation of Whole Genome Shotgun Library

As an example of the method for preparing Whole Genome Shotgun library of *M. intracellulare*, a method modified from the Whole Genome Shotgun method described in Venter et al., Science 2001 Feb. 16; 291 (5507): 1304-1351 will be described below.

First, the purified genomic DNA derived from *M. intracellulare* obtained in the above described (1) is diluted with an appropriate buffer solution and the like, and then subjected to DNA fragmentation treatment, for example, in the presence of 20% final concentration of glycerol, by treating for about 1 to 5 minutes using a nebulizer under a pressure of 5 to 9 kPa. The fraction obtained is purified using a commercially available extraction column.

After that, the obtained fraction (DNA fragments, containing the objective DNA fragments) is inserted into a vector DNA by ligation according to the routine procedures, and the recombinant DNA (Whole Genome Shotgun Library of *M. intracellulare*) is obtained.

The vector DNA to be used for this purpose includes, in the case where the host cell for subsequent transformation is *E. coli*, for example, the vectors such as pBS (e.g., pBSII sk$^+$ vector (produced by Stratagene Corporation)), pQE-TRI plasmid (produced by Qiagen GmbH), pBluescript, pET, pGEM-3Z, pGEX and the like. Depending on the kind of vector to be used, prior to the ligation, terminal of the DNA fragments may be blunted by treating with DNA polymerase and the like in advance.

After that, using the obtained recombinant DNA, an appropriate host cell is transformed to obtain a transformant.

The host cell to be used for this purpose includes, for example, *E. coli*, preferably the strain of JM109, DH5α, TOP10 and the like. In addition to these, competent cells having higher transformation efficiency for the plasmid and the phage DNA may be used. For example, *E. coli* JM109 Competent Cells (Takara Bio Inc.) and the like are included.

Transformation of the host cell can be carried out by the conventional method [for example, the D. M. Morrison's method (Method in Enzymology, 68, 326-331, 1979) and the like]. In addition, when a commercially available competent cell is used, the transformation may be carried out according to the protocol provided for the product.

The method for selection of the transformant which has been introduced with "the recombinant DNA into which an objective DNA fragment has been incorporated" includes, for example, a method through the use of property of the vector used for transformation. For example, when a vector comprising ampicillin-resistant gene is used, by culturing the transformant on a medium containing ampicillin and by selecting the resulting clone, the Library of the transformant which has been transformed by "the recombinant DNA incorporated with the objective DNA fragment" (Whole Genome Shotgun Library of genome DNA derived from *M. intracellulare*) can be obtained easily.

(3) Preparation of Microarray

Next, the microarray is prepared by the following method.

Namely, from the transformant (Whole Genome Shotgun clone library derived from *M. intracellulare* genome) obtained in the above described (2), DNA is purified according to the routine methods.

Using the purified DNA as a template, and using a suitable primer (it may be a commercially available primer, for example, M13 Primer M1 (produced by Takara Bio Inc.) and M13 Primer RV (produced by Takara Bio Inc.) and the like), the PCR is carried out according to the routine procedure, and then the resulting PCR amplification product is purified. Subsequently, according to the routine procedures, the purified PCR amplification product is spotted on a slide glass for microarray. The spots are irradiated with UV light (60 mJ/cm$^2$ to 300 mJ/cm$^2$; usually 150 mJ/cm$^2$) to fix the PCR amplification product (having a nucleotide sequence fragmented from genomic DNA derived from the target *M. intracellulare*) on the slide glass, and thus the microarray is prepared.

(4) Labeling of Target Genomic DNA with Fluorescent Dye (i) Labeling of Target Genomic DNA with Fluorescent Dye For example, by a routine procedure such as an indirect labeling method using hexylamino-UTP, a purified genomic DNA derived from *M. intracellulare* obtained, for example, by the method described in the above (1) is labeled with a labeling substance. In addition, a genomic DNA for reference (the genomic DNA derived from a species to be differentiated from *M. intracellulare*) is labeled with a labeling substance which is different from the labeling substance used for labeling the above described purified genomic DNA derived from *M. intracellulare*.

The labeling substance to be used for labeling the above described DNA is the labeling substances usually used in this field, and widely used labeling substances include Alexa555 (product name of Invitrogen Corp.), Alexa647 (product name of Invitrogen Corp.), Cy3 (product name of Amersham Biosciences Corp.), Cy5 (product name of Amersham Biosciences Corp.), and the like.

The method for labeling the above described DNA using labeling substances as described above includes an indirect labeling method which has been modified from a protocol published by DeRisi Laboratory (www.microarray.org). In this method, at first, by carrying out an enzymatic extension reaction, a DNA chain which has been incorporated with a αUTP having an amino group into the molecule is produced.

And, to this amino group of the DNA fragments, a fluorescent dye (succinimide body) is coupled chemically, thereby, the DNA is labeled. For the preparation of DNA fragments before labeling the DNA (incorporation of a αUTP) by this method, commercially available kit such as BioPrime DNA labeling system (produced by Invitrogen Corp.) may be used.

Below, an example of the method for labeling DNA by the above described method using Alexa647 and Alexa555 will be described.

That is, firstly, a starting material (a purified genomic DNA derived from M. intracellulare, or a genomic DNA for reference) is subjected to heat denaturation treatment according to the routine procedure. After that, to the heat treated material, DTT, a mixed solution of dATP/dCTP/dGTP, dTTP, Ha-dUTP and Klenow enzyme are added, and the extension reaction is carried out at 37° C. for about 3 hours. The obtained reaction product is placed onto an ultrafiltration column and centrifuged at 14,000 rpm for about 4 minutes, and then the concentrated solution is recovered in a microtube, and dried using a centrifugal vacuum drier and the like. After that, to the dried above reaction product, $NaHCO_3$ is added and mixed, and then left for standing at ambient temperature for 2 to 3 minutes.

Separately, a solution of Alexa555 (or Alexa647) dissolved in DMSO (dye Solution Alexa555, dye Solution Alexa647) is prepared. This dye Solution Alexa555 is added to the above described reaction product obtained by using the genomic DNA for reference. In addition, the dye Solution Alexa647 is added to the above described reaction product obtained by using the genomic DNA derived from M. intracellulare. Each reaction product is incubated under light shielding at 40° C. for about 60 minutes. Further, each reaction product is added with 4 M $NH_2OH$ and mixed, and incubated under light shielding for about 15 minutes to obtain the labeled product of each genomic DNA. After that, the obtained labeled product is placed onto an ultrafiltration column and centrifuged at 14,000 rpm for about 4 minutes. The concentrated solution is recovered in a microtube, and then dried using a centrifugal vacuum drier.

(ii) Fragmentation Process of the Labeled Products

To each of the labeled product of the genomic DNA in dry state obtained in the above i) of (4), a solution of the following components with final concentrations of 0.04 M Tris-acetate (pH 8.1), 0.1 M potassium acetate, and 0.03 M magnesium acetate tetrahydrate is prepared and added, and mixed in suspension. The suspension is heat-treated at 94° C. for about 15 minutes, and the fragmentation products of labeled products of respective genomic DNA with 100 bases to 300 bases are obtained (Alexa555-labeled product, Alexa647-labeled product, respectively).

The Alexa555-labeled product and Alexa647-labeled product obtained are each placed onto an ultrafiltration column and centrifuged at 14,000 rpm for about 4 minutes; after that, each concentrated solution is recovered in a same microtube; and then dried thoroughly using a centrifugal vacuum drier or the like.

Subsequently, to this microtube, a reagent solution which is prepared by mixing salmon sperm DNA and ArrayHyb Hybridization buffer is added, and the dry material obtained above is mixed in suspension, and then incubated at 95° C. for about 5 minutes to prepare a mixed solution of the Alexa555/Alexa647 labeled products.

(5) Microarray Hybridization

On a microarray of Whole Genome Shotgun clone Library of genomic DNA derived from M. intracellulare prepared in the above described step (3), a mixed solution of the Alexa555/Alexa647 labeled products prepared in the above described (ii) of (4) is placed, and kept at 65° C. under light shielding for not less than 8 hours to allow hybridization. After hybridization, the microarray is washed, and then dried by centrifugation at 800 rpm for about 5 minutes.

(6) Measurement of Fluorescence Intensity: from Signal Detection to Quantification Using a fluorescence readout scanner, the fluorescence intensity of the microarray on which the microarray hybridization has been carried out as described in the above (5) is measured. On this occasion, the fluorescence intensity is measured by 2 channels of Alexa555 and Alexa647 to obtain fluorescence detection data.

Quantification of the fluorescence signal may be performed using commercially available DNA tip expression image analysis software and the like. And, according to the operational procedure of the software, automated spot recognition, background calculation, and normalization of the fluorescence intensity ratio may be carried out.

The Alexa647-labeled product used for hybridization is a group of DNA fragments prepared from the labeled genomic DNA derived from M. intracellulare, and the Alexa555-labeled product is a group of DNA fragments prepared from labeled genomic DNA for reference. Therefore, when the fluorescence intensity of Alexa555 and Alexa647 of a certain spot on a microarray is measured, and the fluorescence intensity ratio of Alexa647 for Alexa555 is high, it indicates that the DNA fragment (PCR product) in the spot has been hybridized more strongly with the Alexa647-labeled product, namely, with the genomic DNA derived from M. intracellulare. And, the specificity of the DNA fragment (PCR product) for M. intracellulare is deemed to be high.

On the other hand, when the fluorescence intensity of Alexa555 and Alexa647 of a certain spot is measured, and the fluorescence intensity ratio of Alexa647 for Alexa555 is low, it indicates that the specificity of the DNA fragment (PCR product) in the spot for the genomic DNA derived from M. intracellulare is low, and the cross-reaction with Alexa555-labeled product, namely with the genomic DNA for reference was observed. In addition to this case, the case where the fluorescence intensities of Alexa555 and Alexa647 are the same level, and the case where no fluorescence of both Alexa555 and Alexa647 is detected, the specificity of the DNA fragment (PCR product) in the spot for M. intracellulare is deemed to be low.

And so, for example, on the basis of the fluorescence intensity ratio of Alxa555/aAlexa647 (Ratio) detected on the microarray, and analyzing the results, for example, by making up a scatter chart (scatter plot), to carry out the screening for detecting a specific sequence for a M. intracellulare.

In the analysis, the numeric value of Cy3/Cy5 ratio for the specific DNA for M. intracellulare among the positive control sequence employed will be a useful reference value for the assessment of specificity.

As a result of the screening, a spot which provides a specific signal to M. intracellulare (the case where the fluorescence intensity of Alexa647 is strong) is selected as a candidate.

It should be noted that, for the purpose of screening a candidate sequence for further specific detection of M. intracellulare among the selected clones, for example, secondary screening may be carried out.

For example, (a) the genomic DNA derived from plural number of M. intracellulare strains is labeled with a labeling substance by the same manner as described above, and fragmented.

(b) Similarly, the genomic DNA derived from a species to be differentiated as a reference is labeled with a labeling substance which is different from the labeling substance used for *M. intracellulare* strain, and fragmented.

For each *M. intracellulare* strain, respective mixture of these (a) and (b) is prepared, namely, the mixture of the aforementioned fragmentation product of the labeled product of genomic DNA derived from *M. intracellulare* strains and the fragmentation product of the labeled product of genomic DNA derived from reference strain is obtained.

Using a mixture of each labeled fragment, a competitive hybridization is performed for the microarray on which the candidate spots selected by primary screening are mounted. And, the spot which reacts redundantly with the labeled fragment of genomic DNA derived from plural number of *M. intracellulare* strains is selected. The DNA fragment of this spot is determined as a final candidate clone.

Subsequently, the determination of nucleotide sequence of the obtained candidate clone is carried out according to the routine procedure using equipment such as a sequencer usually used in this field, for example, an ABI PRISM310 capillary sequencer (produced by Applied Biosystems Inc.) etc.,.

The primer for detecting *M. intracellulare* of the present invention includes a primer comprising an oligonucleotide comprising a part or the entire of the nucleotide sequence shown in any of SEQ ID NO: 1 to SEQ ID NO: 15, or a part or the entire of the sequence complementary to the nucleotide sequence shown in any of SEQ ID NO: 1 to SEQ ID NO: 15, wherein the oligonucleotide is capable of hybridizing with a nucleotide sequence of *M. intracellulare* gene (hereinafter, optionally referred to as the primer of the present invention).

In addition, the primer of the present invention may be the one which is designed, in compliance with the conditions of the nucleic acid amplification reaction such as PCR (including the real-time PCR), nucleic acid hybridization and the like, and by selecting an appropriate length of appropriate region in consideration of dissociation temperature (Tm value) and the like from the oligonucleotides comprising a part or the entire of the nucleotide sequence shown in any of SEQ ID NO: 1 to SEQ ID NO: 15, or the oligonucleotide comprising a part or the entire of the sequence complementary to the nucleotide sequence shown in any of SEQ ID NO: 1 to SEQ ID NO: 15.

Preferably, the primer includes an oligonucleotide having a length with 10 to 50 nucleotides, more preferably 10 to 35 nucleotides, further more preferably 18 to 25 nucleotides, further more preferably 18 to 22 nucleotides, which is considered to be a necessary nucleotide number for retaining specificity as a primer.

As to a method for designing the primer, a software commonly used for designing primer or, for example, a primer design tool on the web, Primer 3 (produced by Whitehead Institute for Biomedical Research) and the like may be used.

A specific example of an oligonucleotide to be used for the primer of the present invention (the oligonucleotide of the present invention), which comprises a part or the entire of the nucleotide sequence shown in any of SEQ ID NO: 1 to SEQ ID NO: 15, or a part or the entire of the sequence complementary to the nucleotide sequence shown in any of SEQ ID NO: 1 to SEQ ID NO: 15, wherein the oligonucleotide is capable of hybridizing with the nucleotide sequence of *M. intracellulare* gene, is the same one as described in the above explanation of the oligonucleotide of the present invention.

Specific example of the primer of the present invention includes, for example, an oligonucleotide comprising a part or the entire of the nucleotide sequence shown in any of SEQ ID NO: 16 to SEQ ID NO: 129, wherein the oligonucleotide is capable of hybridizing with the nucleotide sequence of *M. intracellulare* gene, or an oligonucleotide comprising a part or the entire of the nucleotide sequence complementary to the sequence shown in any of SEQ ID NO: 16 to SEQ ID NO: 129, wherein the oligonucleotide is capable of hybridizing with the nucleotide sequence of *M. intracellulare* gene.

A preferable specific example of the primer of the present invention includes, for example, an oligonucleotide comprising a part or the entire of the nucleotide sequence shown in any of SEQ ID NO: 16 to SEQ ID NO: 91, wherein the oligonucleotide is capable of hybridizing with the nucleotide sequence of *M. intracellulare* gene, or an oligonucleotide comprising a part or the entire of the sequence complementary to the nucleotide sequence shown in any of SEQ ID NO: 16 to SEQ ID NO: 91, wherein the oligonucleotide is capable of hybridizing with the nucleotide sequence of *M. intracellulare* gene.

The more preferable specific example of the primer of the present invention includes, for example, an oligonucleotide comprising a part or the entire of the nucleotide sequence shown in any of SEQ ID NO: 16 to SEQ ID NO: 19, SEQ ID NO: 24, SEQ ID NO: 25, SEQ ID NO: 28, SEQ ID NO: 29, SEQ ID NO: 34 to SEQ ID NO: 37, SEQ ID NO: 40 to SEQ ID NO: 43, SEQ ID NO: 48, SEQ ID NO: 49, SEQ ID NO: 54 to SEQ ID NO: 59, SEQ ID NO: 64, SEQ ID NO: 65, SEQ ID NO: 70, SEQ ID NO: 71, SEQ ID NO: 74, SEQ ID NO: 75, SEQ ID NO: 78, SEQ ID NO: 79, SEQ ID NO: 82, SEQ ID NO: 83, SEQ ID NO: 88, or SEQ ID NO: 89, wherein the oligonucleotide is capable of hybridizing with the nucleotide sequence of *M. intracellulare* gene, or an oligonucleotide comprising a part or the entire of the sequence complementary to the nucleotide sequence shown in any of SEQ ID NO: 16 to SEQ ID NO: 19, SEQ ID NO: 24, SEQ ID NO: 25, SEQ ID NO: 28, SEQ ID NO: 29, SEQ ID NO: 34 to SEQ ID NO: 37, SEQ ID NO: 40 to SEQ ID NO: 43, SEQ ID NO: 48, SEQ ID NO: 49, SEQ ID NO: 54 to SEQ ID NO: 59, SEQ ID NO: 64, SEQ ID NO: 65, SEQ ID NO: 70, SEQ ID NO: 71, SEQ ID NO: 74, SEQ ID NO: 75, SEQ ID NO: 78, SEQ ID NO: 79, SEQ ID NO: 82, SEQ ID NO: 83, SEQ ID NO: 88, or SEQ ID NO: 89, wherein the oligonucleotide is capable of hybridizing with the nucleotide sequence of *M. intracellulare* gene.

The still more preferable specific example of the primer of the present invention includes, for example, an oligonucleotide consisting of the nucleotide sequence shown in any of SEQ ID NO: 16 to SEQ ID NO: 19, SEQ ID NO: 24, SEQ ID NO: 25, SEQ ID NO: 28, SEQ ID NO: 29, SEQ ID NO: 34 to SEQ ID NO: 37, SEQ ID NO: 40 to SEQ ID NO: 43, SEQ ID NO: 48, SEQ ID NO: 49, SEQ ID NO: 58, SEQ ID NO: 59, SEQ ID NO: 64, SEQ ID NO: 65, SEQ ID NO: 70, SEQ ID NO: 71, SEQ ID NO: 74, SEQ ID NO: 75, SEQ ID NO: 78, SEQ ID NO: 79, SEQ ID NO: 82, SEQ ID NO: 83, SEQ ID NO: 88, SEQ ID NO: 89, wherein the oligonucleotide is capable of hybridizing with the nucleotide sequence of *M. intracellulare* gene, or an oligonucleotide consisting of the sequence complementary to the nucleotide sequence shown in any of SEQ ID NO: 16 to SEQ ID NO: 19, SEQ ID NO: 24, SEQ ID NO: 25, SEQ ID NO: 28, SEQ ID NO: 29, SEQ ID NO: 34 to SEQ ID NO: 37, SEQ ID NO: 40 to SEQ ID NO: 43, SEQ ID NO: 48, SEQ ID NO: 49, SEQ ID NO: 58, SEQ ID NO: 59, SEQ ID NO: 64, SEQ ID NO: 65, SEQ ID NO: 70, SEQ ID NO: 71, SEQ ID NO: 74, SEQ ID NO: 75, SEQ ID NO: 78, SEQ ID NO: 79, SEQ ID NO: 82, SEQ ID NO: 83, SEQ ID NO: 88, or SEQ ID NO: 89, wherein the oligonucleotide is capable of hybridizing with the nucleotide sequence of *M. intracellulare* gene.

It should be noted that, the primers comprising the nucleotide sequence shown in SEQ ID NO: 16 to SEQ ID NO: 23 are designed based on the nucleotide sequence shown in SEQ ID NO: 1.

The primers comprising the nucleotide sequence shown in SEQ ID NO: 24 to SEQ ID NO: 27 are designed based on the nucleotide sequence shown in SEQ ID NO: 2.

The primers comprising the nucleotide sequence shown in SEQ ID NO: 28 to SEQ ID NO: 33 are designed based on the nucleotide sequence shown in SEQ ID NO: 3.

The primers comprising the nucleotide sequence shown in SEQ ID NO: 34 to SEQ ID NO: 35 are designed based on the nucleotide sequence shown in SEQ ID NO: 4.

The primers comprising the nucleotide sequence shown in SEQ ID NO: 36 to SEQ ID NO: 39 are designed based on the nucleotide sequence shown in SEQ ID NO: 5.

The primers comprising the nucleotide sequence shown in SEQ ID NO: 40 to SEQ ID NO: 47 are designed based on the nucleotide sequence shown in SEQ ID NO: 6.

The primers comprising the nucleotide sequence shown in SEQ ID NO: 48 to SEQ ID NO: 53 are designed based on the nucleotide sequence shown in SEQ ID NO: 7.

The primers comprising the nucleotide sequence shown in SEQ ID NO: 54 to SEQ ID NO: 57 are designed based on the nucleotide sequence shown in SEQ ID NO: 8.

The primers comprising the nucleotide sequence shown in SEQ ID NO: 58 to SEQ ID NO: 63 are designed based on the nucleotide sequence shown in SEQ ID NO: 9.

The primers comprising the nucleotide sequence shown in SEQ ID NO: 64 to SEQ ID NO: 69 are designed based on the nucleotide sequence shown in SEQ ID NO: 10.

The primers comprising the nucleotide sequence shown in SEQ ID NO: 70 to SEQ ID NO: 73 are designed based on the nucleotide sequence shown in SEQ ID NO: 11.

The primers comprising the nucleotide sequence shown in SEQ ID NO: 74 to SEQ ID NO: 77 are designed based on the nucleotide sequence shown in SEQ ID NO: 12.

The primers comprising the nucleotide sequence shown in SEQ ID NO: 78 to SEQ ID NO: 81 are designed based on the nucleotide sequence shown in SEQ ID NO: 13.

The primers comprising the nucleotide sequence shown in SEQ ID NO: 82 to SEQ ID NO: 87 are designed based on the nucleotide sequence shown in SEQ ID NO: 14.

The primers comprising the nucleotide sequence shown in SEQ ID NO: 88 to SEQ ID NO: 91 are designed based on the nucleotide sequence shown in SEQ ID NO: 15.

In the nucleotide sequence shown in SEQ ID NO: 1, locations of the nucleotide sequences which are designed as a primer having nucleotide sequences shown in SEQ ID NO: 16 to SEQ ID NO: 23 are each as follows:

SEQ ID NO: 16 (Mint 02_T7pa Fw1): $266^{th}$-$287^{th}$;
SEQ ID NO: 17 (Mint 02_T7pa Rv1): $361^{st}$-$381^{st}$;
SEQ ID NO: 18 (Mint 02_T3pa Fw1): $173^{rd}$-$190^{th}$;
SEQ ID NO: 19 (Mint 02_T3pa Rv1): $324^{th}$-$341^{st}$;
SEQ ID NO: 20 (Mint 02_con Fw1): $425^{th}$-$443^{rd}$;
SEQ ID NO: 21 (Mint 02_con Rv1): $570^{th}$-$589^{th}$;
SEQ ID NO: 22 (Mint 02_con Fw2): $63^{rd}$-$80^{th}$;
SEQ ID NO: 23 (Mint 02_con Rv2): $245^{th}$-$262^{nd}$, In the nucleotide sequence shown in SEQ ID NO: 2, locations of the nucleotide sequences which are designed as a primer having nucleotide sequences shown in SEQ ID NO: 24 to SEQ ID NO: 27 are each as follows:

SEQ ID NO: 24 (Mint 04_con Fw1): $40^{th}$-$59^{th}$;
SEQ ID NO: 25 (Mint 04_con Rv1): $187^{th}$-$205^{th}$;
SEQ ID NO: 26 (Mint 04_T3pa Fw1): $394^{th}412^{th}$;
SEQ ID NO: 27 (Mint 04_T3pa Rv1): $519^{th}$-$538^{th}$, In the nucleotide sequence shown in SEQ ID NO: 3, locations of the nucleotide sequences which are designed as a primer having nucleotide sequences shown in SEQ ID NO: 28 to SEQ ID NO: 33 are each as follows:

SEQ ID NO: 28 (Mint 06_T3pa Fw1): $458^{th}$-475th;
SEQ ID NO: 29 (Mint 06_T3pa Rv1): $608^{th}$-$627^{th}$;
SEQ ID NO: 30 (Mint 06_con Fw1): $260^{th}$-$278^{th}$;
SEQ ID NO: 31 (Mint 06_con Rv1): $389^{th}$-$408^{th}$,
SEQ ID NO: 32 (Mint 06_con Fw3): $153^{rd}$-$170^{th}$;
SEQ ID NO: 33 (Mint 06_con Rv3): $301^{st}$-$318^{th}$.

In the nucleotide sequence shown in SEQ ID NO: 4, locations of the nucleotide sequences which are designed as a primer having nucleotide sequences shown in SEQ ID NO: 34 to SEQ ID NO: 35 are each as follows:

SEQ ID NO: 34 (Mint 17_T3pa Fw1): $118^{th}$-$137^{th}$;
SEQ ID NO: 35 (Mint 17_T3pa Rv1): $282^{nd}$-$299^{th}$.

In addition, in the nucleotide sequence shown in SEQ ID NO: 5, locations of the nucleotide sequences which are designed as a primer having nucleotide sequences shown in SEQ ID NO: 36 to SEQ ID NO: 39 are each as follows:

SEQ ID NO: 36 (Mint 07_Fwpa Fw1): $106^{th}$-$123^{rd}$;
SEQ ID NO: 37 (Mint 07_Fwpa Rv1): $202^{nd}$-$220^{th}$
SEQ ID NO: 38 (Mint 07_con Fw1): $362^{nd}$-$381^{st}$.
SEQ ID NO: 39 (Mint 07_con Rv1): $500^{th}$-$518^{th}$.

In the nucleotide sequence shown in SEQ ID NO: 6, locations of the nucleotide sequences which are designed as a primer having nucleotide sequences shown in SEQ ID NO: 40 to SEQ ID NO: 47 are each as follows:

SEQ ID NO: 40 (Mint 10_Fwpa Fw1): $496^{th}$-$513^{th}$;
SEQ ID NO: 41 (Mint 10_Fwpa Rv1): $613^{th}$-$632^{nd}$;
SEQ ID NO: 42 (Mint 10_con Fw2): $750^{th}$-$769^{th}$;
SEQ ID NO: 43 (Mint 10_con Rv2): $858^{th}$-$877^{th}$;
SEQ ID NO: 44 (Mint 10_RVpa Fw1): $184^{th}$-$201^{st}$;
SEQ ID NO: 45 (Mint 10_RVpa Rv1): $336^{th}$-$353^{rd}$;
SEQ ID NO: 46 (Mint 10_con Fw1): $141^{st}$-$159^{th}$;
SEQ ID NO: 47 (Mint 10_con Rv1): $312^{th}$-$329^{th}$.

In the nucleotide sequence shown in SEQ ID NO: 7, locations of the nucleotide sequences which are designed as a primer having nucleotide sequences shown in SEQ ID NO: 48 to SEQ ID NO: 53 are each as follows:

SEQ ID NO: 48 (Mint 14_T3pa Fw1): $141^{st}$-$160^{th}$;
SEQ ID NO: 49 (Mint 14_T3pa Rv1): $249^{th}$-$266^{th}$;
SEQ ID NO: 50 (Mint 14_FWpa Fw1): $174^{th}$-$192^{nd}$;
SEQ ID NO: 51 (Mint 14_FWpa Rv1): $304^{th}$-$323^{rd}$;
SEQ ID NO: 52 (Mint 14_con Fw1): $401^{st}$-$421^{st}$;
SEQ ID NO: 53 (Mint 14_con Rv1): $513^{th}$-$530^{th}$.

In the nucleotide sequence shown in SEQ ID NO: 8, locations of the nucleotide sequences which are designed as a primer having nucleotide sequences shown in SEQ ID NO: 54 to SEQ ID NO: 57 are each as follows:

SEQ ID NO: 54 (Mint 15_RVpa Fw1): $174^{th}$-$193^{rd}$;
SEQ ID NO: 55 (Mint 15_RVpa Rv1): $294^{th}$-$312^{th}$;
SEQ ID NO: 56 (Mint 15_con Fw1): $374^{th}$-$391^{st}$;
SEQ ID NO: 57 (Mint 15_con Rv1): $522^{nd}$-$541^{st}$.

In the nucleotide sequence shown in SEQ ID NO: 9, locations of the nucleotide sequences which are designed as a primer having nucleotide sequences shown in SEQ ID NO: 58 to SEQ ID NO: 63 are each as follows:

SEQ ID NO: 58 (Mint 19_T3pa Fw1): $853^{rd}$-$872^{nd}$.
SEQ ID NO: 59 (Mint 19_T3pa Rv1): $972^{nd}$-$990^{th}$;
SEQ ID NO: 60 (Mint 19_FWpa Fw1): $183^{rd}$-$200^{th}$;
SEQ ID NO: 61 (Mint 19_FWpa Rv1): $336^{th}$-$354^{th}$;
SEQ ID NO: 62 (Mint 19_con Fw1): $512^{th}$-$530^{th}$;
SEQ ID NO: 63 (Mint 19_con Rv1): $642^{nd}$-$659^{th}$.

In the nucleotide sequence shown in SEQ ID NO: 10, locations of the nucleotide sequences which are designed as a primer having nucleotide sequences shown in SEQ ID NO: 64 to SEQ ID NO: 69 are each as follows:
SEQ ID NO: 64 (Mint 21_FWpa Fw1): $902^{nd}$-$921^{st}$;
SEQ ID NO: 65 (Mint 21_FWpa Rv1): $1015^{th}$-$1032^{nd}$;
SEQ ID NO: 66 (Mint 21_T3pa Fw1): $178^{th}$-$197^{th}$;
SEQ ID NO: 67 (Mint 21_T3pa Rv1): $271^{st}$-$290^{th}$;
SEQ ID NO: 68 (Mint 21_con Fw1): $425^{th}$-$443^{rd}$;
SEQ ID NO: 69 (Mint 21_con Rv1): $589^{th}$-$608^{th}$.

In the nucleotide sequence shown in SEQ ID NO: 11, locations of the nucleotide sequences which are designed as a primer having nucleotide sequences shown in SEQ ID NO: 70 to SEQ ID NO: 73 are each as follows:
SEQ ID NO: 70 (Mint 23_con Fw1): $360^{th}$-$379^{th}$;
SEQ ID NO: 71 (Mint 23_con Rv1): $509^{th}$-$528^{th}$;
SEQ ID NO: 72 (Mint 23_FWpa Fw1): $707^{th}$-$724^{th}$;
SEQ ID NO: 73 (Mint 23_FWpa Rv1): $844^{th}$-$862^{nd}$.

In the nucleotide sequence shown in SEQ ID NO: 12, locations of the nucleotide sequences which are designed as a primer having nucleotide sequences shown in SEQ ID NO: 74 to SEQ ID NO: 77 are each as follows:
SEQ ID NO: 74 (Mint 01con Fw1): $129^{th}$-$147^{th}$;
SEQ ID NO: 75 (Mint 01con Rv1): $291^{st}$-$313^{th}$;
SEQ ID NO: 76 (Mint 01_T7pa Fw1): $6^{th}$-$23^{rd}$;
SEQ ID NO: 77 (Mint 01_T7pa Rv1): $170^{th}$-$189^{th}$.

In the nucleotide sequence shown in SEQ ID NO: 13, locations of the nucleotide sequences which are designed as a primer having nucleotide sequences shown in SEQ ID NO: 78 to SEQ ID NO: 81 are each as follows:
SEQ ID NO: 78 (Mint 03_con Fw1): $405^{th}$-$424^{th}$;
SEQ ID NO: 79 (Mint 03_con Rv1): $523^{rd}$-$540^{th}$;
SEQ ID NO: 80 (Mint 03_con Fw2): $142^{nd}$-$161^{st}$;
SEQ ID NO: 81 (Mint 03_con Rv2): $270^{th}$-$288^{th}$.

In the nucleotide sequence shown in SEQ ID NO: 14, locations of the nucleotide sequences which are designed as a primer having nucleotide sequences shown in SEQ ID NO: 82 to SEQ ID NO: 87 are each as follows:
SEQ ID NO: 82 (Mint 12_FWpa Fw1): $189^{th}$-$207^{th}$;
SEQ ID NO: 83 (Mint 12_FWpa Rv1): $343^{rd}$-$362^{nd}$;
SEQ ID NO: 84 (Mint 12_RVpa Fw1): $634^{th}$-$652^{nd}$;
SEQ ID NO: 85 (Mint 12_RVpa Rv1): $716^{th}$-$734^{th}$;
SEQ ID NO: 86 (Mint 12_con Fw1): $296^{th}$-$315^{th}$;
SEQ ID NO: 87 (Mint 12_con Rv1): $468^{th}$-$485^{th}$.

In the nucleotide sequence shown in SEQ ID NO: 15, locations of the nucleotide sequences which are designed as a primer having nucleotide sequences shown in SEQ ID NO: 88 to SEQ ID NO: 91 are each as follows:
SEQ ID NO: 88 (Mint 18con Fw1): $69^{th}$-$89^{th}$;
SEQ ID NO: 89 (Mint 18con Rv1): $225^{th}$-$242^{nd}$;
SEQ ID NO: 90 (Mint 18con Fw2): $354^{th}$-$373^{rd}$;
SEQ ID NO: 91 (Mint 18con Rv2): $440^{th}$-$457^{th}$.

It should be noted that, in the above description, names of the primers denominated in the present invention are shown in parenthesis next to each SEQ ID NO.

The method for obtaining the primer of the present invention is as described above in the method for obtaining the nucleotide of the present invention.

In addition, the primer of the present invention may be labeled with a labeling substance.

As to the labeling substance to be used for labeling the primer of the present invention, any of known labeling substances such as radioisotope, enzyme, fluorescent substance, luminescent substance, biotin and the like may be used.

For example, the radioisotope includes $^{32}P$, $^{33}P$, $^{35}S$ and the like; the enzyme includes alkaline phosphatase, horseradish peroxydase and the like; the fluorescent substance includes Alexa555, Alexa647 (produced by Invitrogen Corporation), cyanine dye type of Cy3, Cy5 (produced by Amersham Biosciences Corp.), fluorescein and the like; the luminescent substance includes chemoluminescent reagents including Acridinium Esters and the like.

The method for labeling the primer of the present invention with a radioisotope includes a method for labeling by incorporating a radioisotope-labeled nucleotide into a primer at the time when the primer is synthesized, or a method for labeling with a radioisotope after the primer is synthesized, and the like. Specifically, as a popularly used method, random primer method, nick-translation method, 5'-terminal labeling method using T4 polynucleotide kinase, 3'-terminal labeling method using terminal deoxynucleotide transferase, RNA labeling method and the like are included.

Method for labeling the primer of the present invention with a labeling substance includes a method for labeling the oligonucleotide usually employed in this field, and the method may be selected appropriately depending on the property of respective labeling substances to be employed.

For example, the method for labeling the primer of the present invention with an enzyme includes a direct labeling method which is a routine technique in this field, in which an enzyme molecule such as alkaline phosphatase, horseradish peroxidase or the like is linked directly and covalently to the primer to be labeled.

The method for labeling the primer of the present invention with a fluorescent substance includes, for example, a method in which the fluorescence-labeled nucleotide is incorporated into the primer by a routine labeling technique in this field. In addition, by a method of replacing a nucleotide in a sequence with a nucleotide having a linker arm as a member of the sequence (see, for example, Nucleic Acids Res., 1986, vol. 14, p. 6115), the nucleotide can also be labeled with a fluorescent substance. In this case, there may be a method in which a uridine having a linker arm on 5-position is synthesized chemically from deoxyuridine by the method of synthesis disclosed in JP-A-60-500717, and using it, a fluorescent substance is introduced into the above described oligonucleotide chain.

The method for labeling the primer of the present invention with a luminescent substance or with biotin includes a routine luminescence-labeling method or a routine biotin-labeling method usually carried out for labeling nucleotides in this field.

The probe for the detecting M. intracellulare of the present invention includes a probe comprising an oligonucleotide comprising a part or the entire of the nucleotide sequence shown in any of SEQ ID NO: 1 to SEQ ID NO: 15, or a part or the entire of the sequence complementary to the nucleotide sequence shown in any of SEQ ID NO: 1 to SEQ ID NO: 15, wherein the oligonucleotide is capable of hybridizing with the nucleotide sequence of M. intracellulare gene (hereinafter, optionally referred to as the probe of the present invention).

The probe of the present invention may be the one which is designed, in compliance with the conditions of the nucleic acid amplification reaction such as the PCR (including the real-time PCR), nucleic acid hybridization and the like, and by selecting an appropriate length of appropriate region in consideration of dissociation temperature (Tm value) and the like from the oligonucleotide comprising a part or the entire of the nucleotide sequence shown in any of SEQ ID NO: 1 to SEQ ID NO: 15, or the oligonucleotide comprising a part or the entire of the sequence complementary to the nucleotide sequence shown in any of SEQ ID NO: 1 to SEQ ID NO: 15. In this regard, however, if the probe is desired to have sufficient specificity, it is desirable to design in consideration of the number of bases required in order to maintain the specificity as a probe sequence.

For example, the probe to be used for the nucleic acid hybridization method (for example, Southern hybridization, and the like) includes a probe having a length of 10 nucleotides to 700 nucleotides, preferably 100 nucleotides to 600 nucleotides, more preferably 100 nucleotides to 500 nucleotides, and further more preferably 200 nucleotides to 500 nucleotides.

In addition, for example, the probe to be used for the real-time PCR amplification system (for example, TaqMan™ Method, Molecular Beacon method, and the like) includes the one having a length of 10 nucleotides to 50 nucleotides, preferably 15 nucleotides to 40 nucleotides, and further preferably 20 nucleotides to 30 nucleotides.

A specific example of the oligonucleotide to be used for the probe of the present invention (the oligonucleotide of the present invention), which comprises a part or the entire of the nucleotide sequence shown in any of SEQ NO: 1 to SEQ ID NO: 15, or a part or the entire of the sequence complementary to the nucleotide sequence shown in any of SEQ ID NO: 1 to SEQ ID NO: 15, wherein the oligonucleotide is capable of hybridizing with the nucleotide sequence of *M. intracellulare* gene is same as described in the above explanation of the oligonucleotide of the present invention.

A specific example of the probe of the present invention includes, for example, an oligonucleotide comprising a part or the entire of the nucleotide sequence shown in any of SEQ ID NO: 16 to SEQ ID NO: 129, or an oligonucleotide comprising a part or the entire of the sequence complementary to the nucleotide sequence shown in any of SEQ ID NO: 16 to SEQ ID NO: 129, wherein the oligonucleotide is capable of hybridizing with the nucleotide sequence of *M. intracellulare* gene.

A preferable specific example of the probe of the present invention includes, for example, an oligonucleotide comprising a part or the entire of the nucleotide sequence shown in any of SEQ ID NO: 16 to SEQ ID NO: 19, SEQ ID NO: 24, SEQ ID NO: 25, SEQ ID NO: 28, SEQ ID NO: 29, SEQ ID NO: 34 to SEQ ID NO: 37, SEQ ID NO: 40 to SEQ ID NO: 43, SEQ ID NO: 48, SEQ ID NO: 49, SEQ ID NO: 54 to SEQ ID NO: 59, SEQ ID NO: 64, SEQ ID NO: 65, SEQ ID NO: 70, SEQ ID NO: 71, SEQ ID NO: 74, SEQ ID NO: 75, SEQ ID NO: 78, SEQ ID NO: 79, SEQ ID NO: 82, SEQ ID NO: 83, SEQ ID NO: 88, SEQ ID NO: 89, SEQ ID NO: 92, SEQ ID NO: 93, SEQ ID NO: 96, SEQ ID NO: 98, SEQ ID NO: 101, SEQ ID NO: 102, SEQ ID NO: 104, SEQ ID NO: 105, SEQ ID NO: 108, SEQ ID NO: 111, SEQ ID NO: 112, SEQ ID NO: 113, SEQ ID NO: 116, SEQ ID NO: 119, SEQ ID NO: 121, SEQ ID NO: 123, SEQ ID NO: 125, or SEQ ID NO: 128, wherein the oligonucleotide is capable of hybridizing with the nucleotide sequence of *M. intracellulare* gene, or an oligonucleotide comprising a part or the entire of the sequence complementary to the nucleotide sequence shown in any of SEQ ID NO: 16 to SEQ ID NO: 19, SEQ ID NO: 24, SEQ ID NO: 25, SEQ ID NO: 28, SEQ ID NO: 29, SEQ ID NO: 34 to SEQ ID NO: 37, SEQ ID NO: 40 to SEQ ID NO: 43, SEQ ID NO: 48, SEQ ID NO: 49, SEQ ID NO: 54 to SEQ ID NO: 59, SEQ ID NO: 64, SEQ ID NO: 65, SEQ ID NO: 70, SEQ ID NO: 71, SEQ ID NO: 74, SEQ ID NO: 75, SEQ ID NO: 78, SEQ ID NO: 79, SEQ ID NO: 82, SEQ ID NO: 83, SEQ ID NO: 88, SEQ ID NO: 89, SEQ ID NO: 92, SEQ ID NO: 93, SEQ ID NO: 96, SEQ ID NO: 98, SEQ ID NO: 101, SEQ ID NO: 102, SEQ ID NO: 104, SEQ ID NO: 105, SEQ ID NO: 108, SEQ ID NO: 111, SEQ ID NO: 112, SEQ ID NO: 113, SEQ ID NO: 116, SEQ ID NO: 119, SEQ ID NO: 121, SEQ ID NO: 123, SEQ ID NO: 125, or SEQ ID NO: 128, wherein the oligonucleotide is capable of hybridizing with the nucleotide sequence of *M. intracellulare* gene.

A more preferable specific example of the probe of the present invention includes, for example, an oligonucleotide comprising a part or the entire of the nucleotide sequence shown in any of SEQ ID NO: 16 to SEQ ID NO: 19, SEQ ID NO: 24, SEQ ID NO: 25, SEQ ID NO: 28, SEQ ID NO: 29, SEQ ID NO: 34 to SEQ ID NO: 37, SEQ ID NO: 40 to SEQ ID NO: 43, SEQ ID NO: 48, SEQ ID NO: 49, SEQ ID NO: 58 to SEQ ID NO: 59, SEQ ID NO: 64, SEQ ID NO: 65, SEQ ID NO: 70, SEQ ID NO: 71, SEQ ID NO: 74, SEQ ID NO: 75, SEQ ID NO: 78, SEQ ID NO: 79, SEQ ID NO: 82, SEQ ID NO: 83, SEQ ID NO: 88, SEQ ID NO: 89 SEQ ID NO: 92, SEQ ID NO: 93, SEQ ID NO: 96, SEQ ID NO: 98, SEQ ID NO: 101, SEQ ID NO: 102, SEQ ID NO: 104, SEQ ID NO: 105, SEQ ID NO: 108, SEQ ID NO: 113, SEQ ID NO: 116, SEQ ID NO: 119, SEQ ID NO: 121, SEQ ID NO: 123, SEQ ID NO: 125, or SEQ ID NO: 128, wherein the oligonucleotide is capable of hybridizing with the nucleotide sequence of *M. intracellulare* gene, or an oligonucleotide comprising a part or the entire of the sequence complementary to the nucleotide sequence shown in any of SEQ ID NO: 16 to SEQ ID NO: 19, SEQ ID NO: 24, SEQ ID NO: 25, SEQ ID NO: 28, SEQ ID NO: 29, SEQ ID NO: 34 to SEQ ID NO: 37, SEQ ID NO: 40 to SEQ ID NO: 43, SEQ ID NO: 48, SEQ ID NO: 49, SEQ ID NO: 58 to SEQ ID NO: 59, SEQ ID NO: 64, SEQ ID NO: 65, SEQ ID NO: 70, SEQ ID NO: 71, SEQ ID NO: 74, SEQ ID NO: 75, SEQ ID NO: 78, SEQ ID NO: 79, SEQ ID NO: 82, SEQ ID NO: 83, SEQ ID NO: 88, SEQ ID NO: 89, SEQ ID NO: 92, SEQ ID NO: 93, SEQ ID NO: 96, SEQ ID NO: 98, SEQ ID NO: 101, SEQ ID NO: 102, SEQ ID NO: 104, SEQ ID NO: 105, SEQ ID NO: 108, SEQ ID NO: 113, SEQ ID NO: 116, SEQ ID NO: 119, SEQ ID NO: 121, SEQ ID NO: 123, SEQ ID NO: 125, or SEQ ID NO: 128, wherein the oligonucleotide is capable of hybridizing with the nucleotide sequence of *M. intracellulare* gene.

It should be noted that, the nucleotide sequence shown in SEQ ID NO: 92 to SEQ ID NO: 129 or the nucleotide sequence complementary to the nucleotide sequence shown in SEQ ID NO: 92 to SEQ ID NO: 129 is the nucleotide sequence of the oligonucleotide to be amplified by the PCR using the primer of the present invention. Combinations of the forward primer and the reverse primer, and the SEQ ID NO of the nucleotide sequence to be amplified by the PCR using such a combination of primers are shown collectively in Table 1. For example, the nucleotide sequence shown in SEQ ID NO: 92 is a sequence which is amplified by the PCR using an oligonucleotide having a nucleotide sequence shown in SEQ ID NO: 16 as a forward primer and an oligonucleotide having a nucleotide sequence shown in SEQ NO: 17 as a reverse primer.

TABLE 1

| No. | Forward Primer | Reverse Primer | Sequence to be amplified |
|---|---|---|---|
| 1 | SEQ ID NO: 16 | SEQ ID NO: 17 | SEQ ID NO: 92 |
| 2 | 18 | 19 | 93 |
| 3 | 20 | 21 | 94 |
| 4 | 22 | 23 | 95 |
| 5 | 24 | 25 | 96 |
| 6 | 26 | 27 | 97 |
| 7 | 28 | 29 | 98 |

TABLE 1-continued

| No. | Forward Primer | Reverse Primer | Sequence to be amplified |
|---|---|---|---|
| 8 | 30 | 31 | 99 |
| 9 | 32 | 33 | 100 |
| 10 | 34 | 35 | 101 |
| 11 | 36 | 37 | 102 |
| 12 | 38 | 39 | 103 |
| 13 | 40 | 41 | 104 |
| 14 | 42 | 43 | 105 |
| 15 | 44 | 45 | 106 |
| 16 | 46 | 47 | 107 |
| 17 | 48 | 49 | 108 |
| 18 | 50 | 51 | 109 |
| 19 | 52 | 53 | 110 |
| 20 | SEQ ID NO: 54 | SEQ ID NO: 55 | SEQ ID NO: 111 |
| 21 | 56 | 57 | 112 |
| 22 | 58 | 59 | 113 |
| 23 | 60 | 61 | 114 |
| 24 | 62 | 63 | 115 |
| 25 | 64 | 65 | 116 |
| 26 | 66 | 67 | 117 |
| 27 | 68 | 69 | 118 |
| 28 | 70 | 71 | 119 |
| 29 | 72 | 73 | 120 |
| 30 | 74 | 75 | 121 |
| 31 | 76 | 77 | 122 |
| 32 | 78 | 79 | 123 |
| 33 | 80 | 81 | 124 |
| 34 | 82 | 83 | 125 |
| 35 | 84 | 85 | 126 |
| 36 | 86 | 87 | 127 |
| 37 | 88 | 89 | 128 |
| 38 | 90 | 91 | 129 |

The method for obtaining the probe of the present invention is as described above in the method for obtaining the nucleotide of the present invention.

The probe of the present invention may be labeled with a labeling substance.

As to the labeling substance to be used for labeling the probe of the present invention, any of the known labeling substances such as radioisotope and enzyme, fluorescent substance, luminescent substance, biotin and the like may be used.

The specific example of the labeling substance and the labeling method to be used for labeling the probe of the present invention are as described in the labeling method of the primer of the present invention.

In addition, the labeled probe to be used in the method for detection by the real-time PCR as described later includes the one in which the probe of the present invention has been labeled with a labeling substance usually used in the real-time PCR method. For example, the labeled probe of the present invention in which 5'-terminal is labeled with a reporter fluorescent substance [carboxyfluorescein (FAM), hexachlorofluorescein (HEX), tetrachlorofluorescein (TET) and the like] and 3'-terminal is labeled with a quencher dye [for example, a fluorescent substance such as carboxytetramethylrhodamine (TAMRA), nonfluorescent substance such as Black Hole Quencher dye (BHQ) and 4-((4-(dimethylamino) phenyl)azo)benzoic acid (DABCYL), and the like] is included.

In the method for detection by the TaqMan™ real-time PCR to be described hereinafter, the above described labeled probe can also be used.

The specimen (sample) to be used for detecting *M. intracellulare* involved in the present invention includes various kinds of clinical specimen such as sputum, blood, pharyngeal mucosa, gastric juice, bronchial washing fluid, transbronchial specimen, puncture fluid such as pleural effusion, urine, pus, and the like. In addition, the sample may be a microbial cell isolated and cultured from a specimen; a nucleic acid isolated and purified from such microbial cell; or a nucleic acid amplified by the nucleic acid amplification detection system, and the like.

The extraction and purification of the DNA from the above described samples may be carried out according to the routine procedures usually used for the extraction of DNA of acid-fast bacterium (tuberculosis bacterium) from a specimen.

First, the cell wall of microbial cell in the sample is needed to be broken down. The method for this purpose includes, for example, in the case where the microbial cell is used as a sample, a method for disruption of the membrane structure of tuberculosis bacterium by treating the microbial cell with, for example, surface active agent such as SDS, protein denaturing agent such as guanidine thiocyanate (GTC), and a method of physical disruption of the microbial cell using glass beads and the like.

In the case where the expectorated sputum is used as a sample, as a pretreatment, it is desirable to conduct homogenization of the specimen material by NALC (N-acetyl-L-cysteine)-NaOH method (Kent PT, Kubica GP, Pubric Health Mycobacteriology, A Guide for the Level III Laboratory, U.S. Department of Health and Human Services, Public Health Service, Center for Disease Control, Atlanta, U.S.A., 1985, p. 31-55) according to the recommendation from Center for Disease Control and Prevention (CDC).

After disruption of cell wall of the microbial cell, extraction and purification of DNA may be carried out by a general method for preparation of DNA in this field [phenol-chloroform extraction, ethanol precipitation method, the method for precipitation using isopropanol and the like (R. Boom, C. J. A. SOL, M. M. M. SALIMANS, C. L. JANSEN, P. M. E. WERTHEIM-van DILLEN, J. VAN DER NOORDAA, Rapid and simple method for purification of nucleic acids, J. Clin. Microbiol., 1990, Mar: 28(3), pp. 495-503)].

For extraction and purification of the DNA, since various types of kits for this purpose are commercially available, such kits may be utilized, or the extraction may be carried out according to the routine procedures in this field (for example, phenol-chloroform extraction method, method for precipitation using ethanol, propanol and the like). For example, the extraction and purification of DNA may be carried out using an ion-exchange resin type DNA extraction and purification kit, Genomic-tip produced by Quiagen GmbH, and the like.

Taking a case as an example where the isolated and cultured microbial cells from specimen are used as a sample, the procedure is shown as follows.

For example, colonies grown on the Ogawa's medium are harvested and suspended in sterile distilled water, and the microbial cells are collected by centrifugation, then the collected cells are resuspended in distilled water. Subsequently, after the suspension of microbial cells is autoclaved, pulverization treatment of the cells (physical fracture using glass beads and the like) is carried out; and the disrupted cell suspension is further centrifuged to recover supernatant fluid. The DNA may be extracted and purified from the obtained supernatant fluid.

The method for detecting *M. intracellulare* of the present invention includes, a method for detecting *Mycobacterium intracellulare*, comprising: using an oligonucleotide comprising a part or the entire of the nucleotide sequence shown in any of SEQ ID NO: 1 to SEQ ID NO: 15, or a part or the entire of the sequence complementary to the nucleotide sequence shown in any of SEQ ID NO: 1 to SEQ ID NO: 15, wherein the oligonucleotide is capable of hybridizing with a nucleotide sequence of *Mycobacterium intracellulare* gene as a primer or/and a probe (the method using the primer or/and the probe of the present invention).

The method includes, for example, (A) a method for detection by carrying out the nucleic acid amplification reaction using the oligonucleotide of the present invention as a primer, then detecting the obtained primer extension product;

(B) a method for detection by using the oligonucleotide of the present invention labeled with a labeling substance as a labeled probe.

Each Method will be explained below.

(A) The method for detection by carrying out the nucleic acid amplification reaction using the oligonucleotide of the present invention as a primer, then detecting the obtained primer extension product In the method (A), the method for carrying out the nucleic acid amplification reaction using the oligonucleotide of the present invention as a primer and the nucleic acid in the sample as a template includes, for example, a method in which, using the primer of the present invention and using the nucleic acid in the sample as a template, the nucleic acid amplification by DNA polymerase and the like [for example, polymerase chain reaction (PCR) method; LAMP (Loop-mediated Isothermal Amplification) method (Tsugunori Notomi et al., Nucleic Acid Res., 28, e63, 2000), ICAN™ (Isothermal and Chimeric primer-initiated Amplification of Nucleic acids) method (Rinsho Byori (Clinical Pathology), 51(11), 1061-1067, 2003, Nov), LCR (ligase chain reaction) method (JP-A-4-211399), SDA (strand displacement amplification) method (JP-A-8-19394)] is carried out to allow primer extension. By this method, the sequence of a specific region of the nucleotide sequence of *M. intracellulare* gene can be amplified, and thus *M. intracellulare* can be detected by measuring the resulting primer extension product.

Among the above described methods of the nucleic acid amplification reaction, the PCR method is quoted as the most common method; and an example of the PCR method includes, for example, real time amplification detection method (see, for example, the description in U.S. Pat. No. 5,210,015 and U.S. Pat. No. 5,538,848). In addition, an example of the detection method by the real time amplification detection method includes, for example, real-time PCR detection method.

An example of the real-time PCR detection method includes TaqMan™ real-time PCR method (see, for example, the description in U.S. Pat. No. 5,538,848), MGB Eclipse Probe System method (see, for example, the description in U.S. Pat. No. 5,801,155), Molecular Beacons Probe Technology method (see, for example, the description in U.S. Pat. No. 5,925,517), LUX Fluorogenic Primer method (Invitrogen Corp.), Quenching probe-PCR (QP) method (see, for example, the description in U.S. Pat. No. 6,492,121), and the like.

Specific examples of the primer of the present invention to be used in the nucleic acid amplification reaction such as PCR are as described above.

In addition, a preferable combination of the forward primer and the reverse primer to be used in the nucleic acid amplification reaction include, for example, the combinations shown in the above described Table 1.

For example, in Table 1, for example, the combination of No. 1 indicates "a combination in which the forward primer is an oligonucleotide comprising the nucleotide sequence shown in SEQ ID NO: 16 and the reverse primer is an oligonucleotide comprising the nucleotide sequence shown in SEQ ID NO: 17", or "a combination in which the forward primer is an oligonucleotide comprising the sequence complementary to the nucleotide sequence shown in SEQ ID NO: 16 and the reverse primer is an oligonucleotide comprising the sequence complementary to the nucleotide sequence shown in SEQ ID NO: 17".

Among them, preferable combinations of the forward primer and the reverse primer include, for example, the combinations described in the following Table 2:

TABLE 2

| No. | Foreward Primer | Reverse Primer |
|---|---|---|
| 1 | SEQ ID NO: 16 | SEQ ID NO: 17 |
| 2 | 18 | 19 |
| 3 | 24 | 25 |
| 4 | 28 | 29 |
| 5 | 34 | 35 |
| 6 | 36 | 37 |
| 7 | 40 | 41 |
| 8 | 42 | 43 |
| 9 | 48 | 49 |
| 10 | 54 | 55 |
| 11 | 56 | 57 |
| 12 | 58 | 59 |
| 13 | 64 | 65 |
| 14 | 70 | 71 |
| 15 | 74 | 75 |
| 16 | 78 | 79 |
| 17 | 82 | 83 |
| 18 | 88 | 89 |

Among them, particularly preferable combination includes the combinations of number 1 to 9, and number 12 to 18.

Other reagents such as deoxyribonucleoside triphosphate (dATP, dCTP, dGTP, dTTP) and DNA polymerase, etc. to be used for the nucleic acid amplification reaction such as the real-time PCR using the above described primers may be the reagents commonly used in this field; and the conditions and the procedures and so on, except for the use of the primer and the probe of the present invention, may be carried out according to the general protocol of the PCR.

The method for detection of the primer extension product obtained by the nucleic acid amplification reaction is not particularly limited, and may be the routine procedures commonly used in this field.

For example, various detection methods such as intercalator method; TaqMan™ real-time PCR method (see, for example, the description in U.S. Pat. No. 5,538,848); MGB Eclipse Probe System method (see, for example, the description in U.S. Pat. No. 5,801,155); Molecular Beacons Probe Technology method (see, for example, the description in U.S. Pat. No. 5,925,517); LUX Fluorogenic Primer method (Invitrogen Corporation); Quenching probe-PCR (QP) method (see, for example, the description in U.S. Pat. No. 6,492,121); a method in which, after the nucleic acid amplification reaction is carried out, the primer extension products obtained are subjected to electrophoresis, and detection is performed based on the results of the electrophoresis; a method in which detection is performed by measuring a signal derived from the primer extension product obtained by the nucleic acid amplification reaction using a labeled primer; and the like are included.

Among them, the method commonly used includes, for example, the following methods:

(A-1) intercalator method;
(A-2) TaqMan™ real-time PCR method;

(A-3) a method in which, after the nucleic acid amplification reaction is carried out, the primer extension products obtained are subjected to electrophoresis, and the detection is performed based on the results of the electrophoresis; and (A-4) a method in which the nucleic acid amplification reaction is carried out using a labeled primer and a signal derived from the primer extension product obtained is measured.

Each of these methods will be explained below.

(A-1) Intercalator Method

Conventional intercalator method, in which the real-time PCR is carried out by using known intercalator, can be utilized.

For example, a method in which, using the primer of the present invention and an intercalator, the real-time PCR is carried out by using a conventional intercalator method, is included.

That is, the intercalator is a reagent capable of generating fluorescence by binding specifically to double-stranded DNA, and generates fluorescence when exposed to excitation light. Since the amount of DNA is increased as the result of repeated amplification by the PCR, the intercalator is incorporated into the DNA, and an amount of the intercalator incorporated into the DNA increases in proportion to the amount of the amplification product generated, an amount of primer extension product can be determined by detecting the intensity of fluorescence derived from the intercalator.

In this regard, however, since the intercalator binds to all of the double-stranded DNA, melting curve analysis may be carried out based on the measurement results of the fluorescence intensity, if necessary. Namely, after carrying out the PCR, the fluorescence intensity derived from the intercalator is measured, while temperature of the reaction solution of the PCR is gradually elevated. In the beginning, the PCR amplification product generates fluorescence because it forms double strand. However, when temperature of the reaction solution of PCR reaches to a certain temperature, the amplification products dissociates to a single strand, and the intensity of the fluorescence derived from the intercalator decreases rapidly. Temperature at this point is the melting temperature (Tm value), and is an specific value for a sequence of the primer extension product. Whether the peak of the melting curve analysis corresponds to that of objective specific product or a non-specific product can be determined from this Tm value.

This intercalator method does not require any electrophoretic procedure after the real-time PCR, and therefore, the intercalator method is an effective method in the case where rapid determination is required in the field of clinical testing and the like.

The intercalator to be used in the present invention includes, any type of intercalator usually used in this field can be utilized, and it includes, for example, SYBR™ Green I (product name of Molecular Probes Inc.), ethidium bromide, fluorine, etc.

An example of "the method for detecting *M. intracellulare* through the use of intercalator method" involved in the present invention would be explained as follows:

Using the primer of the present invention and the intercalator (for example, SYBR™ Green I), and using a purified DNA sample purified from a sample as a template, the real-time PCR is carried out using a polymerase such as Taq DNA polymerase. And, by the method of elevating the temperature described above, the fluorescence intensity derived from the intercalator (SYBR™ Green I) intercalated into the primer extension products is measured.

Subsequently, the melting curve is made up by plotting the melting temperature of the primer extension product (double-stranded DNA) as horizontal axis and the first derivation (variation) of the fluorescence intensity as vertical axis. The melting curve analysis of the primer extension product is carried out using the obtained melting curve, and thereby detection of peak is examined. When a single peak is obtained, it can be determined that the sample is positive for *M. intracellulare* (that is, there exists bacterium of *M. intracellulare* or the gene thereof; and hereinafter, the same as above).

In addition, to perform the determination of *M. intracellulare* more precisely, it is preferable to carry out the following method.

That is, the above described measurement is carried out using a sample; the melting curve is made up; and detection of peak is performed. Separately, the same measurement as described above is carried out using a type strain of *M. intracellulare*; the melting curve analysis is carried out; and detection of peak is performed. And, when the result obtained by using a sample is a single peak and the position of the peak is the same or very close to the position of the peak obtained by using the type strain of *M. intracellulare*, it is determined that the sample is positive for *M. intracellulare*.

It should be noted that, if the measurement is carried out using the type strain of *M. intracellulare* and the peak position is determined in advance, it is not necessary to carry out confirmation of the position of the peak for the type strain in every measurements of sample.

In addition, based on the measurement value obtained by the method through the use of the intercalator method, a standard curve can also be made up according to the routine procedure performed in the real-time PCR, and thereby, using the standard curve, the quantity (copy number) of genomic DNA of *M. intracellulare* in a sample can be obtained.

The method of making up the standard curve and the assay method of *M. intracellulare* will be described later.

As an example of the method for detection of *M. intracellulare* by the real-time PCR detection method using the intercalator involved in the present invention, taking a case where *M. intracellulare* is detected using the above described "primer Mint 02_T7pa Fw1" and "primer Mint 02_T7pa Rv1" as an example, the method will be explained as follows.

At first, the purified DNA sample is obtained from the sample by the known method.

Separately, for example, using a DNA synthesizer, an oligonucleotide (Mint 02_T7pa Fw1) consisting of the nucleotide sequence shown in SEQ ID NO: 16 and an oligonucleotide (Mint T7pa 02_Rv1) consisting of the nucleotide sequence shown in SEQ ID NO: 17 are synthesized by the phosphoramidite method.

Using the Mint 02_T7pa Fw1 synthesized above as a forward primer and the Mint T7pa 02_Rv1 as a reverse primer, the real-time PCR is carried out, for example, as follows.

That is, a 10 mM Tris-HCl buffer solution (pH 8.9) containing each 50 nM to 2,000 nM of the primer Mint 02_T7pa Fw1 and the primer Mint T7pa 02_Rv1, about 5,000 times to 100,000 times dilution of the original solution of intercalator [for example, SYBR™ Green I (product name of Molecular Probe Inc.)], 1.0 mM to 4.0 mM $MgCl_2$, KCl, BSA, sodium cholate, 0.005% to 0.2% TritonX-100, 0.2 mM each of dATP, dCTP, dGTP and dTTP, and 10 U/mL to 80 U/mL of polymerase (for example, Taq DNA polymerase) is prepared, and used as a reaction solution for PCR. To this reaction solution for PCR, the purified DNA sample is added, and used as a sample for PCR. Using this sample for PCR, the real-time PCR is carried out using real-time PCR detection equipment and the like. The reaction is repeated for 30 cycles to 50 cycles, and the fluorescence intensity derived from the intercalator (for example, SYBR™ Green I) intercalated in proportion to the amount of amplification of the primer extension products is measured in every one cycle.

After that, the melting curve is made used by plotting the melting temperature of the primer extension product (double-stranded DNA) as horizontal axis and the first derivation (variation) of fluorescence intensity as vertical axis. Using this melting curve, the melting curve analysis of the primer extension product is carried out to detect the peak. When a single peak is obtained, it is determined that the sample is positive for *M. intracellulare*.

More preferably, when the position of peak obtained by the measurement and subsequent melting curve analysis for a sample is appeared at the same or very close to the position of peak obtained by the same measurement and subsequent melting point analysis as described above for the type strain of *M. intracellulare*, it is determined that the sample is positive for *M. intracellulare*.

In addition, as a reference, the DNA derived from *Mycobacterium* genus other than *M. intracellulare* is extracted and purified. The real-time PCR is carried out according to the same method as described above except for the use of this DNA as a template; and intensity of fluorescence of the SYBR™ Green I is measured in the same way; and then the melting curve analysis may be carried out. In this case, as there is no polynucleotide having a nucleotide sequence derived from *M. intracellulare* in the sample, no peak should appear in the melting curve analysis. To make the determination of presence of *M. intracellulare* more assured, the above described control experiment may be conducted in parallel.

Further, by making up a standard curve, number of the genomic DNA (the copy number) of *M. intracellulare* in the sample can be obtained. In addition, as the number is proportional to the number of *M. intracellulare*, the number of *M. intracellulare* in the sample can also be determined.
(A-2) TaqMan™ Real-time PCR Method (TaqMan™ Probe Method)

The TaqMan™ real-time PCR method is a real-time PCR method using a probe in which the 5'-terminal thereof is labeled with a fluorescent (reporter) dye such as, for example, FAM, and the 3'-terminal thereof is labeled with a quencher dye such as, for example, TAMRA, and is a method capable of detecting a small amount of target DNA with high sensitivity and quantitatively (see, for example, the description in U.S. Pat. No. 5,538,848).

That is, this is a method in which using the primer of the present invention and a labeled probe of the present invention which is labeled with a reporter fluorescent dye on the 5'-terminal and with a quencher dye on the 3'-terminal, the PCR is carried out with the nucleic acid in a sample as a template, and then the signal of labeling substance released from said labeled probe is detected.

The principle of the TaqMan™ real-time PCR method is as follows:

In this method, an oligonucleotide probe, which is labeled with a fluorescent dye (reporter) on the 5'-terminal thereof and with a quencher dye on the 3'-terminal thereof, and is capable of hybridizing with a specific region in the target gene, is used. In the aforementioned probe, the fluorescence of the reporter is suppressed by the quencher dye under normal condition. Under the state where this fluorescent labeled probe is hybridized completely with the target gene, the PCR is performed from the outside thereof using a DNA polymerase. As the extension reaction by the DNA polymerase progresses, the fluorescent probe is hydrolyzed away from the 5'-terminal by the exonuclease activity of the DNA polymerase, and the released reporter dye generates the fluorescence. The real-time PCR method is a method of monitoring the intensity from this fluorescence in real time, and thereby, the initial amount of the template DNA can be quantified accurately.

For the forward primer and the reverse primer to be used for the TaqMan™ real-time PCR detection method involved in the present invention, the primer of the present invention is utilized. The preferable primer includes the primer to be used in the nucleic acid amplification reaction such as the above described PCR method, and the preferable combination thereof is also as described above.

The probe to be used for labeling with a fluorescent dye (reporter) on the 5'-terminal thereof and a quencher dye on the 3'-terminal thereof, and which is used for the TaqMan™ real-time PCR detection system involved in the present invention, may be the probe of the present invention described above. In a practical sense, a probe comprising a nucleotide sequence of primer extension product which is anticipated to be obtained when the real-time PCR is carried out by combined use of a selected forward primer and a reverse primer, or a probe comprising a nucleotide sequence designed further from such sequence may be used.

For example, the probe which is used when the real-time PCR is carried out by combined use of Mint 02_T7pa Fw1 and Mint 02_T7pa Rv1 includes an oligonucleotide which comprises a part or the entire of the nucleotide sequence shown in SEQ ID NO: 92 and which is anticipated to be amplified in the real-time PCR.

The reporter fluorescent substance for labeling the 5'-terminal of the labeled probe includes carboxyfluorescein (FAM), hexachlorofluorescein (HEX), tetrachlorofluorescein (TET), Cy5, VIC and the like; and, FAM is used commonly among them.

The quencher dye for labeling the 3'-terminal includes fluorescent substance such as carboxytetramethyl-rhodamine (TAMRA), nonfluorescent substance such as Black Hole Quencher dye (for example, BHQ2), 4-((4-(dimethylamino) phenyl)azo)benzoic acid (DABCYL) and the like; and, TAMRA is used commonly among them.

Other reagents to be used for the TaqMan™ real-time PCR detection system such as deoxyribonucleoside 3-phosphate (dATP, dCTP, dGTP, dTTP), DNA polymerase, etc. may be the same reagents as usually used in the conventional real-time PCR, and the procedure of the real-time PCR may be carried out according to the customary protocol of the real-time PCR except for the use of the primer and the probe of the present invention.

As an example of the method for detecting *M. intracellulare* by the TaqMan™ real-time PCR detection system involved in the present invention, taking a case where *M. intracellulare* is detected using the above described "primer Mint 02_T7pa Fw1" and "primer Mint 02_T7pa Rv1" as an example, the method will be explained as follows.

Firstly, a purified DNA sample is obtained from the sample by known method.

Separately, for example, using a DNA synthesizer, an oligonucleotide (Mint 02_T7pa Fw1) consisting of a nucleotide sequence shown in SEQ ID NO: 16 and an oligonucleotide (Mint 02_T7pa Rv1) consisting of a nucleotide sequence shown in SEQ ID NO: 17 are synthesized by phosphoramidite method.

In addition, from the nucleotide sequence shown in SEQ ID NO: 92 which is anticipated to be amplified by the PCR using a primer pair of Mint 02_T7pa Fw1 and Mint 02_T7pa Rv1 as a primer, a sequence for use as a probe is designed, and an oligonucleotide having this nucleotide sequence is synthesized. The 5'-terminal of this oligonucleotide is coupled with a reporter dye of FAM, and the 3'-terminal with a reporter quencher of TAMRA by routine procedure, and thereby a fluorescence-labeled probe is obtained.

Using the above-synthesized Mint 02_T7pa Fw1 as a forward primer and the Mint 02_T7pa Rv1 as a reverse primer, the real-time PCR is carried out, for example, as follows:

That is, a 10 mM Tris-HCl buffer solution (pH 8.9) containing each 0.1 µM to 2 µM, preferably each 1 µM of the primer Mint 02_T7pa Fw1 and the primer Mint 02_T7pa Rv1, 100 nM to 1000 nM fluorescence-labeled probe, 1.0 mM to 4.0 mM MgCl$_2$, KCl, BSA, sodium cholate, 0.005% to 0.2% TritonX-100, each about 0.2 mM of dATP, dCTP, dGTP and dTTP, and 10 unit/mL to 80 unit/mL of polymerase such as Taq DNA polymerase is prepared, and used as a reaction solution for PCR. To this reaction solution for PCR, the purified DNA sample is added to obtain a sample for PCR.

Using this sample for PCR, the real-time PCR is carried out using appropriate real-time PCR detection equipment and the like. The reaction is repeated 30 times to 50 times of cycle, and at every cycle, the fluorescence intensity derived from the reporter dye is measured.

As for the method for detecting M. intracellulare in this case, when the fluorescence derived from the reporter dye is observed, it is determined that the sample is positive for M. intracellulare.

In addition, in the real-time PCR method, as a standard curve can be made up, the number of genomic DNA (copy number) of M. intracellulare in the sample can be obtained. Further, as the number is proportional to the number of M. intracellulare cell, the number of M. intracellulare in the sample (specimen) can also be determined.

The method for making up the standard curve may be performed according to the routine procedure commonly carried out in the real-time PCR method. For example, using a genomic DNA sample of known copy number derived from M. intracellulare as a standard, a dilution series of concentration (copy number) of the DNA sample for PCR is prepared. After that, using each of the dilution series of the DNA sample for PCR, the real-time PCR is carried out according to the above described method, and the fluorescence intensity derived from the reporter dye is measured. For each concentration of the dilution series of the DNA sample for PCR, the measured value of the fluorescence intensity (Rn, y-axis) is plotted for each cycle number of the PCR (x-axis) to make up an amplification curve. Subsequently, an Rn part where the fluorescence intensity is amplified exponentially is selected, and a threshold line (Th) is drawn. The crossing point of the Th with an amplification curve of each DNA sample for PCR is defined as threshold cycle (Ct) value. After that, the Ct value (y-axis) is plotted for the logarithmic value of the copy number of each DNA sample used for PCR (x-axis), and an approximated curve obtained for each Ct may be used as a standard curve.

When the real-time PCR is carried out by the above described intercalator method, also the standard curve can be made up by the same way based on the obtained measurement value. For example, an amplification curve is made up by plotting the measurement value of the fluorescence intensity derived form the intercalator (Rn, y-axis) for each cycle number of PCR (x-axis). After that, Ct value is obtained by the same way as described above, and the Ct value (y-axis) is plotted for the logarithmic value of the copy number of each used DNA sample for PCR (x-axis), and an approximated curve obtained for each Ct may be used as a standard curve.

For the quantitative determination of the number of the genomic DNA (copy number) of M. intracellulare in a sample, at first, the DNA is isolated and purified from the sample; the real-time PCR for the obtained DNA sample is carried out; and an amplification curve is made up in the same way. The Ct value at the point where the obtained amplification curve crosses the Th obtained when the standard curve is made, is obtained. By fitting the Ct value to the standard curve, the quantity (copy number) of genomic DNA of M. intracellulare in the sample can be obtained.

(A-3) The method in which, after the nucleic acid amplification reaction is carried out, the primer extension products obtained are subjected to electrophoresis, and the detection is performed based on the results of the electrophoresis This method includes, for example, "the method for detectinf M. intracellulare comprising the following steps of:

(i) carrying out nucleic acid amplification reaction using as a primer an oligonucleotide comprising a part or the entire of the nucleotide sequence shown in any of SEQ ID NO: 1 to SEQ ID NO: 15, or a part or the entire of the sequence complementary to the nucleotide sequence shown in any of SEQ ID NO: 1 to SEQ ID NO: 15, wherein the oligonucleotide is capable of hybridizing with the nucleotide sequence of Mycobacterium intracellulare, and using a nucleic acid in a sample as a template;

(ii) carrying out electrophoresis of the primer extension product obtained in above (i); and detecting Mycobacterium intracellulare based on the obtained result from the electrophresis".

A specific example of the nucleic acid amplification reaction is as described above.

Method for determination of the presence of M. intracellulare based on the results of electrophoresis includes, for example, (A-3-1) a method in which the determination is made by confirming a fraction of primer extension product having an objective size (number of base pair);

(A-3-2) a method in which the determination is made by hybridization using labeled probe.

Conditions, operational procedures and the like of the electrophoresis may be in accordance with those of the conventional method usually carried out in this field.

The methods of (A-3-1) and (A-3-2) will be described below.

(A-3-1) The method in which the determination is made by confirming a fraction of primer extension product having objective size (number of base pair)

For example, firstly, an appropriate combination of the forward primer and the reverse primer is selected from the primer of the present invention, and by using the combination, the nucleic acid amplification reaction such as PCR is carried out.

Subsequently, the primer extension product obtained is subjected to electrophoresis. From the combination of the forward primer and the reverse primer used for the nucleic acid amplification reaction, a size (number of base pair) of the primer extension product which is anticipated to be amplified by the PCR is estimated in advance, and confirmation whether the electrophoretic fraction obtained is relevant to the estimated size of amplification product may be made by routine procedures. For example, the method in which said fraction is stained by such a way that the kind of nucleic acid is visualized by staining with ethidium bromide and the like, the primer extension product is confirmed based on its characteristic size (number of base pair), is included. And when the primer extension product having objective number of base pair is confirmed, it may be determined that the sample is positive for *M. intracellulare*.

Specific example of the method for determination by the method of (A-3-1) includes, for example, a method in which, after carrying out the PCR using a combination of the forward primer and the reverse primer listed in the above described Table 1, the primer extension product is subjected to electrophoresis, and when an oligonucleotide having a nucleotide sequence which is anticipated to be amplified by the combination of the primers employed, or a fraction having a size corresponding to the number of the base pair which is anticipated is continued, it may be determined that the sample is positive for *M. intracellulare*.

Specific examples of the method of (A-3-1) are shown collectively in Table 3 below.

That is, for example, the method of number 1 in the Table 3 below is "a method in which, after carrying out the PCR using an oligonucleotide comprising the nucleotide sequence shown in SEQ ID NO: 16 as a forward primer and an oligonucleotide comprising the nucleotide sequence shown in SEQ ID NO: 17 as a reverse primer, the obtained primer extension product is subjected to electrophoresis, and the one which is confirmed to have a fraction of 116 base pair or a fraction of oligonucleotide having a nucleotide sequence shown in SEQ ID NO: 92 is determined to be positive" or "a method in which, after carrying out the PCR using an oligonucleotide comprising the sequence complementary to the nucleotide sequence shown in SEQ ID NO: 16 as a forward primer and an oligonucleotide comprising the sequence complementary to the nucleotide sequence shown in SEQ ID NO: 17 as a reverse primer, the obtained primer extension product is subjected to electrophoresis, and the one which is confirmed a fraction of 116 base pair or a fraction of oligonucleotide comprising a sequence complementary to the nucleotide sequence shown in SEQ ID NO: 92 is determined to be positive".

TABLE 3

| No. | Forward Primer | Reverse Primer | Detection Target Number of base pairs | SEQ ID NO: |
|---|---|---|---|---|
| 1 | SEQ ID NO: 16 | SEQ ID NO: 17 | 116 | SEQ ID NO: 92 |
| 2 | 18 | 19 | 169 | 93 |
| 3 | 20 | 21 | 165 | 94 |
| 4 | 22 | 23 | 200 | 95 |
| 5 | 24 | 25 | 166 | 96 |
| 6 | 26 | 27 | 145 | 97 |
| 7 | 28 | 29 | 170 | 98 |
| 8 | 30 | 31 | 149 | 99 |
| 9 | 32 | 33 | 166 | 100 |
| 10 | 34 | 35 | 182 | 101 |
| 11 | 36 | 37 | 115 | 102 |
| 12 | 38 | 39 | 157 | 103 |
| 13 | 40 | 41 | 137 | 104 |
| 14 | 42 | 43 | 128 | 105 |
| 15 | 44 | 45 | 170 | 106 |
| 16 | 46 | 47 | 189 | 107 |
| 17 | 48 | 49 | 126 | 108 |
| 18 | 50 | 51 | 150 | 109 |
| 19 | 52 | 53 | 130 | 110 |
| 20 | 54 | 55 | 139 | 111 |
| 21 | 56 | 57 | 168 | 112 |
| 22 | 58 | 59 | 138 | 113 |
| 23 | 60 | 61 | 172 | 114 |
| 24 | 62 | 63 | 148 | 115 |
| 25 | 64 | 65 | 131 | 116 |
| 26 | 66 | 67 | 113 | 117 |
| 27 | 68 | 69 | 184 | 118 |
| 28 | 70 | 71 | 169 | 119 |
| 29 | 72 | 73 | 156 | 120 |
| 30 | 74 | 75 | 185 | 121 |
| 31 | 76 | 77 | 184 | 122 |
| 32 | 78 | 79 | 136 | 123 |
| 33 | 80 | 81 | 147 | 124 |
| 34 | 82 | 83 | 174 | 125 |
| 35 | 84 | 85 | 101 | 126 |
| 36 | 86 | 87 | 190 | 127 |
| 37 | 88 | 89 | 174 | 128 |
| 38 | 90 | 81 | 104 | 129 |

Among the methods described in the above Table 3, more preferable method includes, the method of number 1, 2, 5, 7, 10, 11, 13, 14, 17, 20 to 22, 25, 28, 30, 32, 34 and 37 in Table 3.

In addition, among the methods described in the above Table 3, further more preferable method includes, the method of number 1, 2, 5, 7, 10, 11, 13, 14, 17, 22, 25, 28, 30, 32, 34 and 37 in Table 3.

(A-3-2) The method in which the determination is made by hybridization using labeled probe For example, a method in which, a primer extension product obtained by the nucleic acid amplification reaction is subjected to electrophoresis; the electrophoretic fraction obtained is tested for hybridization with a labeled probe which is the probe of the present invention (having the nucleotide sequence which is anticipated to be amplified by the combination of the forward primer and the reverse primer employed) labeled with a labeling substance. When the presence of a fraction hybridized with said labeled probe is confirmed by detecting a signal derived from the labeled probe, it may be determined that the sample is positive for *M. intracellulare*, is included.

Specific examples of the probe to be used and the labeling substance for use in labeling the probe, and the method for labeling the probe are as described above.

Specific preferable examples of these methods are shown collectively in Table 4 below.

For example, in the Table 4, the method of number 1 is "a method in which, after carrying out the PCR using an oligonucleotide comprising the nucleotide sequence shown in SEQ ID NO: 16 as a forward primer and an oligonucleotide comprising the nucleotide sequence shown in SEQ ID NO: 17 as a reverse primer, the obtained primer extension product is subjected to electrophoresis. Subsequently, as to the obtained fraction, hybridization with a labeled probe which is an oligonucleotide labeled with a labeling substance and which comprises a part or the entire of the nucleotide sequence shown in SEQ ID NO: 92 is tested; and when the fraction which has been hybridized with said labeled probe is confirmed by detecting the signal derived from the labeled probe, it is determined to be positive" or "a method in which, after carrying out the PCR using an oligonucleotide comprising a sequence complementary to the nucleotide sequence shown in SEQ ID NO: 16 as a forward primer and an oligonucleotide comprising a sequence complementary to the nucleotide sequence shown in SEQ ID NO: 17 as a reverse primer, the obtained primer extension product is subjected to electrophoresis. Subsequently, as to the obtained fraction, hybridization with a labeled probe which is an oligonucleotide labeled with a labeling substance and which comprises a part or the entire of the sequence complementary to the nucleotide sequence shown in SEQ ID NO: 92 is tested; and when the fraction which has been hybridized with said labeled probe is confirmed by detecting the signal derived from the labeled probe, it is determined to be positive".

TABLE 4

| No. | Forward Primer | Reverse Primer | Nucleotide sequence of probe |
| --- | --- | --- | --- |
| 1 | SEQ ID NO: 16 | SEQ ID NO: 17 | SEQ ID NO: 92 |
| 2 | 18 | 19 | 93 |
| 3 | 20 | 21 | 94 |
| 4 | 22 | 23 | 95 |
| 5 | 24 | 25 | 96 |
| 6 | 26 | 27 | 97 |
| 7 | 28 | 29 | 98 |
| 8 | 30 | 31 | 99 |
| 9 | 32 | 33 | 100 |
| 10 | 34 | 35 | 101 |
| 11 | 36 | 37 | 102 |
| 12 | 38 | 39 | 103 |
| 13 | 40 | 41 | 104 |
| 14 | 42 | 43 | 105 |
| 15 | 44 | 45 | 106 |
| 16 | 46 | 47 | 107 |
| 17 | 48 | 49 | 108 |
| 18 | 50 | 51 | 109 |
| 19 | 52 | 53 | 110 |
| 20 | 54 | 55 | 111 |
| 21 | 56 | 57 | 112 |
| 22 | 58 | 59 | 113 |
| 23 | 60 | 61 | 114 |
| 24 | 62 | 63 | 115 |
| 25 | 64 | 65 | 116 |
| 26 | 66 | 67 | 117 |
| 27 | 68 | 69 | 118 |
| 28 | 70 | 71 | 119 |
| 29 | 72 | 73 | 120 |
| 30 | 74 | 75 | 121 |
| 31 | 76 | 77 | 122 |
| 32 | 78 | 79 | 123 |
| 33 | 80 | 81 | 124 |
| 34 | 82 | 83 | 125 |
| 35 | 84 | 85 | 126 |
| 36 | 86 | 87 | 127 |
| 37 | 88 | 89 | 128 |
| 38 | 90 | 91 | 129 |

Among the methods described in the above Table 4, more preferable method includes, the method of number 1, 2, 5, 7, 10, 11, 13, 14, 17, 20 to 22, 25, 28, 30, 32, 34 and 37 in Table 3.

In addition, among the methods described in the above Table 4, further more preferable method includes, the method of number 1, 2, 5, 7, 10, 11, 13, 14, 17, 22, 25, 28, 30, 32, 34 and 37 in Table 3.

Details of the method for detecting *M. intracellulare* of the present invention by the method of (A-3) will be explained, for example, by taking a case as an example where, after the PCR is carried out using Mint 02_T7pa Fw1 as a forward primer and Mint 02_T7pa Rv1 as a reverse primer and followed by electrophoresis, the detection is performed by the method of confirming a fraction of the primer extension product having the objective base pair size (the method of number 1 in Table 3 of the above (A-3-1)), as follows.

Firstly, purified DNA sample is obtained from a sample by a known method.

Separately, using a DNA synthesizer, Mint 02_T7pa Fw1 (an oligonucleotide consisting of a nucleotide sequence shown in SEQ ID NO: 16) and Mint 02_T7pa Rv1 (an oligonucleotide consisting of a nucleotide sequence shown in SEQ ID NO: 17) are synthesized by the phosphoramidite method.

Using a primer Mint 02_T7pa Fw1 and a primer Mint 02_T7pa Rv1 of the present invention, the PCR is carried out.

The obtained reaction solution after PCR is subjected to agarose gel electrophoresis. Subsequently, after staining the gel with ethidium bromide, the fluorescence generated by UV ray irradiation is detected. Also, the molecular weight marker is electrophoresed in the same time in parallel with the reaction solution, and a length of the detected DNA fragment is calculated by comparing the relative mobility. In the PCR using the Mint 02_T7pa Fw1 as a forward primer and the Mint 02_T7pa Rv1 as a reverse primer, it is anticipated that the DNA fragment with 116 base pair (having a nucleotide sequence shown in SEQ ID NO: 92) in the nucleotide sequence of *M. intracellulare* could be replicated (see, No. 1 in Table 3). Consequently, when a fluorescent band with the size of 116 base pair is confirmed, it may be determined that the sample is positive for *M. intracellulare*.

In addition, in the nucleic acid amplification step of the present invention, a detection method through the use of RNA transcription product can be applied. For example, NASBA (nucleic acid sequence based amplification) method (JP-B-2650159), 3SR (self-sustained sequence replication) method (JP-B-7-114718), TAS (transcription based amplification system) method (JP-A-2-500565: WO 88/10315), TMA (transcription mediated amplification) method (JP-A-11-46778) and the like are included. Among them, the constant temperature nucleic acid amplification methods utilizing a concerted mode of action of reverse transcriptase and RNA polymerase (reaction is carried out under such condition that allows the reverse transcriptase and the RNA polymerase act as concertedly) is a method suitable for the automation of the determination system.

(A-4) The method in which the nucleic acid amplification reaction is carried out using a labeled primer, and a signal derived from the primer extension product obtained is measured.

A method in which using a labeled primer which is the primer of the present invention labeled by the above described method, and using the nucleic acid in the sample as a template, the nucleic acid amplification reaction such as PCR is carried out; and detection/measurement of the signal derived from the obtained primer extension product is carried out; and when the signal is detected, it may be determined that the sample is positive for *M. intracellulare*, is included.

The forward primer and the reverse primer to be used in this method include the ones which are used in the above described PCR method, and the specific examples of preferable primer and preferable combination are also as described above.

In the case of the above described method, after the nucleic acid amplification reaction is carried out, free labeled primers are removed; and the signal derived from the primer extension product is measured; and when the signal is detected, it may be determined that the sample is positive for *M. intracellulare*.

The method for removing free labeled primer includes a method in which, after the primer extension product in the reaction mixture obtained by the nucleic acid amplification reaction is precipitated by the routine procedure of precipitating nucleic acid (ethanol precipitation method, a precipitation method using isopropanol and the like), the supernatant solution which contains non-precipitated free labeled primer is removed, and the like.

In addition, a method for separating the primer extension product from free labeled primer by processing the reaction mixture obtained by the nucleic acid amplification reaction by gel chromatography under appropriate conditions and a method for separation by electrophoresis under appropriate conditions are also included.

(B) A method in which the oligonucleotide of the present invention is labeled with a labeling substance and used as a labeled probe.

Further, the method for detection of *M. intracellulare* of the present invention includes a method in which, an oligonucleotide of the present invention is labeled with a labeling substance and used as a labeled probe, said labeled probe is allowed to hybridize with the nucleic acid in the sample, and after removing the free labeled probe, the signal derived from the hybridized complex is detected.

Specifically, for example, the following methods are included.

(B-1) A detection method in which, the oligonucleotide of the present invention which is bound to the solid carrier is used as a trapping probe, and by performing hybridization with nucleic acid in the sample, the nucleic acid derived from *M. intracellulare* is immobilized on the solid phase (see, for example, the description in JP-A-62-265999).

In the case of this method, the oligonucleotide of the present invention or the solid carrier may be labeled with a labeling substance.

(B-2) A method of performing sandwich assay in which an unlabeled trapping probe of (B-1) and the labeled probe which the probe of the present invention is labeled, are allowed to hybridize with nucleic acid in the sample to form a complex of trapping probe and nucleic acid derived from *M. intracellulare* and labeled probe on the solid carrier, then the signal derived from the labeled probe is measured (see, for example, the description in JP-A-58-40099).

(B-3) A method in which, using a biotin-labeled probe of the present invention, hybridization with nucleic acid in the sample is carried out, and after that, the nucleic acid derived from *M. intracellulare* in the sample is trapped by the avidin-bound carrier.

It should be noted that, as to the reagents to be used for the method for detecting *M. intracellulare* of the present invention, the reagents usually used in this field, for example, buffering agent, stabilizer, preservatives and the like, which do not inhibit the stability of the coexisting reagents nor inhibit the nucleic acid amplification reaction such as PCR and hybridization reaction, can be used. And, concentration of the reagents may be selected as appropriate from the range of concentration usually used in this field.

Specific example of buffer solution includes all kinds the buffer solutions usually used for performing PCR and hybridization reaction, for example, Tris buffer, phosphate buffer, veronal buffer, borate buffer, good buffer and the like; and the pH of the buffer solution is not particularly limited, but generally within the range between pH 5 to pH 9 is preferable.

In addition, as need arises, nucleic acid synthetase (DNA polymerase, RNA polymerase, reverse transcriptase and the like), substrate corresponding to the enzyme (dNTP, rNTP and the like), and additionally, double strand intercalator (ethidium bromide, SYBR™ Green and the like), and alternatively, the signal detection substance such as FAM and TAMRA may be used.

The reagent kit for detection of *M. intracellulare* of the present invention includes "a reagent kit for detecting *M. intracellulare* comprising an oligonucleotide as a primer (the primer of the present invention) or/and a probe (the probe of the present invention) which comprises a part or the entire of the nucleotide sequence shown in any of SEQ ID NO: 1 to SEQ ID NO: 15, or a part or the entire of the sequence complementary to the nucleotide sequence shown in any of SEQ ID NO: 1 to SEQ ID NO: 15, wherein the oligonucleotide is capable of hybridizing with the nucleotide sequence of *M. intracellulare* gene". The primer may be the one which is labeled with a labeling substance. The specific example of the labeling substance is as described above.

Specific examples of the primer of the present invention and the probe of the present invention which constitute the above described kit are as described hereinbefore in the explanation for the "the primer of the present invention" and "the probe of the present invention".

The primer of the present invention may be the one which is labeled with a labeling substance. Specific example of the labeling substance is as described above.

The kit comprising the primer of the present invention also encompasses a composition comprising a pair of the forward primer and the reverse primer. The preferable combination of the forward primer and the reverse primer is as described above.

In addition, the above described kit may further comprise an oligonucleotide of the present invention which is labeled with a labeling substance, as a labeled probe.

Further, the kit of the present invention comprises "a reagent kit for detection of *M. intracellulare* comprising an oligonucleotide as a primer (the primer of the present invention) or/and a probe (the probe of the present invention) which comprises a part or the entire of the nucleotide sequence shown in any of SEQ ID NO: 1 to SEQ ID NO: 15, or a part or the entire of the sequence complementary to the nucleotide sequence shown in any of SEQ ID NO: 1 to SEQ ID NO: 15, wherein the oligonucleotide is capable of hybridizing with the nucleotide sequence of *M. intracellulare* gene". The probe may be the one which is labeled with a labeling substance.

The preferable embodiment and specific examples of the constituent reagents composing these kits are as described above.

It should be noted that, the reagent kit for the detection of *M. intracellulare* of the present invention may comprise, for example, buffering agent, stabilizer, preservatives and the like which do not inhibit the stability of the coexisting reagents and the like nor inhibit the nucleic acid amplification reaction such as PCR and the hybridization reaction. In addition, the concentration of the reagents may be selected as appropriate from the range of concentration usually used in this field.

Specific example of the buffer solution includes all kinds of the buffer solutions usually used for performing the PCR and the hybridization reaction, for example, Tris buffer, phosphate buffer, veronal buffer, borate buffer, good buffer and the like, and the pH is not particularly limited, but generally within the range between pH 5 to pH 9 is preferable.

In addition, as need arises, nucleic acid synthetase (DNA polymerase, RNA polymerase, reverse transcriptase and the like), substrate corresponding to the enzyme (dNTP, rNTP and the like), and additionally, double strand intercalator (ethidium bromide, SYBR™ Green and the like), and alternatively, the signal detection substance such as FAM and TAMRA may be contained in the kit.

Hereinafter, the present invention will be further explained in detail by referring to the following Examples, but the scope of the present invention should not be limited thereto.

It should be noted that all bacteria used in Examples are clinical isolates, and their bacterial species has already been differentiated by the colony morphology and the conventional various biochemical tests on the cultured bacterium.

EXAMPLE

Example 1

Selection of a Clone Derived from *M. intracellulare*

(1) Preparation of DNA Sample Derived from *M. intracellulare*

Firstly, *Mycobacterium intracellulare* JCM6384 (donated from Institute of Physical and Chemical Research), a type strain of *M. intracellulare*, was suspended in purified water and autoclaved (at 120° C., 2 atmospheres for 20 minutes). Subsequently, after the bacterial cell was subjected to disruption treatment (physical disruption using 2 mm diameter glass beads), the suspension was centrifuged, and thus a supernatant solution was obtained. From the supernatant solution obtained, extraction and purification of DNA was carried out using an ion-exchange resin type DNA extraction and purification kit, Genomic-tip, produced by Quiagen GmbH, and purified genomic DNA derived from *M. intracellulare* (*Mycobacterium intracellulare* JCM6384) was obtained.

The obtained purified genomic DNA derived from *M. intracellulare* was adjusted to give final concentration of 400 ng/μL (in 10 mM Tris-HCl buffer, pH 8.9), and used as "DNA sample derived from *M. intracellulare*".

(2) Preparation of Whole Genome Shotgun Library

Using a 24 μg of the DNA sample derived from *M. intracellulare* obtained in the above described (1) as a material, the Whole Genome Shotgun library was prepared by the following method (a modified method from Whole Genome Shotgun method described in Science 2001 Feb. 16; 291 (5507): 1304-1351 Venter et al.).

Firstly, the DNA sample derived from *M. intracellulare* obtained in the above described (1) was fragmented by the treatment using a nebulizer (produced by Invitrogen Corp.) in the presence of 20% final concentration of glycerol under the pressure of 5 kPa to 9 kPa for about 10 minutes. By this treatment, a fraction (DNA fragment) with the objective size of 500 to 1,000 base pairs was recovered efficiently. The fraction obtained was purified using an extraction column produced by Quiagen GmbH.

Subsequently, using the DNA Blunting Kit (produced by Takara Bio Inc.) and through the use of 5'→3' polymerase activity and 3'→5' exonuclease activity of T4 DNA Polymerase, the terminal of obtained DNA fragment was blunted. This DNA fragment was subjected to ligation reaction with blunt-ended pBSII sk$^+$ vector (produced by Stratagene Corp.), and a recombinant DNA of pBSII sk$^+$ vector (amp$^r$) in which the DNA fragment was inserted was prepared.

Using *E. coli* JM109 Competent Cells produced by Takara Bio Inc., transformation of the *E. coli* JM109 Competent Cells was carried out using the above obtained recombinant DNA according to the protocol of the product.

The transformant obtained was cultured in a plate on LB-agarose medium containing 100 μg/mL ampicillin, 0.2 mM IPTG and 40 μg/mL X-Gal. The white colonies were picked up, and thus a Library of the transformant (Whole Genome Shotgun clone Library of genomic DNA derived from *M. intracellulare*) which was introduced by transformation with "the recombinant DNA in which the objective DNA fragment has been inserted" was obtained.

(3) Preparation of Microarray

Using the Library of transformant obtained in the above described (2) (Whole Genome Shotgun clone Library of genomic DNA derived from *M. intracellulare*), the PCR was carried out by the following method, and a probe material to be fixed on a slide glass was prepared.

Firstly, a 10 mM Tris-HCl buffer solution (pH 8.9) containing 1 μM each of primer M13 Primer M1 (produced by Takara Bio Inc.) and primer M13 Primer RV (produced by Takara Bio Inc.), 1.5 mM MgCl$_2$, 80 mM KCl, 500 μg/mL BSA, 0.1% sodium cholate, 0.1% Triton X-100 (polyoxyethylene octylphenyl ether; product name of Rohm and Haas Co., Ltd.), 0.2 mM each of dATP, dCTP, dGTP and dTTP, and 40 unit/mL of Taq DNA polymerase (produced by Nippon Gene Co., Ltd.) was prepared and used as a reaction solution for PCR.

DNA was purified from each transformant (Whole Genome Shotgun clone of genomic DNA derived from *M. intracellulare*) obtained in the above described (2) according to the routine procedure. This purified DNA (which will be used as a template in the PCR later) was added to 20 μL of the reaction solution and suspended, and the suspension prepared was used as a sample for PCR. Using this sample for PCR, 30 cycles of PCR were carried out under the following reaction conditions using the DNA Thermal Cycler (DNA Engine PTC200, produced by MJ Research Inc.).

Reaction conditions of the PCR:
Heat denaturation: 94° C. for 0.5 minutes;
Annealing: 55° C. for 1 minute;
Polymerization reaction: 75° C. for 0.5 minutes.

The obtained PCR amplification product was purified, and then mixed with immobilization buffer (final concentration: 3×SSC).

The final concentration of the PCR product to be spotted was adjusted to give 300 ng/μL, and using a typing instrument (GTMAS Stamp II; produced by Nippon Laser & Electronics Co., Ltd) which was set at 55% in humidity in the instrument, the PCR amplification product obtained above was spotted (the spot diameter: 150 μm to 250 um) on a slide glass (CMT GAPS-II; produced by Corning Inc.). The finished spotted slide glass was transferred to a UV cross-linker (UV Stratalinker 1800; produced by Stratagene Co., Ltd.), and UV light of 150 mJ/cm$^2$ was irradiated to fix the PCR amplification product (having an objective nucleotide sequence of genomic DNA derived from *M. intracellulare*) on the slide glass, and thus the microarray (a microarray made from the Whole Genome Shotgun clone Library of genomic DNA derived from *M. intracellulare* as a material on which 2,000 clones in total were fixed) was prepared.

(4) Fluorescent Labeling of Target Genomic DNA (i) Fluorescent Labeling of Target Genomic DNA Fluorescent labeling of the target genomic DNA was carried out using BioPrime DNA labeling system (produced by Invitrogen Corporation).

Firstly, after a 2 µg of purified genomic DNA derived from *M. intracellulare* obtained in the above described (1) was mixed with 20 µL of random primer solution contained in the product package, the mixture was subjected to heat denaturation treatment (95° C. for 5 minutes), and thereby, the sample solution was obtained. Separately, the genomic DNA was extracted and purified from *M. avium* (IID 585) by routine procedure (genomic DNA for reference), and the same treatment was carried out, and thus the sample solution (reference) was obtained.

Subsequently, to each sample solution obtained, 2 µL of 0.1 M DTT, 2 µL of the mixed solution of dATP/dCTP/dGTP (each 5 mM), 0.8 µL of 2.5 mM dTTP, 1.6 µL of 5 mM Ha-dUTP and 1 µL of Klenow enzyme (40 U/µL) were added and adjusted to give the total volume 50 µL with sterile deionized water, and then the extension reaction was carried out at 37° C. for 3 hours.

An ultrafiltration column, Microcon YM-30 (produced by Millipore Corporation), was set to the attached 1.5 mL tube and the above obtained reaction product was placed on the column and centrifuged at 14,000 rpm for 4 minutes. The concentrated liquid was recovered in a microtube and dried thoroughly using a centrifugal vacuum drier (CentriVap concentrator; produced by LABCONCO Corporation).

The dried reaction product obtained above was added with 10 µL of 50 mM $NaHCO_3$ and mixed, then left for standing at ambient temperature for 2 to 3 minutes.

Separately, 1 mg of Alexa647 (produced by Invitrogen Corporation) or Alexa555 (produced by Invitrogen Corporation) was dissolved in 105 µL of DMSO (dye Solution Alexa647, dye Solution Alexa555). A 10 µL aliquot of this dye Solution Alexa647 was added to the above described reaction product which was obtained by the use of genomic DNA derived from *M. intracellulare*, and incubated (under light shielding) at 40° C. for 60 minutes. In addition, a 10 µL aliquot of this dye Solution Alexa555 was added to the above described reaction product which was obtained by the use of genomic DNA (derived from *M. avium*) for reference, and incubated in the similar way (under light shielding) at 40° C. for 60 minutes.

Further, to the above described each reaction product of post incubation, a 10 µL of 4 M $NH_2OH$ (prepared just before use) was added and mixed, and incubated (under light shielding) for 15 minutes, and thereby the respective labeled products, namely, the labeled product of the Alexa647-labeled genomic DNA derived from *M. intracellulare*, and the labeled product of the Alexa555-labeled genomic DNA derived from *M. avium* were obtained.

An ultrafiltration column, Microcon YM-30 (produced by Millipore Corporation), was set to the attached 1.5 mL tube, and then each of the above obtained labeled products of genomic DNA was placed on the column and centrifuged at 14,000 rpm for 4 minutes, and then the concentrated liquid was recovered in a microtube and dried thoroughly using a centrifugal vacuum drier (CentriVap concentrator; produced by LABCONCO Corporation).

(ii) Fragmentation Process of the Labeled Products

To the labeled products of each genomic DNA in dry state obtained in the above described (i) of (4), a 40 µL of a solution with a composition of the final concentrations of 0.04 M Tris-acetate (pH 8.1), 0.1 M potassium acetate, and 0.03 M magnesium acetate tetrahydrate was added and mixed in suspension. After that, the suspensions were heat-treated at 94° C. for 15 minutes, and the fragmentation products of each labeled genomic DNA with 100 bases to 300 bases were obtained (hereinafter, each referred to as "Alexa555 labeled product" and "Alexa647 labeled product").

It should be noted that, the labeling efficiency (base/dye) was checked through the use of indirect labeling method. As the result, it was confirmed that, with respect to Alexa647, one molecule of the dye per about 100 bases to 200 bases was incorporated. In addition, with respect to Alexa555, it was confirmed that one molecule of the dye per about 150 bases was incorporated.

Each obtained Alexa647-labeled product and Alexa555-labeled product was placed onto an ultrafiltration column of Microcon YM-10 (produced by Millipore Corporation), and then centrifuged at 14,000 rpm for 4 minutes. After that, the concentrated solutions were recovered in a same single microtube, and then dried thoroughly using a centrifugal vacuum drier (CentriVap concentrator; produced by LABCONCO Corporation). Subsequently, the following reagents were added to the microtube and mixed in suspension, and thus, dried labeled product was dissolved.

ArrayHyb Hybridization buffer (produced by SIGMA Co., Ltd.); 40 µL

Salmon sperm DNA (10 mg/mL); 0.5 µL

Formamide; 5 µL

Total; 40 µL to 50 µL

By the procedure described above, a mixed solution of Alexa555/Alexa647-labeled products comprising a fragmentation product of Alexa647-labeled product of genomic DNA derived from *M. intracellulare* and a fragmentation product of Alexa555-labeled product of genomic DNA for reference derived from *M. avium* was obtained.

The obtained mixed solution of Alexa555/Alexa647-labeled products was incubated at 95° C. for 5 minutes, and kept at 70° C. until use for hybridization.

(5) Microarray Hybridization

On the microarray (DNA chip) of Whole Genome Shotgun clone Library of genomic DNA derived from *M. intracellulare* obtained in the above described step (3), the mixed solution of Alexa555/Alexa647-labeled products prepared in the above described (ii) of (4) was placed entirely, and covered with a cover glass so as not to remain air bubble inside. The microarray was set on a Hybri-cassette and placed on Kim Towel mat wetted with distilled water in a Tupperware and closed tightly, and was kept (under light shielding) at 65° C. for 8 hours or more to allow hybridization. After hybridization, the microarray was soaked in a solution of 2×SSC containing 0.1% SDS together with cover glass at room temperature, and shook gently the microarray in the solution to remove the cover glass. Subsequently, after sequential washing with 1×SSC solution containing 0.03% SDS (at 60° C.) for 10 minutes, 0.2×SSC solution (at 42° C.) for 10 minutes and 0.05×SSC solution (at room temperature) for 10 minutes, the microarray was transferred quickly to a new dry rack, and dried immediately by centrifugation at 800 rpm for 5 minutes.

(6) Measurement of Fluorescence Intensity: from Signal Detection to Quantification Using a fluorescence readout scanner GenePix 4000B (produced by Axon Instruments Inc.), the fluorescence intensity on the microarray obtained in the above described (5) which received the microarray-hybridization treatment was measured. On this occasion, in order to analyze the results of competitive hybridization by using Alexa555-labeled product and Alexa647-labeled product, 2 channels, namely 2ch fluorescence (Alexa555, Alexa647) were measured.

The quantification of fluorescence signal was performed using DNASIS™-Array (DNA tip expression image analysis software; produced by Hitachi Software Engineering Co.). That is, according to the operational procedure of the software, automatic spot recognition, background calculation, and normalization of the fluorescence intensity ratio were carried out. In addition, by establishing a threshold limit line of reliability, and avoiding the value lower than this line, a reliable normalized fluorescence intensity ratio was obtained.

Further, based on the fluorescence intensity ratio (Ratio) of Alexa555/Alexa647 detected on the microarray, according to the routine procedure, scatter plot analysis was carried out.

That is, when the fluorescence intensity ratio of Alexa647 to Alexa555 for a certain spot on the microarray is high, it indicates that the DNA fragment (PCR product) of the spot was hybridized more strongly with the Alexa647-labeled product, namely with the genomic DNA derived from *M. intracellulare*. On the other hand, when the fluorescence intensity ratio of Alexa647 to Alexa555 for a certain spot on the microarray is low, it indicates that the DNA fragment of the spot has low specificity for the genomic DNA derived from *M. intracellulare*, but cross-reacted with Alexa555-labeled product, namely with the genomic DNA for reference derived from *M. avium* was observed (hybridized with the genomic DNA for reference derived from *M. avium*).

By this method, the fluorescence intensity ratio for the entire spots of the microarray was calculated. And, the spots having high fluorescence intensity and having high fluorescence intensity ratio of Alexa647 to Alexa555 were selected.

(7) Secondary Screening Using Other *M. intracellulare* Strains

Using various strains of *M. intracellulare* (donated from Japanese Society for Bacteriology) described below in Table 5, by the same way as described in (1), "DNA sample derived from *M. intracellulare*" was prepared from the various strains.

TABLE 5

| Species | Strain | Origin |
|---|---|---|
| M. intracellulare | GTC MY494 | Gifu University School of Medicine |
| M. intracellulare | GTC MY483 | Gifu University School of Medicine |
| M. intracellulare | GTC MY482 | Gifu University School of Medicine |
| M. intracellulare | GTC M91-273 | Gifu University School of Medicine |
| M. intracellulare | GTC M91-269 | Gifu University School of Medicine |
| M. intracellulare | GTC M3278 | Gifu University School of Medicine |
| M. intracellulare | GTC M3274 | Gifu University School of Medicine |
| M. intracellulare | GTC M3273 | Gifu University School of Medicine |
| M. intracellulare | GTC M3272 | Gifu University School of Medicine |
| M. intracellulare | JCM6384 | Institute of Physical and Chemical |

Subsequently, by the same method as described in the above described (i) to (ii) of (4), the labeled products of genomic DNA derived from each *M. intracellulare* strain which was labeled with Alexa647 were obtained, and then the fragmentation products thereof were obtained.

In addition, by the same method as described in the above (i) to (ii) of (4), the labeled product of genomic DNA derived from *M. avium* which was labeled with Alexa555 was obtained, and then the fragmentation products thereof was obtained.

And then, by the same method as described in the above described (i) to (ii) of (4), the mixed solutions of Alexa555/Alexa647-labeled products comprising respective fragmentation products of Alexa647-labeled product of genomic DNA derived from each *M. intracellulare* strain and a fragmentation product of Alexa555-labeled product of genomic DNA for reference derived from *M. avium* were obtained.

Using obtained each mixed solution of Alexa555/Alexa647-labeled products, the competitive hybridization of Alexa555-labeled product and Alexa647-labeled product for the microarray of Whole Genome Shotgun clone of genomic DNA derived from *M. intracellulare* obtained in (3) of Example 1, and the measurement of fluorescence intensity were carried out by the same procedures as described in (5) to (6) above.

Further, by the same method as described in the above (6), based on the fluorescence intensity ratio (Ratio) of Alexa555/Alexa647 detected on the microarray, and according to the routine procedure, scatter plot analysis was carried out.

Based on the obtained results of analysis, by the same method as described in the above (6), the fluorescence intensity ratio for the entire spots of the microarray was calculated, and the spots having high fluorescence intensity and having high fluorescence intensity ratio of Alexa647 to Alexa555 were selected.

(8) Selection of Candidate Clone

Based on the above described result, as a criterion in selecting candidate as a consensus sequence, the spot which hybridized with not less than 7 strains of *M. intracellulare*, but which did not hybridize with *M. avium* was selected from the spots on the microarray of the genome derived from *M. intracellulare*. As a result, 15 spots (candidate clones) were selected.

(9) Determination of Nucleotide Sequence of the Candidate Clone

Subsequently, for the 15 candidate clones selected in the above described (8), sequence analysis was carried out by the following method, and the nucleotide sequence of each clone was determined.

That is, using Big Dye Terminator kit (produced by Applied Biosystems Inc.), sequence analysis was carried out by the following procedure according to the protocol of the product.

Primary candidate DNA (the primary candidate clone); 2 µL (100 ng)

M13 Primer M1; 1 µL (5 pmol)

Premix; 8 µL

To the above mixture, sterile deionized water was added to give a total volume of 20 µL, and then 30 cycles of sequencing reactions under the following reaction conditions were carried out using DNA Thermal Cycler (DNA Engine PTC200; produced by MJ Research Inc.).

96° C. for 2 min→(96° C. for 10 sec→50° C. for 5 sec→60° C. for 4 min)×25→4° C.

The obtained PCR products were purified using gel filtration column produced by QUIAGEN GmbH, and then, using a sequencer (BaseStation; produced by MJ Research Inc.), sequence (nucleotide sequence) mapping for all of the candidate sequences was carried out according to the operation manual attached to the instrument.

The results obtained were searched from the data base (NCBI BLAST and CHEMICAL ABSTRACT), and it was expected that the nucleotide sequence of the 15 primary candidate clones were unregistered new sequence on the data base. This may supposedly be attributed to the fact that *M. intracellulare* is a species whose genome has not been completely sequenced.

The name of the candidate sequence of each determined candidate clone, clone ID number and SEQ ID NO of nucleotide sequence are shown collectively in the following Table 6. In addition, a "Clone ID NO" is the clone ID number which is named by the present inventors.

TABLE 6

| Candidate clone | | |
|---|---|---|
| Name | Clone ID NO | SEQ ID NO |
| Candidate clone A | R02_5h | 1 |
| Candidate clone B | R03_7d | 2 |
| Candidate clone C | R08_8d | 3 |
| Candidate clone D | R23_8h | 4 |
| Candidate clone E | R08_9f | 5 |
| Candidate clone F | R21_11g | 6 |
| Candidate clone G | R23_1h | 7 |
| Candidate clone H | R23_4h | 8 |
| Candidate clone I | R27_10g | 9 |
| Candidate clone J | R27_4g | 10 |
| Candidate clone K | R28_2h | 11 |
| Candidate clone L | R01_3e | 12 |
| Candidate clone M | R03_5d | 13 |
| Candidate clone N | R23_12b | 14 |
| Candidate clone O | R24_8b | 15 |

Example 2

Evaluation of the Ubiquity for Inter-Strain Conservation-1 in the Case where Candidate Sequence A in *M. intracellulare*

(1) Synthesis of the Primer of the Present Invention

Among the candidate clones listed in Table 6 which were determined in (9) of Example 1, based on the result of the sequence analysis (nucleotide sequence) of the candidates clone A (Clone ID NO: R02_5h), and from its candidate sequence A (SEQ ID NO: 1), the nucleotide sequence to be used for the PCR, namely, "5'-CGTGGTGTAGTAGTCA-GCCAGA-3'" (SEQ ID NO: 16; hereinafter referred to as "Mint 02_T7pa Fw1") and "5'-AAAAACGGATCA-GAAGGAGAC-3'" (SEQ ID NO: 17; hereinafter referred to as "Mint 02_T7pa Rv1") were designed using the Web tool Primer3 for primer design (produced by Whitehead Institute for Biomedical Research).

Next, using ABI 392 DNA synthesizer produced by ABI, the oligonucleotide with a designed nucleotide sequence was synthesized by phosphoramidite method. The synthetic procedure was in accordance with the manual supplied by ABI. Deprotection of various oligonucleotides was performed by heating the aqueous ammonia solution of the oligonucleotide at 55° C. overnight.

Subsequently, by performing anion-exchange column chromatography employing Pharmacia FPLC, the synthetic oligonucleotide was purified.

This synthetic oligonucleotide was employed as a primer of the present invention.

(2) Preparation of DNA Sample Derived from *M. intracellulare*

According to the preparation method described in (1) of Example 1, *M. intracellulare* strains (ten strains) listed in the above described Table 5 were processed, and respective DNA was extracted and purified. The respective purified DNA obtained was adjusted to give a final concentration of 1 ng/μL (in 10 mM Tris-HCl buffer solution, pH 8.9), and used as a DNA sample derived from respective *M. intracellulare* strains.

Separately, genomic DNA was extracted and purified from *M. avium* (IID585) by the routine procedure, and was similarly adjusted to give a final concentration of 1 ng/μL (in 10 mM Tris-HCl buffer solution, pH 8.9), and used as a DNA sample derived from *M. avium*.

(3) Real-time PCR (i) Preparation of Reaction Solution for PCR

A 10 mM Tris-HCl buffer solution (pH 8.9) containing each 300 nM of the primer Mint 02_T7pa Fw1 and the primer Mint T7pa 02_Rv1 synthesized in the above (1), 30000 times dilution of stock solution as a final concentration of SYBR™ Green I (product name of Molecular Probe Inc.), 1.5 mM $MgCl_2$, 80 mM KCl, 500 μg/mL BSA, 0.1% sodium cholate, 0.1% TritonX-100, 0.2 mM each of dATP, dCTP, dGTP and dTTP, and 40 U/mL Taq DNA polymerase (produced by Nippon Gene Co., Ltd.) was prepared, and used as a reaction solution for PCR.

(ii) Real-time PCR

Using each DNA sample derived from *M. intracellulare* strains prepared in the above described (2) as a template DNA to be amplified as a target in the PCR, the real-time PCR by the intercalation method was carried out, and quantitative monitoring of the fluorescence was performed.

Firstly, to 20 μL of the reaction solution for PCR prepared in the above described (i) of (3), 1 μL (1 ng) of the DNA sample prepared in the above described (2) was added and used as a sample for PCR.

This sample for PCR was placed in each well of a 96-well reaction plate (MicroAmp Optical 96-well Reaction Plate; produced by Applied Biosystems Japan Ltd.), and the real-time PCR was carried out using a specialized thermal cycler/detector for the TaqMan™ PCR (ABI 7500; produced by Applied Biosystems Japan Ltd.).

That is, after keeping the temperature at 95° C. for 10 minutes, a reaction cycle composed of heating at 95° C. for 15 seconds and 60° C. for 1 minute was repeated for 40 cycles, and the fluorescence intensity derived from SYBR™ Green I which had been intercalated in correlation with the amount of the amplified primer extension product was measured.

In addition, in the above described real-time PCR using forward primer Mint 02_T7pa Fw1 and reverse primer Mint 02_T7pa Rv1, if the nucleotide sequence of the candidate clone A is present in the genomic DNA of each *M. intracellulare* strain used as a template, it is anticipated that the fragment of sequence (116 bases) shown in SEQ ID NO: 92 would be replicated and fluorescence would be detected.

(4) Melting curve analysis

Based on the result of measurement obtained by the PCR using DNA sample derived from respective *M. intracellulare* strains as a template, the melting curve was made up by plotting the melting temperature of the primer extension product (double-stranded DNA) as horizontal axis and the first derivation (variation) of fluorescence intensity as vertical axis, and then detection of peak was carried out.

(5) Result

The results of the melting curve analysis obtained using each DNA sample derived from respective *M. intracellulare* strains were shown collectively in FIG. 1.

As is clear from the results shown in FIG. 1, as the result of the melting curve analysis of the nucleic acid which had been amplified in the presence of SYBR Green by performing the real-time PCR using the primer Mint 02_T7pa Fw1 and the primer Mint 02_T7pa Rv1 of the present invention, and using respective DNA samples obtained from 10 kinds of *M. intracellulare* strains as a template, in each case, fluorescence signal generated as a result of nucleic acid amplification was identified (FIG. 1: *M. intracellulare*), and all cases were determined as positive for *M. intracellulare*. Moreover, all of the peaks of the signal obtained were single peak. Furthermore, the positions of the peaks were almost overlapped.

On the other hand, the real-time PCR was carried out by the same procedures as described in the above (1) to (4) using the DNA sample obtained from *M. avium* which is *Mycobacterium* genus other than *M. intracellulare* as a template, and using the same primers under the same condition. In this case, the fluorescent signal generated as a result of the nucleic acid amplification could not be identified (FIG. 1, *M. avium*), and this case was determined as negative for *M. intracellulare*.

From the above described results, when the PCR is carried out using the primer Mint 02_T7pa Fw1 and the primer Mint 02_T7pa Rv1 of the present invention, and if any of the above described 10 kinds of *M. intracellulare* strains exists,

Example 3

Evaluation of the Ubiquity for Inter-strain Conservation-2 in the Case where Nucleotide Sequence of other Candidate Clones among *M. intracellulare*

Based on the result of analysis of each sequence (nucleotide sequence) of the candidates clone A to O which was determined in (9) of Example 1 and listed in Table 6, and from the nucleotide sequence of each candidate clone, primer sequence for the PCR amplification detection was designed respectively using the Web tool Primer3 for primer design (produced by Whitehead Institute for Biomedical Research).

The name of each candidate sequence, the SEQ ID NO of the nucleotide sequence of the candidate clone, the name of the primer designed based on the nucleotide sequence of the candidate clone (named by the present inventor) and the SEQ ID NO of the nucleotide sequence, and further, the combination of forward primer and reverse primer to be used for performing following PCR were shown collectively in Table 7.

TABLE 7

| Candidate clone | | Designed primer | | | | |
|---|---|---|---|---|---|---|
| Name | SEQ ID NO | Combination No | Forward primer | | Reverse primer | |
| | | | Name | SEQ ID NO | Name | SEQ ID NO |
| Candidate clone A | 1 | 1 | Mint 02_T7pa Fw1 | 16 | Mint 02_T7pa Rv1 | 17 |
| | | 2 | Mint 02_T3pa Fw1 | 18 | Mint 02_T3pa Rv1 | 19 |
| | | 3 | Mint 02_con Fw1 | 20 | Mint 02_con Rv1 | 21 |
| | | 4 | Mint 02_con Fw2 | 22 | Mint 02_con Rv2 | 23 |
| Candidate clone B | 2 | 5 | Mint 04_con Fw1 | 24 | Mint 04_con Rv1 | 25 |
| | | 6 | Mint 04_T3pa Fw1 | 26 | Mint 04_T3pa Rv1 | 27 |
| Candidate clone C | 3 | 7 | Mint 06_T3pa Fw1 | 28 | Mint 06_T3pa Rv1 | 29 |
| | | 8 | Mint 06_con Fw1 | 30 | Mint 06_con Rv1 | 31 |
| | | 9 | Mint 06_con Fw3 | 32 | Mint 06_con Rv3 | 33 |
| Candidate clone D | 4 | 10 | Mint 17_T3pa Fw1 | 34 | Mint 17_T3pa Rv1 | 35 |
| Candidate clone E | 5 | 11 | Mint 07_FWpa Fw1 | 36 | Mint 07_FWpa Rv1 | 37 |
| | | 12 | Mint 07_con Fw1 | 38 | Mint 07_con Rv1 | 39 |
| Candidate clone F | 6 | 13 | Mint 10_FWpa Fw1 | 40 | Mint 10_FWpa Rv1 | 41 |
| | | 14 | Mint 10_con Fw2 | 42 | Mint 10_con Rv2 | 43 |
| | | 15 | Mint 10_RVpa Fw1 | 44 | Mint 10_RVpa Rv1 | 45 |
| | | 16 | Mint 10_con Fw1 | 46 | Mint 10_con Rv1 | 47 |
| Candidate clone G | 7 | 17 | Mint 14_T3pa Fw1 | 48 | Mint 14_T3pa Rv1 | 49 |
| | | 18 | Mint 14_FWpa Fw1 | 50 | Mint 14_FWpa Rv1 | 51 |
| | | 19 | Mint 14_con Fw1 | 52 | Mint 14_con Rv1 | 53 |
| Candidate clone H | 8 | 20 | Mint 15_RVpa Fw1 | 54 | Mint 15_RVpa Rv1 | 55 |
| | | 21 | Mint 15_con Fw1 | 56 | Mint 15_con Rv1 | 57 |
| Candidate clone I | 9 | 22 | Mint 19_T3pa Fw1 | 58 | Mint 19_T3pa Rv1 | 59 |
| | | 23 | Mint 19_FWpa Fw1 | 60 | Mint 19_FWpa Rv1 | 61 |
| | | 24 | Mint 19_con Fw1 | 62 | Mint 19_con Rv1 | 63 |
| Candidate clone J | 10 | 25 | Mint 21_FWpa Fw1 | 64 | Mint 21_FWpa Rv1 | 65 |
| | | 26 | Mint 21_T3pa Fw1 | 66 | Mint 21_T3pa Rv1 | 67 |
| | | 27 | Mint 21_con Fw1 | 68 | Mint 21_con Rv1 | 69 |
| Candidate clone K | 11 | 28 | Mint 23_con Fw1 | 70 | Mint 23_con Rv1 | 71 |
| | | 29 | Mint 23_FWpa Fw1 | 72 | Mint 23_FWpa Rv1 | 73 |
| Candidate clone L | 12 | 30 | Mint 01con Fw1 | 74 | Mint 01con Rv1 | 75 |
| | | 31 | Mint 01_T7pa Fw1 | 76 | Mint 01_T7pa Rv1 | 77 |
| Candidate clone M | 13 | 32 | Mint 03_con Fw1 | 78 | Mint 03_con Rv1 | 79 |
| | | 33 | Mint 03_con Fw2 | 80 | Mint 03_con Rv2 | 81 |
| Candidate clone N | 14 | 34 | Mint 12_FWpa Fw1 | 82 | Mint 12_FWpa Rv1 | 83 |
| | | 35 | Mint 12_RVpa Fw1 | 84 | Mint 12_RVpa Rv1 | 85 |
| | | 36 | Mint 12_con Fw1 | 86 | Mint 12_con Rv1 | 87 |
| Candidate clone O | 15 | 37 | Mint 18con Fw1 | 88 | Mint 18con Rv1 | 89 |
| | | 38 | Mint 18con Fw2 | 90 | Mint 18con Rv2 | 91 | detection of the strain is possible, and moreover it turns out that specific detection of *M. intracellulare* species can be performed. And from this result, it was also suggested that the candidate sequence A used as the target has a high possibility of being a consensus sequence of *M. intracellulare*.

Subsequently, oligonucleotide of each designed nucleotide sequence was synthesized and purified by the same method as (1) of Example 2. Using this synthetic oligonucleotide as a primer of the present invention, and in the combination of a forward primer and a reverse primer as described in Table 7, preparation of DNA sample, the real-time PCR, and melting curve analysis were carried out by the same method as described in (2) to (4) of Example 2.

As a result, in the real-time PCR carried out using any of the combination of the primers, similar melting curves as FIG. 1 of Example 2 was obtained. That is, using the combination of primers described in Table 7, the real-time PCR was carried out using each DNA sample obtained from 10 kinds of *M. intracellulare* strains listed in Table 5 as a template, and melting curve analysis of the nucleic acid which was amplified in the presence of SYBR Green I was carried out. As a result, in any case, the fluorescence signal generated as a result of nucleic acid amplification was identified, and determined to be positive for *M. intracellulare*. Moreover, all of the peaks of the signal obtained were single peak. Furthermore, the positions of the peaks were almost overlapped.

In addition, by the same way as Example 2, using the DNA sample obtained from *M. avium* which is *Mycobacterium* genus other than *M. intracellulare* as a template, the real-time PCR was carried out using the same primers. In this case, the fluorescent signal generated as a result of the nucleic acid amplification could not be identified, and the all were determined as negative for *M. intracellulare*.

From the above described results, when the PCR is carried out using the primer of the present invention as described in Table 7, and if any of the above described 10 kinds of *M. intracellulare* strains is present, it is possible to detect the strain; moreover it turns out that specific detection of *M. intracellulare* species can be performed. And from this result, it was also suggested that all of the candidate sequence A to O used as the target has a high possibility of being a consensus sequence of *M. intracellulare*.

Example 4

Evaluation of Specificity of the Candidate Clone A for *M. intracellulare*

(1) Synthesis of the Primer of the Present Invention

The same primer Mint 02_T7pa Fw1 and the same primer Mint 02_T7pa Rv1 as those used in the above described (1) of Example 2 were synthesized by the same method using the same instrument as used in (1) of Example 2.

These were used as a primer of the present invention.

(2) Preparation of DNA Sample Derived from Each Bacterium

The DNA sample derived from each strain of *Mycobacterium* genus and from *Escherichia coli* shown below was prepared by the following methods, respectively.

a: *Escherichia coli* (*E. coli*) (ATCC11775)
  b: *Mycobacterium tuberculosis* (TMC102 [H37Rv])
  c: *Mycobacterium kansasii* (ATCC12478)
  d: *Mycobacterium marinum* (ATCC927)
  e: *Mycobacterium simiae* (ATCC25275)
  f: *Mycobacterium scrofulaceum* (ATCC19981)
  g: *Mycobacterium gordonae* (ATCC14470)
  h: *Mycobacterium szulgai* (ATCC35799)
  i: *M. avium* (IIID 585)
  j: *M. intracellulare* (ATCC 13950)
  k: *Mycobacterium gastri* (ATCC 15754)
  l: *Mycobacterium xenopi* (ATCC 19250)
  m: *Mycobacterium nonchrornogenicum* (ATCC19530)
  n: *Mycobacterium terrae* (ATCC 15755)
  o: *Mycobacterium triviale* (ATCC23292)
  p: *Mycobacterium fortuitum* (ATCC6841)
  q: *Mycobacterium chelonei* (ATCC35752)
  r: *Mycobacterium abscessus* (ATCC19977)
  s: *Mycobacterium peregrinum* (ATCC 14467)

Firstly, as to *Mycobacterium tuberculosis*, a purified genomic DNA was obtained from Mycos Research, LLC, and was used as a purified DNA.

As to *M. avium*, the type strain (IIID 585) was obtained from The Institute of Medical Science, The University of Tokyo; and as to the other bacteria, the strains were obtained from American Type Culture Collection (ATCC). And the DNA thereof was extracted and purified by the following method. Bacteria used were all type strain, and their bacterial species have already been differentiated by the colony morphology and the conventional various biochemical examinations, etc. for the cultured bacterium.

That is, as to the bacteria of *Mycobacterium* genus, at first, the colonies grown on the Ogawa's medium were collected and suspended in purified water, and then autoclaved (at 120° C. under 2 atmospheres for 20 minutes). Subsequently, the microbial cells were subjected to diruption treatment (physical fracture using 2 mm diameter of glass beads), followed by centrifugation, and the supernatant solution was obtained. From the obtained supernatant solution, the extraction and purification of DNA was carried out using an ion-exchange resin type DNA extraction and purification kit, Genomic-tip produced by QUIAGEN GmbH.

In addition, as to *E. coli*, according to the routine procedure of *E. coli* DNA extraction method, the extraction and purification of the DNA were carried out.

Each of the purified DNA obtained was adjusted to give final concentration of 1 ng/µL (in 10 mM Tris-HCl buffer, pH 8.9), and used as a DNA sample derived from respective bacteria.

(3) Real-time PCR

The real-time PCR was carried out by the same procedure as described in (3) of Example 2 except for using the DNA derived from each bacterium prepared in the above described (2) as a template.

(4) Melting Curve Analysis

By the same procedures as described in (4) of Example 2, and based on the result of measurement obtained by the PCR using DNA sample derived from respective bacteria as a template, the melting curve was depicted by plotting the melting temperature of the primer extension product (double-stranded DNA) as horizontal axis and the first derivation (variation) of fluorescence intensity as vertical axis, and then detection of peak was carried out.

(5) Result

The results of the melting curve analysis obtained using each DNA sample derived from respective bacteria were summarized to one graph, and shown in FIG. 2.

As is clear from the results shown in FIG. 2, as the result of the melting curve analysis of the nucleic acid which had been amplified in the presence of SYBR Green I by the real-time PCR using the primer Mint 02_T7pa Fw1 and the primer Mint 02_T7pa Rv1 of the present invention, only when the real-time PCR was carried out using the DNA sample derived from *M. intracellulare* as a template, the fluorescence signals generated as a result of nucleic acid amplification could be identified (FIG. 2: *M. intracellulare*), and could be determined to be positive for *M. intracellulare*.

On the other hand, as is clear from FIG. 2, when the real-time PCR was carried out in the same way using the DNA sample derived from bacteria of *Mycobacterium* genus other than *M. intracellulare* and the DNA sample derived from a bacterium of other genus of *E. coli* as a template, and using a combination of the same primers, corresponding fluorescent signal could not be detected (FIG. 2: other species), and all the sample could be determined as negative for M. intracellulare.

Furthermore, as is clear from FIG. 2, from the fact that a single clear peak was obtained as the result of the melting curve analysis when the DNA sample derived from M. intracellulare was used as a template, it turns out that the detection method carried out is a method having an extremely high specificity for M. intracellulare.

From the above results, it turns out that by using the oligonucleotide of the present invention as a primer for PCR, M. intracellulare can be detected specifically. In addition, since the detection by nucleic acid amplification such as PCR can be expected to provide a high sensitivity, isolation of bacterium is not necessary, and the clinical specimen can be used directly for the detection. Therefore, the detection of M. intracellulare can be finished within a day at the longest, whereas the conventional method in which the bacterial culture is required before performing detection have taken several weeks.

Example 5

Evaluation of Specificity-2 of the Other Candidate Clones for M. intracellulare (1) Synthesis of the Primer of the Present Invention Using the same instrument as used in (1) of Example 2 and by the same method, the oligonucleotides listed in the above described Table 7 except for primer Mint 02_T7pa Fw1 and primer Mint 02_T7pa Rv1 were synthesized and purified.

These synthetic oligonucleotides were used as a primer of the present invention.

(2) Preparation of DNA Samples Derived from Each Bacterium

DNA samples derived from each bacterium were prepared using the same bacteria as having used in Example 4 by the same procedures as used in (2) of Example 4.

(3) Real-time PCR

Using the primers which were designed and synthesized in the above described (1) and in the combination as described in the above table 7, the real-time PCR was carried out by the same procedure as described in (3) of Example 2 except for using the DNA sample derived from each bacterium prepared in the above described (2) as a template.

(4) Melting Curve Analysis

By the same procedures as described in (4) of Example 2, and based on the result of measurement obtained by the PCR using DNA sample derived from respective bacteria as a template, the melting curve was depicted by plotting the melting temperature of the primer extension product (double-stranded DNA) as horizontal axis and the first derivation (variation) of fluorescence intensity as vertical axis, and then detection of peak was carried out.

(5) Result

As is the similar result from Example 4, when the melting curve analysis of the nucleic acid amplified by the real-time PCR in the presence of SYBR Green I using the primer of the present invention listed in the above described Table 7, in any case where any of the combination of the primers described in Table 7 is employed, the fluorescent signal generated as a result of nucleic acid amplification could be identified only when the real-time PCR is carried out using the DNA sample derived from M. intracellulare as a template, and could be determined as positive for M. intracellulare.

On the other hand, when the real-time PCR was carried out in the same way using the DNA sample derived from bacteria of Mycobacterium genus other than M. intracellulare and the DNA sample derived from a bacterium of other genus of E. coli as a template, and using any combination of the same primers described in Table 7, corresponding fluorescent signal could not be detected, and all the samples could be determined as negative for M. intracellulare.

Furthermore, a single clear peak was obtained as the result of the melting curve analysis when the DNA sample derived from M. intracellulare was used as a template, as is the similar result from Example 4, it turns out that the detection method carried out is a method having an extremely high specificity for M. intracellulare.

From the above results, it turned out that by using the oligonucleotide of the present invention as a primer for PCR, M. intracellulare can be detected specifically. In addition, since the detection by nucleic acid amplification such as PCR can be expected to provide a high sensitivity, isolation of bacterium is not necessary, and the clinical specimen can be used directly for the detection. Therefore, the detection of M. intracellulare can be finished within a day at the longest, whereas the conventional method in which the bacterial culture is required before performing detection have taken several weeks.

Example 6

Minimum Detection Sensitivity Test

Through the use of real time detection method, verification of the detection sensitivity at the time of targeting the nucleotide sequence of candidate clone J (Clone ID NO: R27_4g) was carried out.

(1) Synthesis of the Primer of the Present Invention

Among the candidate clones listed in Table 6 determined in (9) of Example 1, based on the result of the sequence analysis (nucleotide sequence) of the candidates clone J (Clone ID NO: R27_4g), and from the candidate sequence J (SEQ ID NO: 10), the nucleotide sequence to be used for the PCR, namely, "5'-CAGCGACCGTGTGTTCTTAC-3'" (SEQ ID NO: 64; hereinafter referred to as "Mint 21_FWpa Fw1") and "5'-GGAAGTGGGCGGTATCCT-3'" (SEQ ID NO: 65; hereinafter referred to as "Mint 21_FWpa Rv1") were designed using the Web tool Primer3 for primer design (produced by Whitehead Institute for Biomedical Research).

Next, using ABI 392 DNA synthesizer produced by ABI, the oligonucleotide with a designed nucleotide sequence was synthesized by phosphoramidite method. The synthetic procedure was in accordance with the manual supplied by ABI. Deprotection of various oligonucleotides was performed by heating the aqueous ammonia solution of the oligonucleotide at 55° C. overnight.

Subsequently, by performing anion-exchange column chromatography employing Pharmacia FPLC, the synthetic oligonucleotide was purified. This synthetic oligonucleotide was used as a primer of the present invention.

(2) Preparation of the DNA Sample for PCR

According to the preparation method described in (1) of Example 1, purified genomic DNA derived from M. intracellulare was obtained from M. intracellulare JCM6384, the DNA sample derived from M. intracellulare was prepared.

Absorbance of the prepared DNA sample derived from M. intracellulare was measured. The amount of genomic DNA (copy number of the genome) in the sample was determined by comparing the obtained absorbance with measurement value obtained by measuring absorbance by the same procedure using the genomic DNA of M. intracellulare JCM6384 of known concentration as a sample. A $10^8$ copy/μL of the genomic DNA was obtained.

Subsequently, the DNA sample was diluted using 10 mM Tris-HCl buffer, pH 8.9 to a dilution series of $10^5$, $10^4$, $10^3$, $10^2$, 10, and 5 copy/μL, and used as a DNA sample for PCR.
(3) Real-time PCR
(i) Preparation of Reaction Solution for PCR A 10 mM Tris-HCl buffer solution (pH 8.9) containing each 300 nM of the primer Mint 02_T7pa Fw1 and the primer Mint T7pa 02_Rv1 synthesized in the above (1), 30000 times dilution of stock solution as a final concentration of SYBR™ Green I (product name of Molecular Probe Inc.), 1.5 mM $MgCl_2$, 80 mM KCl, 500 μg/mL BSA, 0.1% sodium cholate, 0.1% TritonX-100, 0.2 mM each of dATP, dCTP, dGTP and dTTP, and 40 U/mL Taq DNA polymerase (produced by Nippon Gene Co., Ltd.) was prepared, and used as a reaction solution for PCR.
(ii) Real-time PCR To a 20 of the reaction solution for PCR prepared in the above described (i) of (3), 1 μL of DNA sample for PCR prepared in the above described (2) was added and used as a sample for PCR.

This sample for PCR was placed in each well of a 96-well reaction plate (MicroAmp Optical 96-well Reaction Plate; produced by Applied Biosystems Japan Ltd.), and the real-time PCR was carried out using a specialized thermal cycler/detector for the TaqMan™ PCR (ABI 7500; produced by Applied Biosystems Japan Ltd.).

That is, after keeping the temperature at 95° C. for 10 minutes, a reaction cycle composed of heating at 95° C. for 15 seconds and 60° C. for 1 minute was repeated for 40 cycles, and the fluorescence intensity derived from SYBR™ Green I which had been intercalated in correlation with the amount of the amplified primer extension product was measured.

It should be noted that, fluorescence intensity was measured by using a function of the thermal cycler used for the measurement to digitalize relative fluorescent intensity ratio, for each of the 96 well reaction plates used for the measurement.
(4) Result From the experimental data obtained, according to the routine procedure commonly performed in the real-time PCR method, for each concentration of DNA sample for PCR, an amplification curve was made up by plotting the fluorescence intensity derived from SYBR Green I (Rn, y-axis) for each cycle number of the PCR (x-axis). The obtained amplification curve was shown in FIG. 3.

Subsequently, from the obtained amplification curve, standard curve was made up by the following method.

That is, an Rn part where the fluorescence intensity amplified exponentially in the obtained amplification curve (FIG. 3) was selected, and a Threshold line (Th) was drawn. The crossing point of the Th with the fluorescence intensity of each DNA sample for PCR was defined as Threshold cycle (Ct) value. After that, the Ct value (y-axis) was plotted for the copy number of the genome of each used DNA sample for PCR (x-axis, logarithmic value), and the approximated curve obtained for each Ct was used as a standard curve. The standard curve obtained is shown in FIG. 4.

$$y=-3.356x+35.57$$

$$R^2=0.999$$

In consequence, from the fact that the fluorescence was detected by the real-time PCR, it turns out that M. intracellulare can be detected by carrying out the real-time PCR using the oligonucleotide of the present invention as a primer.

In addition, it also turns out that, as the standard curve has become available, quantitative determination of M. intracellulare is possible by the real-time PCR using the primer and the probe of the present invention. Further, it turns out from FIG. 4 that the real-time PCR method using the primer and the probe of the present invention can detect M. intracellulare even under the condition where only 5 copies of the genomic DNA of M. intracellulare are present as initial quantity.

In addition, the amplification efficiency of PCR by this method was numerically 98.4%, and thus, high reactivity was confirmed.

Furthermore, when the experiment was carried out similarly using the combination of other primers listed in the above described Table 7, almost equivalent results could be obtained. From the facts described above, it became clear that the detection and quantification of M. intracellulare can be performed by performing the real-time PCR targeting for the candidate sequences A to O.

INDUSTRIAL APPLICABILITY

According to the method for detection of M. intracellulare by using the primer or/and the probe of the present invention, the detection of M. intracellulare can be performed more rapidly and with higher accuracy, yet specifically as compared with the conventional detection method.

Moreover, according to the method for detecting M. intracellulare using the primer of the present invention, it is possible to detect in the case where any of a plurality of serotypes or strains of M. intracellulare exists by single operation. In addition, this made the detecting operation simplified and the time required for diagnosis also shortened; accordingly this method is quite useful in particular in the field of clinical testing where rapid determination is required.

What is claimed is:

1. A primer pair for detecting *Mycobacterium intracellulare*, comprising:

a forward primer and a reverse primer selected from a group consisting of:

(a) a forward primer consisting of SEQ ID No: 16, and a reverse primer consisting of SEQ ID NO: 17;
(b) a forward primer consisting of SEQ ID No: 18, and a reverse primer consisting of SEQ ID NO: 19;
(c) a forward primer consisting of SEQ ID No: 20, and a reverse primer consisting of SEQ ID NO: 21;
(d) a forward primer consisting of SEQ ID No: 22, and a reverse primer consisting of SEQ ID NO: 23;
(e) a forward primer consisting of SEQ ID No: 28, and a reverse primer consisting of SEQ ID NO: 29;
(f) a forward primer consisting of SEQ ID No: 30, and a reverse primer consisting of SEQ ID NO: 31;
(g) a forward primer consisting of SEQ ID No: 32, and a reverse primer consisting of SEQ ID NO: 33;
(h) a forward primer consisting of SEQ ID No: 34, and a reverse primer consisting of SEQ ID NO: 35;
(i) a forward primer consisting of SEQ ID No: 40, and a reverse primer consisting of SEQ ID NO: 41;
(j) a forward primer consisting of SEQ ID No: 42, and a reverse primer consisting of SEQ ID NO: 43;
(k) a forward primer consisting of SEQ ID No: 44, and a reverse primer consisting of SEQ ID NO: 45;
(l) a forward primer consisting of SEQ ID No: 46, and a reverse primer consisting of SEQ ID NO: 47;
(m) a forward primer consisting of SEQ ID No: 48, and a reverse primer consisting of SEQ ID NO: 49;
(n) a forward primer consisting of SEQ ID No: 50, and a reverse primer consisting of SEQ ID NO: 51;
(o) a forward primer consisting of SEQ ID No: 52, and a reverse primer consisting of SEQ ID NO: 53;
(p) a forward primer consisting of SEQ ID No: 58, and a reverse primer consisting of SEQ ID NO: 59;
(q) a forward primer consisting of SEQ ID No: 60, and a reverse primer consisting of SEQ ID NO: 61;
(r) a forward primer consisting of SEQ ID No: 62, and a reverse primer consisting of SEQ ID NO: 63;
(s) a forward primer consisting of SEQ ID No: 64, and a reverse primer consisting of SEQ ID NO: 65;
(t) a forward primer consisting of SEQ ID No: 66, and a reverse primer consisting of SEQ ID NO: 67;
(u) a forward primer consisting of SEQ ID No: 68, and a reverse primer consisting of SEQ ID NO: 69;
(v) a forward primer consisting of SEQ ID No: 78, and a reverse primer consisting of SEQ ID NO: 79;
(w) a forward primer consisting of SEQ ID No: 80, and a reverse primer consisting of SEQ ID NO: 81; and
(x) a forward primer consisting of SEQ ID No: 46, and a reverse primer consisting of a sequence consisting of SEQ ID NO: 45 and two additional nucleotides on the 5' end of SEQ ID NO: 45;

wherein a labeling substance is bound to at least one of the primers in each primer pair via a covalent bond or a linker, and wherein the labeling substance is a radioisotope, an enzyme, a fluorescent substance, a luminescent substance, or a biotin.

2. A reagent kit for detecting *Mycobacterium intracellulare*, comprising:

a first container comprising a primer pair consisting of a forward primer and a reverse primer selected from a group consisting of:

(a) a forward primer consisting of SEQ ID No: 16, and a reverse primer consisting of SEQ ID NO: 17;
(b) a forward primer consisting of SEQ ID No: 18, and a reverse primer consisting of SEQ ID NO: 19;
(c) a forward primer consisting of SEQ ID No: 20, and a reverse primer consisting of SEQ ID NO: 21;
(d) a forward primer consisting of SEQ ID No: 22, and a reverse primer consisting of SEQ ID NO: 23;
(e) a forward primer consisting of SEQ ID No: 28, and a reverse primer consisting of SEQ ID NO: 29;
(f) a forward primer consisting of SEQ ID No: 30, and a reverse primer consisting of SEQ ID NO: 31;
(g) a forward primer consisting of SEQ ID No: 32, and a reverse primer consisting of SEQ ID NO: 33;
(h) a forward primer consisting of SEQ ID No: 34, and a reverse primer consisting of SEQ ID NO: 35;
(i) a forward primer consisting of SEQ ID No: 40, and a reverse primer consisting of SEQ ID NO: 41;
(j) a forward primer consisting of SEQ ID No: 42, and a reverse primer consisting of SEQ ID NO: 43;
(k) a forward primer consisting of SEQ ID No: 44, and a reverse primer consisting of SEQ ID NO: 45;
(l) a forward primer consisting of SEQ ID No: 46, and a reverse primer consisting of SEQ ID NO: 47;
(m) a forward primer consisting of SEQ ID No: 48, and a reverse primer consisting of SEQ ID NO: 49;
(n) a forward primer consisting of SEQ ID No: 50, and a reverse primer consisting of SEQ ID NO: 51;
(o) a forward primer consisting of SEQ ID No: 52, and a reverse primer consisting of SEQ ID NO: 53;
(p) a forward primer consisting of SEQ ID No: 58, and a reverse primer consisting of SEQ ID NO: 59;
(q) a forward primer consisting of SEQ ID No: 60, and a reverse primer consisting of SEQ ID NO: 61;
(r) a forward primer consisting of SEQ ID No: 62, and a reverse primer consisting of SEQ ID NO: 63;
(s) a forward primer consisting of SEQ ID No: 64, and a reverse primer consisting of SEQ ID NO: 65;
(t) a forward primer consisting of SEQ ID No: 66, and a reverse primer consisting of SEQ ID NO: 67;
(u) a forward primer consisting of SEQ ID No: 68, and a reverse primer consisting of SEQ ID NO: 69;
(v) a forward primer consisting of SEQ ID No: 78, and a reverse primer consisting of SEQ ID NO: 79;
(w) a forward primer consisting of SEQ ID No: 80, and a reverse primer consisting of SEQ ID NO: 81; and (x) a forward primer consisting of SEQ ID No: 46, and a reverse primer consisting of a sequence consisting of SEQ ID NO: 45 and two additional nucleotides on the 5' end of SEQ ID NO: 45;

wherein a labeling substance is bound to at least one of the primers in each primer pair via a covalent bond or a linker, and wherein the labeling substance is an enzyme, a fluorescent substance, luminescent substance, or a biotin.

3. The reagent kit according to claim 2, further comprising a second container
wherein the second container comprises a nucleic acid synthetase and at least one reagent selected from a buffering agent, a stabilizer, and a preservative; or
wherein the second container comprises a substrate for a nucleic acid synthetase and at least one reagent selected from a buffering agent, a stabilizer, and a preservative; or
wherein the second container comprises a double strand intercalator and at least one reagent selected from a buffering agent, a stabilizer, and a preservative; or
wherein the second container comprises a signal detection substance and at least one reagent selected from a buffering agent, a stabilizer, and a preservative.

4. The reagent kit according to claim 2, further comprising a third container
wherein the third container comprises a probe consisting of:
one of the nucleotide sequences of SEQ ID NOS: 1, 3, 4, 6, 7, 9, 10, or 13; or the full complement of one of the nucleotide sequences SEQ ID NOS: 1, 3, 4, 6, 7, 9, 10, or 13; or
15 to 50 contiguous bases or 100 contiguous bases to the full length of the nucleotide sequence consisting of one of SEQ ID NOS: 1, 3, 4, 6, 7, 9, 10, or 13; or 15 to 50 contiguous bases or 100 contiguous bases to the full length of the full complement of the nucleotide sequence consisting of one of SEQ ID NOS: 1, 3, 4, 6, 7, 9, 10, or 13; and
wherein the probe is capable of hybridizing with the genomic nucleotide sequence of *Mycobacterium intracellulare* gene.

5. A reagent kit for detecting *Mycobacterium intracellulare*, comprising:
(i) a first container comprising a primer pair consisting of a forward primer and a reverse primer selected from a group consisting of:
(a) a forward primer consisting of SEQ ID No: 16, and a reverse primer consisting of SEQ ID NO: 17;
(b) a forward primer consisting of SEQ ID No: 18, and a reverse primer consisting of SEQ ID NO: 19;
(c) a forward primer consisting of SEQ ID No: 20, and a reverse primer consisting of SEQ ID NO: 21;
(d) a forward primer consisting of SEQ ID No: 22, and a reverse primer consisting of SEQ ID NO: 23;
(e) a forward primer consisting of SEQ ID No: 28, and a reverse primer consisting of SEQ ID NO: 29;
(f) a forward primer consisting of SEQ ID No: 30, and a reverse primer consisting of SEQ ID NO: 31;
(g) a forward primer consisting of SEQ ID No: 32, and a reverse primer consisting of SEQ ID NO: 33;
(h) a forward primer consisting of SEQ ID No: 34, and a reverse primer consisting of SEQ ID NO: 35;
(i) a forward primer consisting of SEQ ID No: 40, and a reverse primer consisting of SEQ ID NO: 41;
(j) a forward primer consisting of SEQ ID No: 42, and a reverse primer consisting of SEQ ID NO: 43;
(k) a forward primer consisting of SEQ ID No: 44, and a reverse primer consisting of SEQ ID NO: 45;
(l) a forward primer consisting of SEQ ID No: 46, and a reverse primer consisting of SEQ ID NO: 47;
(m) a forward primer consisting of SEQ ID No: 48, and a reverse primer consisting of SEQ ID NO: 49;
(n) a forward primer consisting of SEQ ID No: 50, and a reverse primer consisting of SEQ ID NO: 51;
(o) a forward primer consisting of SEQ ID No: 52, and a reverse primer consisting of SEQ ID NO: 53;
(p) a forward primer consisting of SEQ ID No: 58, and a reverse primer consisting of SEQ ID NO: 59;
(q) a forward primer consisting of SEQ ID No: 60, and a reverse primer consisting of SEQ ID NO: 61;
(r) a forward primer consisting of SEQ ID No: 62, and a reverse primer consisting of SEQ ID NO: 63;
(s) a forward primer consisting of SEQ ID No: 64, and a reverse primer consisting of SEQ ID NO: 65;
(t) a forward primer consisting of SEQ ID No: 66, and a reverse primer consisting of SEQ ID NO: 67;
(u) a forward primer consisting of SEQ ID No: 68, and a reverse primer consisting of SEQ ID NO: 69;
(v) a forward primer consisting of SEQ ID No: 78, and a reverse primer consisting of SEQ ID NO: 79;
(w) a forward primer consisting of SEQ ID No: 80, and a reverse primer consisting of SEQ ID NO: 81; and
(x) a forward primer consisting of SEQ ID No: 46, and a reverse primer consisting of a sequence consisting of SEQ ID NO: 45 and two additional nucleotides on the 5' end of SEQ ID NO: 45;
(ii) a second container comprising;
a nucleic acid synthetase and at least one reagent selected from a buffering agent, a stabilizer, and a preservative; or
a substrate for a nucleic acid synthetase and at least one reagent selected from a buffering agent, a stabilizer, and a preservative; or
a double strand intercalator and at least one reagent selected from a buffering agent, a stabilizer, and a preservative; or
a signal detection substance and at least one reagent selected from a buffering agent, a stabilizer, and a preservative; and
(iii) a third container comprising a probe consisting of:
one of the nucleotide sequences of SEQ ID NOS: 1, 3, 4, 6, 7, 9, 10, or 13; or the full complement of one of the nucleotide sequences SEQ ID NOS: 1, 3, 4, 6, 7, 9, 10, or 13; or
15 to 50 contiguous bases or 100 contiguous bases to the full length of the nucleotide sequence consisting of one of SEQ ID NOS: 1, 3, 4, 6, 7, 9, 10, or 13; or 15 to 50 contiguous bases or 100 contiguous bases to the full length of the full complement of the nucleotide sequence consisting of one of SEQ ID NOS: 1, 3, 4, 6, 7, 9, 10, or 13; and
wherein the probe is capable of hybridizing with the genomic nucleotide sequence of *Mycobacterium intracellulare* gene; and
wherein at least one of the primers in each primer pair and/or the probe is labeled with a labeling substance, and
when at least one of the primers in each primer pair is labeled with a labeling substance, the labeling substance is bound to the primer via a covalent bond or a linker, wherein the labeling substance is a radioisotope, an enzyme, a fluorescent substance, a luminescent substance, or a biotin, and when the probe is labeled with a labeling substance, the labeling substance is bound to the probe via a covalent bond or a linker, wherein the labeling substance is a radioisotope, an enzyme, a fluorescent substance, a luminescent substance, or a biotin, or the 5' terminus of the probe is labeled with a reporter fluorescent dye and the 3'-terminus is labeled with a quencher dye.

* * * * *